US009248163B2

(12) United States Patent
Green et al.

(10) Patent No.: US 9,248,163 B2
(45) Date of Patent: *Feb. 2, 2016

(54) INSULIN-LIKE GROWTH FACTOR BINDING PROTEIN 7 FOR TREATMENT OF CANCER

(71) Applicant: University of Massachusetts, Boston, MA (US)

(72) Inventors: Michael Green, Boylston, MS (US); Narendra Wajapeyee, Hamden, MA (US)

(73) Assignee: University of Massachusetts, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/094,042

(22) Filed: Dec. 2, 2013

(65) Prior Publication Data
US 2014/0178339 A1 Jun. 26, 2014

Related U.S. Application Data

(63) Continuation of application No. 13/269,091, filed on Oct. 7, 2011, now Pat. No. 8,598,135, which is a continuation of application No. 12/209,028, filed on Sep. 11, 2008, now Pat. No. 8,034,792.

(60) Provisional application No. 60/993,211, filed on Sep. 11, 2007, provisional application No. 61/092,230, filed on Aug. 27, 2008.

(51) Int. Cl.
*A61K 41/00* (2006.01)
*C12Q 1/68* (2006.01)
*C07H 21/04* (2006.01)
*C12N 5/02* (2006.01)
*A61K 38/17* (2006.01)
*G01N 33/574* (2006.01)

(52) U.S. Cl.
CPC .......... *A61K 38/1754* (2013.01); *C12Q 1/6886* (2013.01); *G01N 33/5743* (2013.01)

(58) Field of Classification Search
None
See application file for complete search history.

(56) References Cited

U.S. PATENT DOCUMENTS

| 8,034,792 B2 | 10/2011 | Green et al. |
| 2004/0005294 A1 | 1/2004 | Lee |
| 2005/0148509 A1 | 7/2005 | Dake et al. |
| 2006/0084603 A1 | 4/2006 | Kirman et al. |
| 2006/0100144 A1 | 5/2006 | Lang et al. |
| 2006/0211073 A1 | 9/2006 | May et al. |
| 2007/0060607 A1 | 3/2007 | Bartkovitz et al. |

FOREIGN PATENT DOCUMENTS

| WO | WO 03/001985 | 1/2003 |
| WO | WO 2005/066371 | 7/2005 |
| WO | WO 2005/085861 | 9/2005 |
| WO | WO 2007039255 | 4/2007 |

OTHER PUBLICATIONS

Akaogi et al., "Synergistic growth stimulation of mouse fibroblasts by tumor-derived adhesion factor with insulin-like growth factors and insulin," Cell Growth Differ.,7:1671-77 (1996).
Alsina et al., "Detection of mutations in the mitogen-activated protein kinase pathway in human melanoma," Clin. Cancer Res., 9:6419-25 (2003).
Burger et al., "Down-regulation of T1A12/mac25, a novel insulin-like growth factor binding protein related gene, is associated with disease progression in breast carcinomas," Oncogene, 16:2459-67 (1998).
Burger et al., "Essential roles of IGFBP-3 and IGFBP-rP1 in breast cancer," Eur. J. Cancer, 41:1515-27 (2005).
Burger et al., "Mitogen-activated protein kinase signaling is activated in prostate tumors but not mediated by B-RAF mutations," Eur Urol. 50:1102-09 (2006).
Busby et al., "Detection of BRAF mutations in colorectal tumours and peritoneal washings using a mismatch ligation assay," J. Clin. Pathol., 58: 372-375 (2005).
Chen et al., "Insulin-like growth factor binding protein-related protein 1 (IGFBP-rP1) has potential tumour-suppressive activity in human lung cancer," J. Pathol., 211:431-438 (2007).
Chen et al., "In-vivo transfection of pcDNA3.1-IGFBP7 inhibits melanoma growth in mice through apoptosis induction and VEGF downexpression," J. Exp. Clin. Cancer Res., 29:13 (2010).
Chien and Lowe, "Secreting tumor suppression," Cell, 132:339-341 (2008).
Chung et al., "Detection of BRAFV600E mutation on fine needle aspiration specimen of thyroid nodule refines cyto-pathology diagnosis, especially in BRAF600E mutation-prevalent area," Clin. Endocrinol(Oxf), 65:660-666 (2006).
Cohen et al., "Lack of BRAF mutation in primary uveal melanoma," Invest. Ophthalmol. Vis. Sci. 44:28976-78 (2003).
Collado et al., "Senescence in premalignant tumours," Nature, 436:642 (2005).
Davies et al., "Mutations of the BRAF gene in human cancer," Nature, 417:949-954 (2002).
Deng et al., "BRAF mutation is frequently present in sporadic colorectal cancer with methylated hMLH1, but not in hereditary nonpolyposis colorectal cancer," Clin. Cancer Res. 10:191-195 (2004).
Dhomen and Marais, "New insight into BRAF mutations in cancer," Curr. Opin. Genet. Dev., 17:31-39 (2007).
Emley et al., "Oncogenic BRAF and the tumor suppressor IGFBP7 in the genesis of atypical spitzoid nevomelanocytic proliferations," J. Cutan. Pathol., 37:344-349 (2009).

(Continued)

*Primary Examiner* — Doug Schultz
(74) *Attorney, Agent, or Firm* — Fish & Richardson P.C.

(57) ABSTRACT

Methods of treating a tumor in a subject include identifying a subject having, at risk for, or suspected of having a tumor, and administering to the subject an effective amount of an IGFBP7 agent if the tumor has increased Ras-BRAF-MEK-Erk signaling, is dependent for growth and/or survival upon the Ras-BRAF-MEK-Erk signaling pathway, and/or expresses an activated or oncogenic BRAF or RAS.

20 Claims, 23 Drawing Sheets

(56) References Cited

OTHER PUBLICATIONS

Fecher et al., "Toward a molecular classification of melanoma," J. Clin. Oncol. 25:1606-20 (2007).
Fensterle et al., "B-Raf specific antibody responses in melanoma patients," BMC Cancer, 4:62 (2004).
Fridman et al., "Epigenetic and functional analysis of IGFBP3 and IGFBPrP1 in cellular immortalization," Biochem. Biophys. Res. Commun., 357:785-791 (2007).
Gazin et al., "An elaborate pathway required for RAS-mediated epigenetic silencing," Nature, 449:1073-77 (2007).
Goldenberg et al., "The V599E BRAF mutation is uncommon in biliary tract cancers," Mod. Pathol., 17:1386-91 (2004).
Goydos et al., "Detection of B-RAF and N-RAS mutations in human melanoma," J. Am. Coll. Surg., 200:362-370 (2005).
Gray-Schopfer et al., "Melanoma biology and new targeted therapy," Nature, 445:851-857 (2007).
Hayashida et al., "A rapid and simple detection method for the BRAF (T1796A) mutation in fine-needle aspirated thyroid carcinoma cells," Thyroid, 14:910-915 (2004).
Hinselwood et al., "BRAF mutation detection and identification by cycling temperature capillary electrophoresis," Electrophoresis, 26:2553-61 (2005).
Hoeflich et al., "Oncogenic BRAF is required for tumor growth and maintenance in melanoma models," Cancer Res., 66:999-1006 (2006).
Ichii-Nakato et al., "High frequency of BRAFV600E mutation in acquired nevi and small congenital nevi, but low frequency of mutation in medium-sized congenital nevi," J. Invest. Dermatol., 126:2111-18 (2006).
Ikenoue et al., "Rapid detection of mutations in the BRAF gene using real-time polymerase chain reaction and melting curve analysis," Cancer Genet. Cytogenet, 149:68-71 (2004).
International Search Report and Written Opinion, International Application No. PCT/US2008/076043 mailed Mar. 25, 2009.
Kann et al., "Improved marker combination for detection of de novo genetic variation and aberrant DNA in colorectal neoplasia," Clin. Chem. 52:2299-2302 (2006).
Kato et al., "A follistatin-like gene, mac25, may act as a growth suppressor of osteosarcoma cells," Oncogene, 12:1361-64 (1996).
Kato, "A secreted tumor-suppressor, mac25, with activin-binding activity," Mol. Med., 6:126-135 (2000).
Kawakami et al., "Immunological detection of altered signaling molecules involved in melanoma development," Cancer Metastasis Rev., 24:357-366 (2005).
Kim et al., "Development and applications of a BRAF oligonucleotide microarray," J. Mol. Diagn., 9:55-63 (2007).
Kim et al., "Identification of a Family of Low-Affinity Insulin-Like Growth Factor Binding Proteins (IGFBPs): Characterization of Connective Tissue Growth Factor as a Member of the IGFBP Superfamily," Proc. Natl. Acad. Sci. USA, 94:12981-86 (1997).
Kumagai et al., "Clinical Implications of Pre-Operative Rapid BRAF Analysis for Papillary Thyroid Cancer," Endocr. J., 54:399-405 (2007).
Lee et al., "BRAF mutations in non-Hodgkin's lymphoma," Br. J. Cancer, 10:1958-60 (2003).
Leppa et al., "Differential regulation of c-Jun by ERK and JNK during PC12 cell differentiation," EMBO J., 17:4404-13 (1998).
Lilleberg et al., "High sensitivity scanning of colorectal tumors and matched plasma DNA for mutations in APC, TP53, K-RAS, and BRAF genes with a novel DHPLC fluorescence detection platform," Ann N.Y. Acad. Sci, 1022:250-256 (2004).
Masson, et al., "Real-time allele-specific amplification for sensitive detection of the BRAF mutation V600E," Mol. Cell. Probes., 18:349-352 (2004).
Matsubara et al., "Impact of radiation and docetaxel on anti-tumor effects of insulin-like growth factor binding protein-related protein 1 (IGFBP-rP1) in hormone-refractory human prostate cancer cells," Proceedings of the American Association for Cancer Research Annual Meeting 48 p. 1258 (2007).

Matsukuma, et al., "Rapid and simple detection of hot spot point mutations of epidermal growth factor receptor, BRAF, and NRAS in cancers using the loop-hybrid mobility shift assay," J. Mol. Diagn., 8:504-512 (2006).
Michaloglou et al., "BRAF$^{E600}$-associated senescence-like cell cycle arrest of human naevi," Nature, 436:720-724 (2005).
Murphy et al., "Identification and Characterization of Genes Differentially Expressed in Meningiomas," Cell Growth & Differentiation, 4:715-722 (1993).
Mutaguchi et al., "Restoration of insulin-like growth factor binding protein-related protein 1 has a tumor-suppressive activity through induction of apoptosis in human prostate cancer," Cancer Res., 63:7717-23 (2003).
Namba et al., "Clinical implication of hot spot BRAF mutation, V599E, in papillary thyroid cancers," J. Clin. Endocr. Metab., 88:4393-97 (2003).
Nguyen et al., "BRAF V600E mutation and the tumour suppressor IGFBP7 in atypical genital naevi," Br. J. Dermatol., 162:677-680 (2009).
Oh et al., "Synthesis and characterization of insulin-like growth factor-binding protein (IGFBP)-7. Recombinant human mac25 protein specifically binds IGF-I and -II," J. Biol. Chem., 271:30322-25 (1996).
Oh, "IGFBPs and neoplastic models. New concepts for roles of IGFBPs in regulation of cancer cell growth," Endocrine, 7:111-113 (1997).
Oh, "IGF-independent regulation of breast cancer growth by IGF binding proteins," Breast Cancer Res. Treat., 47:283-293 (1998).
Palakurthy et al., "Epigenetic silencing of the RASSF1A tumor suppressor gene through HOXB3-mediated induction of DNMT3B expression," Mol. Cell., 36:219-230 (2009).
Park et al., "RKIP downregulates B-RAF kinase activity in melanoma cancer cells," Oncogene, 24:3535-40 (2005).
Peyssonnaux et al., "The Raf/MEK/ERK pathway: new concepts of activation," Biol. Cell, 93:53-62 (2001).
Plymate et al., "Increased manganese superoxide dismutase (SOD-2) is part of the mechanism for prostate tumor suppression by Mac25/insulin-like growth factor binding-protein-related protein-1," Oncogene, 22:1024-34 (2003).
Pollock et al., "Melanoma mouse model implicates metabotropic glutamate signaling in melanocytic neoplasia," Nature Genet., 33:19-20 (2003).
Powell et al., "Frequency of BRAF T1796A mutation in papillary thyroid carcinoma relates to age of patient at diagnosis and not to radiation exposure," J. Pathol., 205:558-564 (2005).
Pritchard et al., "Mouse models for BRAF-induced cancers," Biochem Soc. Trans., 35(Pt 5):1329-1333 (2007).
Razvan and Radulescua, "One for all and all for one: RB defends the cell while IDE, PTEN and IGFBP-7 antagonize insulin and IGFs to protect RB," Medical Hypotheses, 69:1018-20 (2007).
Ruan et al., "IGFBP7 plays a potential tumor suppressor role against colorectal carcinogenesis with its expression associated with DNA hypomethylation of exon 1," J. Zhejiang Univ. Sci. B, 7:929-932 (2006).
Ruan et al., "IGFBP7 plays a potential tumor suppressor role in colorectal carcinogenesis," Cancer Biol. Ther. 6:354-359 (2007).
Santra et al., "F-box protein FBX031 mediates cyclin D1 degradation to induce G1 arrest after DNA damage," Nature, 459:722-725 (2009).
Sapio, et al., "Detection of BRAF mutation in thyroid papillary carcinomas by mutant allele-specific PCR amplification (MASA)," Eur. J. Endocrinol., 154:341-348 (2006).
Sato et al., "Identification of cell-binding site of angiomodulin (AGM/TAF/Mac25) that interacts with heparan sulfates on cell surface," J. Cell. Biochem., 75:187-195 (1999).
Sato et al., "Strong suppression of tumor growth by insulin-like growth factor-binding protein-related protein 1/tumor-derived cell adhesion factor/mac25," Cancer Sci., 98:1055-63 (2007).
Schrama et al., "Lack of correlation between IGFBP7 expression and BRAF mutational status in melanoma," J. Invest. Dermatol., 130:897-898 (2010).
Scurr et al., "IGFBP7 is not required for B-RAF-induced melanocyte senescence," Cell, 141:717-727 (2010).

(56) References Cited

OTHER PUBLICATIONS

Sharma et al., "Mutant $^{V599E}$B-RAF regulates growth and vascular development of malignant melanoma tumors," Cancer Res., 65:2412-21 (2005).
Solit et al., "BRAF mutation predicts sensitivity to MEK inhibition," Nature, 439:358-362 (2006).
Sprenger et al., "Insulin-like growth factor binding protein-related protein 1 (IGFBP-rP1) is a potential tumor suppressor protein for prostate cancer," Cancer Res., 59:2370-75 (1999).
Sprenger et al., "Over-expression of insulin-like growth factor binding protein-related protein-1 (IGFBP-rP1/mac25) in the M12 prostate cancer cell line alters tumor growth by a delay in G1 and cyclin A associated apoptosis," Oncogene, 21:140-147 (2002).
Sridhar et al., "Raf kinase as a target for anticancer therapeutics," Mol. Cancer Ther., 4:677-685 (2005).
Subramanian et al., "Evidence for a tumour suppressive function of IGF1-binding proteins in human breast cancer," Anticancer Res., 27:3513-18 (2007).
Swisshelm et al., "Enhanced Expression of an Insulin Growth Factor-Like Binding Protein (mac25) in Senescent Human Mammary Epithelial Cells and Induced Expression with Retinoic Acid," Proc. Natl. Acad. Sci. USA, 92:4472-76 (1995).
Turner, et al., "Detection of the BRAF V600E mutation in melanocytic lesions using the ligase detection reaction," J. Cutan. Pathol., 32:334-339 (2005).
Van Beijnum et al., "Gene expression of tumor angiogenesis dissected: specific targeting of colon cancer angiogenic vasculature," Blood, 108:2339-48 (2006).
Wajapayee et al., "Efficacy of IGFBP7 for treatment of metastatic melanoma and other cancers in mouse models and human cell lines," Mol. Cancer Ther., 8:3009-14 (2009).
Wajapayee et al., "Oncogenic BRAF induces senescence and apoptosis through pathways mediated by the secreted protein IGFBP7," Cell, 132:363-374 (2008).
Wajapeyee et al., "Role for IGFBP7 in senescence induction by BRAF," Cell, 141:746-747 (2010).
Wei et al., "Expression and function of insulin-like growth factor binding protein 7 (IGFBP-7/IGFBP-rP1) in glioma cell," Proceedings of the American Association for Cancer Research Annual Meeting 47 p. 775-776 (2006).
Willmore-Payne, et al., "Human malignant melanoma: detection of BRAF- and c-kit-activating mutations by high-resolution amplicon melting analysis," Hum. Pathol., 36:486-493 (2005).
Wilson et al., "Generation and characterization of an IGFBP-7 antibody: identification of 3 1kD IGFBP-7 in human biological fluids and Hs578T human breast cancer conditioned media," J. Clin. Endocrinol. Metab., 82:1301-03 (1997).
Wilson et al., "Insulin-like growth factor binding protein-related protein 1 inhibits proliferation of MCF-7 breast cancer cells via a senescence-like mechanism," Cell Growth Differ., 13:205-213 (2002).
Wilson et al., "Interaction of IGF-Binding Protein-Related Protein 1 with a Novel Protein, Neuroendocrine Differentiation Factor, Results in Neuroendocrine Differentiation of Prostate Cancer Cells," J. Clin Endrocinol. Metab., 86:4504-11 (2001).
Xing et al., "Detection of BRAF mutation on fine needle aspiration biopsy specimens: A new diagnostic tool for papillary thyroid cancer," J. Clin. Endocrinol Metab., 89:2867-72 (2004).
Yamauchi et al., "Purification and molecular cloning of prostacyclin-stimulating factor from serum, free conditioned medium of human diploid fibroblast cells," Biochem J., 303:591-598 (1994).
Zhu et al., "Senescence of human fibroblasts induced by oncogenic Raf," Genes Dev., 12:2997-3007 (1998).
Canadian Intellection Property Office, "Office Action", Application No. 2,699,290, issued on Jun. 5, 2014, 3 pages.
Yuichiro, S. et al., "Strong suppression of tumor growth by insulin-like growth factor-binding protein-related protein 1/tumor-derived cell adhesion factor/mac25", *Cancer Science*, vol. 98(7):1055-1063 (2007).
European Search Report issued in Application EP 08 83 0697 on Feb. 27, 2013.
Japanese Office Action dated Jun. 3, 2013, issued in corresponding Japanese Application No. 2010-524988.
Teishima, Jun, "Decreased Expression of Insulin-like Growth Factor Binding Protein-related Protein-1 (IGFBP-rP1) in Radiation-induced Mouse Hepatocellular Carcinoma," Medical Journal of Hiroshima University, 2002, vol. 50, No. 2, p. 63-71.
Ikenoua, Tsuneo, "B-RAF Gene Mutations in Colorectal Cancer," Biotherapy, 2006, vol. 20, No. 1, p. 91-96.
GenBank Accession No. NP_001544 (Jul. 30, 2007).
Daniotti, M. et al., "Detection of mutated BRAFV600E variant in circulating DNA of stage III-IV melanoma patients", Int. J. Cancer, vol. 120:2439-2444 (2007).
Korean Intellectual Property Office, English Translation of the Notice to File a Response, issued in corresponding KR Application No. 10-2010-7007906, on Mar. 27, 2015, 14 pages.
Canadian Intellection Property Office, Office Action for Application No. 2,699,290, issued on Oct. 21, 2015, 4 pages.

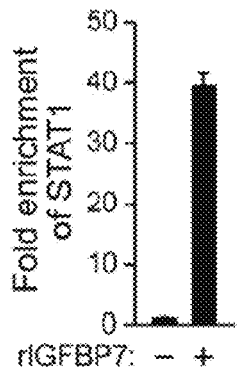
FIG. 3E
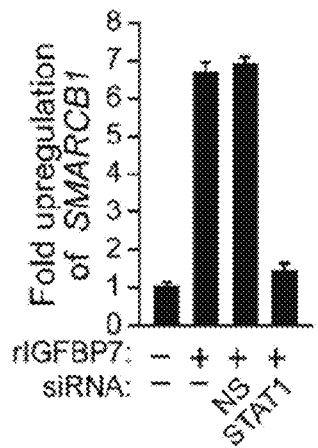
FIG. 3F
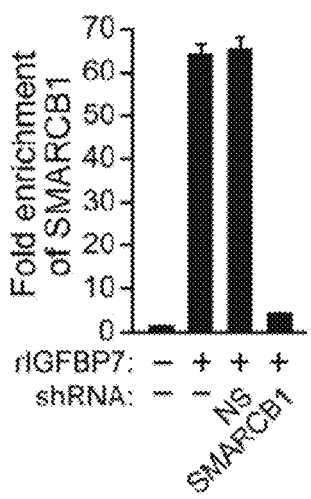
FIG. 3G
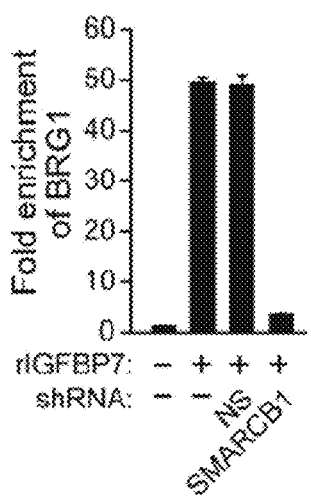
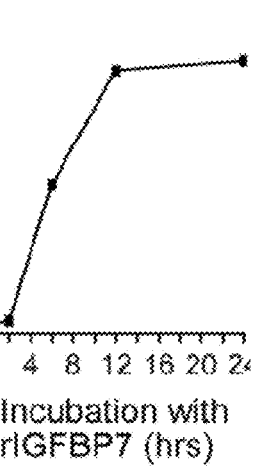
FIG. 3H

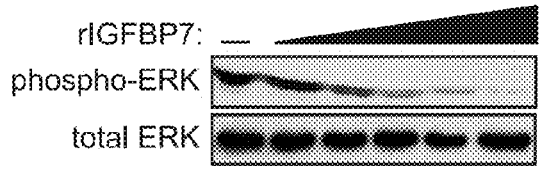
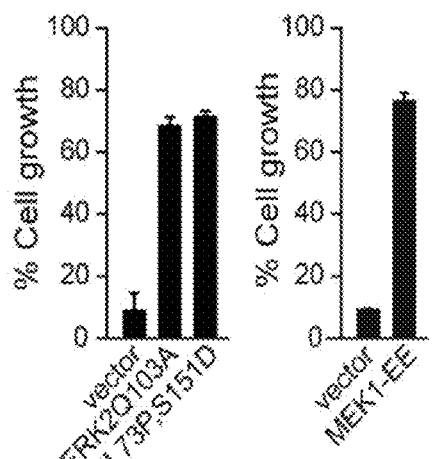
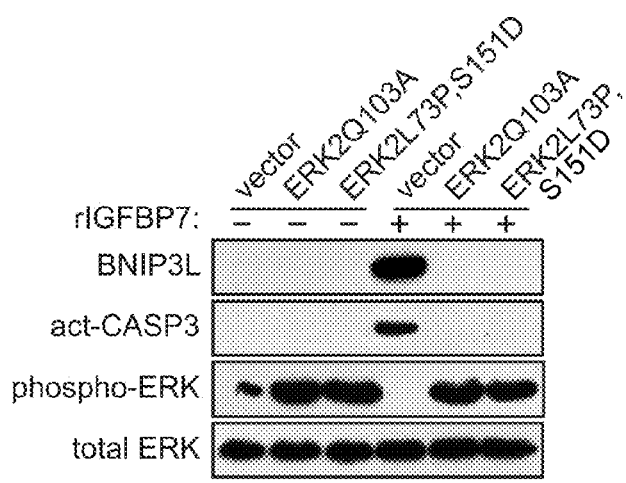
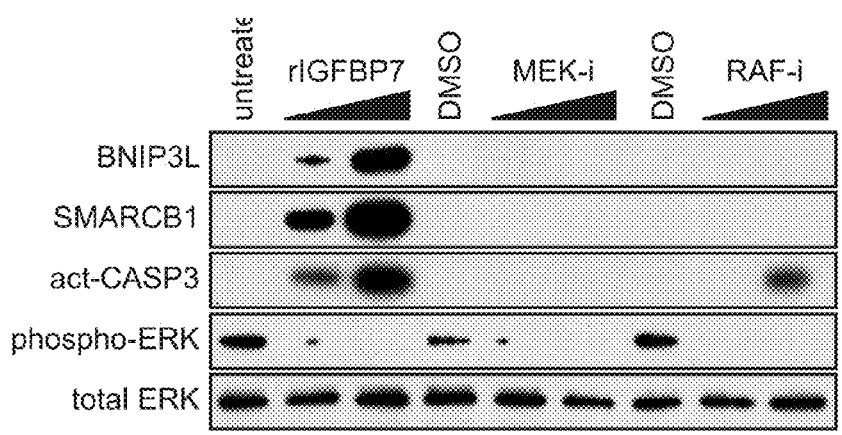
FIG. 4A
FIG. 4B
FIG. 4C
FIG. 4D

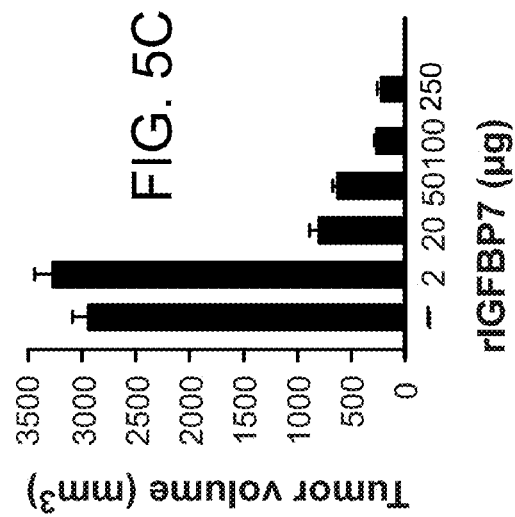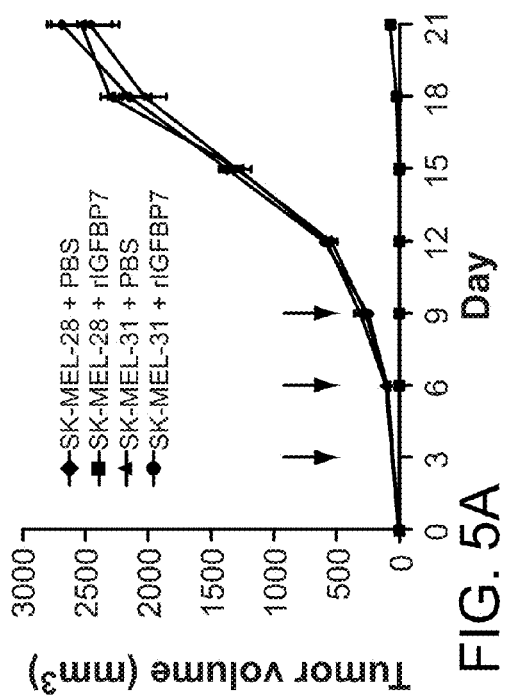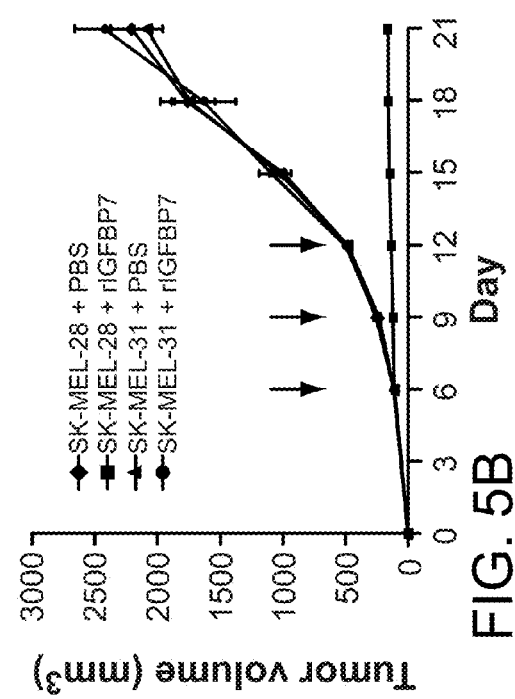

Human IGFBP7 Polypeptide Sequence (GenBank Accession No. NP_001544)

MERPSLRALLLGAAGLLLLLLPLSSSSSSDTCGPCEPASCPPLPPLGCLLGETRDACGCCPM
CARGEGEPCGGGGAGRGYCAPGMECVKSRKRRKGKAGAAAGGPGVSGVCVCKSRYPVCGSDG
TTYPSGCQLRAASQRAESRGEKAITQVSKGTCEQGPSIVTPPKDIWNVTGAQVYLSCEVIGI
PTPVLIWNKVKRGHYGVQRTELLPGDRDNLAIQTRGGPEKHEVTGWVLVSPLSKEDAGEYEC
HASNSQGQASASAKITVVDALHEIPVKKGEGAEL    (SEQ ID NO:1)

FIG. 7A

Human IGFBP7 mRNA Sequence (GenBank Accession No. NM_001553)

GCCGCTGCCACCGCACCCCGCCATGGAGCGGCCGTCGCTGCGCGCCCTGCTCCTCGGCGCCG
CTGGGCTGCTGCTCCTGCTCCTGCCCCTCTCCTCTTCCTCCTCTTCGGACACCTGCGGCCCC
TGCGAGCCGGCCTCCTGCCCGCCCCTGCCCCCGCTGGGCTGCCTGCTGGGCGAGACCCGCGA
CGCGTGCGGCTGCTGCCCTATGTGCGCCCGCGGCGAGGGCGAGCCGTGCGGGGGTGGCGGCG
CCGGCAGGGGGTACTGCGCGCCGGGCATGGAGTGCGTGAAGAGCCGCAAGAGGCGGAAGGGT
AAAGCCGGGGCAGCAGCCGGCGGTCCGGGTGTAAGCGGCGTGTGCGTGTGCAAGAGCCGCTA
CCCGGTGTGCGGCAGCGACGGCACCACCTACCCGAGCGGCTGCCAGCTGCGCGCCGCCAGCC
AGAGGGCCGAGAGCCGCGGGGAGAAGGCCATCACCCAGGTCAGCAAGGGCACCTGCGAGCAA
GGTCCTTCCATAGTGACGCCCCCAAGGACATCTGGAATGTCACTGGTGCCCAGGTGTACTT
GAGCTGTGAGGTCATCGGAATCCCGACACCTGTCCTCATCTGGAACAAGGTAAAAGGGGTC
ACTATGGAGTTCAAAGGACAGAACTCCTGCCTGGTGACCGGGACAACCTGGCCATTCAGACC
CGGGGTGGCCCAGAAAAGCATGAAGTAACTGGCTGGGTGCTGGTATCTCCTCTAAGTAAGGA
AGATGCTGGAGAATATGAGTGCCATGCATCCAATTCCCAAGGACAGGCTTCAGCATCAGCAA
AAATTACAGTGGTTGATGCCTTACATGAAATACCAGTGAAAAAGGTGAAGGTGCCGAGCTA
TAAACCTCCAGAATATTATTAGTCTGCATGGTTAAAAGTAGTCATGGATAACTACATTACCT
GTTCTTGCCTAATAAGTTTCTTTTAATCCAATCCACTAACACTTTAGTTATATTCACTGGTT
TTACACAGAGAAATACAAAATAAAGATCACACATCAAGACTATCTACAAAAATTTATTATAT
ATTTACAGAAGAAAGCATGCATATCATTAAACAAATAAATACTTTTTATCACAAAAAAAA
AAAAAAAA    (SEQ ID NO:2)

FIG. 7B

Human BRAF Polypeptide Sequence (GenBank Accession No. NP_004324)

MAALSGGGGGGAEPGQALFNGDMEPEAGAGAGAAASSAADPAIPEEVWNIKQMIKLTQEHIEALLDKFGGEHNPP
SIYLEAYEEYTSKLDALQQREQQLLESLGNGTDFSVSSSASMDTVTSSSSSSLSVLPSSLSVFQNPTDVARSNPK
SPQKPIVRVFLPNKQRTVVPARCGVTVRDSLKKALMMRGLIPECCAVYRIQDGEKKPIGWDTDISWLTGEELHVE
VLENVPLTTHNFVRKTFFTLAFCDFCRKLLFQGFRCQTCGYKFHQRCSTEVPLMCVNYDQLDLLFVSKFFEHHPI
PQEEASLAETALTSGSSPSAPASDSIGPQILTSPSPSKSIPIPQPFRPADEDHRNQFGQRDRSSSAPNVHINTIE
PVNIDDLIRDQGFRGDGGSTTGLSATPPASLPGSLTNVKALQKSPGFQRERKSSSSSEDRNRMKTLGRRDSSDDW
EIPDGQITVGQRIGSGSFGTVYKGKWHGDVAVKMLNVTAPTPQQLQAFKNEVGVLRKTRHVNILLFMGYSTKPQL
AIVTQWCEGSSLYHHLHIIETKFEMIKLIDIARQTAQGMDYLHAKSIIHRDLKSNNIFLHEDLTVKIGDFGLATV
KSRWSGSHQFEQLSGSILWMAPEVIRMQDKNPYSFQSDVYAFGIVLYELMTGQLPYSNINNRDQIIFMVGRGYLS
PDLSKVRSNCPKAMKRLMAECLKKKRDERPLFPQILASIELLARSLPKIHRSASEPSLNRAGFQTEDFSLYACAS
PKTPIQAGGYGAFPVH   (SEQ ID NO:3)

FIG. 8A

Human BRAF mRNA Sequence (GenBank Accession No. NM_004333)

CGCCTCCCTTCCCCCTCCCCGCCCGACAGCGGCCGCTCGGGCCCGGCTCTCGGTTATAAGATGGCGGCGCTGAG
CGGTGGCGGTGGTGGCGGCGCGGAGCCGGGCCAGGCTCTGTTCAACGGGGACATGGAGCCCGAGGCCGGCGCCGG
CGCCGGCGCCGCGGCCTCTTCGGCTGCGGACCCTGCCATTCCGGAGGAGGTGTGGAATATCAAACAAATGATTAA
GTTGACACAGGAACATATAGAGGCCCTATTGGACAAATTTGGTGGGGAGCATAATCCACCATCAATATATCTGGA
GGCCTATGAAGAATACACCAGCAAGCTAGATGCACTCCAACAAAGAGAACAACAGTTATTGGAATCTCTGGGGAA
CGGAACTGATTTTTCTGTTTCTAGCTCTGCATCAATGGATACCGTTACATCTTCTTCCTCTTCTAGCCTTTCAGT
GCTACCTTCATCTCTTTCAGTTTTTCAAAATCCCACAGATGTGGCACGGAGCAACCCCAAGTCACCACAAAAACC
TATCGTTAGAGTCTTCCTGCCCAACAAACAGAGGACAGTGGTACCTGCAAGGTGTGGAGTTACAGTCCGAGACAG
TCTAAAGAAAGCACTGATGATGAGAGGTCTAATCCCAGAGTGCTGTGCTGTTTACAGAATTCAGGATGGAGAGAA
GAAACCAATTGGTTGGGACACTGATATTTCCTGGCTTACTGGAGAAGAATTGCATGTGGAAGTGTTGGAGAATGT
TCCACTTACAACACACAACTTTGTACGAAAAACGTTTTTCACCTTAGCATTTTGTGACTTTTGTCGAAAGCTGCT
TTTCCAGGGTTTCCGCTGTCAAACATGTGGTTATAAATTTCACCAGCGTTGTAGTACAGAAGTTCCACTGATGTG
TGTTAATTATGACCAACTTGATTTGCTGTTTGTCTCCAAGTTCTTTGAACACCACCCAATACCACAGGAAGAGGC
GTCCTTAGCAGAGACTGCCCTAACATCTGGATCATCCCCTTCCGCACCCGCCTCGGACTCTATTGGGCCCCAAAT
TCTCACCAGTCCGTCTCCTTCAAAATCCATTCCAATTCCACAGCCCTTCCGACCAGCAGATGAAGATCATCGAAA
TCAATTTGGGCAACGAGACCGATCCTCATCAGCTCCCAATGTGCATATAAACACAATAGAACCTGTCAATATTGA
TGACTTGATTAGAGACCAAGGATTTCGTGGTGATGGAGGATCAACCACAGGTTTGTCTGCTACCCCCCCTGCCTC
ATTACCTGGCTCACTAACTAACGTGAAAGCCTTACAGAAATCTCCAGGACCTCAGCGAGAAAGGAAGTCATCTTC
ATCCTCAGAAGACAGGAATCGAATGAAAACACTTGGTAGACGGGACTCGAGTGATGATTGGGAGATTCCTGATGG
GCAGATTACAGTGGGACAAAGAATTGGATCTGGATCATTTGGAACAGTCTACAAGGGAAAGTGGCATGGTGATGT
GGCAGTGAAAATGTTGAATGTGACAGCACCTACACCTCAGCAGTTACAAGCCTTCAAAAATGAAGTAGGAGTACT
CAGGAAAACACGACATGTGAATATCCTACTCTTCATGGGCTATTCCACAAAGCCACAACTGGCTATTGTTACCCA
GTGGTGTGAGGGCTCCAGCTTGTATCACCATCTCCATATCATTGAGACCAAATTTGAGATGATCAAACTTATAGA
TATTGCACGACAGACTGCACAGGGCATGGATTACTTACACGCCAAGTCAATCATCCACAGAGACCTCAAGAGTAA
TAATATATTTCTTCATGAAGACCTCACAGTAAAAATAGGTGATTTTGGTCTAGCTACAGTGAAATCTCGATGGAG
TGGGTCCCATCAGTTTGAACAGTTGTCTGGATCCATTTTGTGGATGGCACCAGAAGTCATCAGAATGCAAGATAA
AAATCCATACAGCTTTCAGTCAGATGTATATGCATTTGGAATTGTTCTGTATGAATTGATGACTGGACAGTTACC
TTATTCAAACATCAACAACAGGGACCAGATAATTTTTATGGTGGGACGAGGATACCTGTCTCCAGATCTCAGTAA
GGTACGGAGTAACTGTCCAAAAGCCATGAAGAGATTAATGGCAGAGTGCCTCAAAAAGAAAAGAGATGAGAGACC
ACTCTTTCCCCAAATTCTCGCCTCTATTGAGCTGCTGGCCCGCTCATTGCCAAAAATTCACCGCAGTGCATCAGA
ACCCTCCTTGAATCGGGCTGGTTTCCAAACAGAGGATTTTAGTCTATATGCTTGTGCTTCTCCAAAAACACCCAT
CCAGGCAGGGGGATATGGTGCGTTTCCTGTCCACTGAAACAAATGAGTGAGAGAGTTCAGGAGAGTAGCAACAAA
AGGAAAATAAATGAACATATGTTTGCTTATATGTTAAATTGAATAAAATACTCTCTTTTTTTTAAGGTGAACCA
AA   (SEQ ID NO:4)

FIG. 8B

Human NRAS Polypeptide Sequence (GenBank Accession No. NP_002515)

MTEYKLVVVGAGGVGKSALTIQLIQNHFVDEYDPTIEDSYRKQVVIDGETCLLDILDTAGQE
EYSAMRDQYMRTGEGFLCVFAINNSKSFADINLYREQIKRVKDSDDVPMVLVGNKCDLPTRT
VDTKQAHELAKSYGIPFIETSAKTRQGVEDAFYTLVREIRQYRMKKLNSSDDGTQGCMGLPC
VVM   (SEQ ID NO:5)

FIG. 9A

Human NRAS mRNA Sequence (GenBank Accession No. NM_002524)

GAAACGTCCCGTGTGGGAGGGGCGGGTCTGGGTGCGGCTGCCGCATGACTCGTGGTTCGGAG
GCCCACGTGGCCGGGGCGGGGACTCAGGCGCCTGGCAGCCGACTGATTACGTAGCGGGCGGG
GCCGGAAGTGCCGCTCCTTGGTGGGGGCTGTTCATGGCGGTTCCGGGGTCTCCAACATTTTT
CCCGGTCTGTGGTCCTAAATCTGTCCAAAGCAGAGGCAGTGGAGCTTGAGGTTCTTGCTGGT
GTGAAATGACTGAGTACAAACTGGTGGTGGTTGGAGCAGGTGGTGTTGGGAAAAGCGCACTG
ACAATCCAGCTAATCCAGAACCACTTTGTAGATGAATATGATCCCACCATAGAGGATTCTTA
CAGAAAACAAGTGGTTATAGATGGTGAAACCTGTTTGTTGGACATACTGGATACAGCTGGAC
AAGAAGAGTACAGTGCCATGAGAGACCAATACATGAGGACAGGCGAAGGCTTCCTCTGTGTA
TTTGCCATCAATAATAGCAAGTCATTTGCGGATATTAACCTCTACAGGGAGCAGATTAAGCG
AGTAAAAGACTCGGATGATGTACCTATGGTGCTAGTGGGAAACAAGTGTGATTTGCCAACAA
GGACAGTTGATACAAAACAAGCCCACGAACTGGCCAAGAGTTACGGGATTCCATTCATTGAA
ACCTCAGCCAAGACCAGACAGGGTGTTGAAGATGCTTTTTACACACTGGTAAGAGAAATACG
CCAGTACCGAATGAAAAAACTCAACAGCAGTGATGATGGGACTCAGGGTTGTATGGGATTGC
CATGTGTGGTGATGTAACAAGATACTTTTAAAGTTTTGTCAGAAAAGAGCCACTTTCAAGCT
GCACTGACACCCTGGTCCTGACTTCCTGGAGGAGAAGTATTCCTGTTGCTGTCTTCAGTCTC
ACAGAGAAGCTCCTGCTACTTCCCCAGCTCTCAGTAGTTTAGTACAATAATCTCTATTTGAG
AAGTTCTCAGAATAACTACCTCCTCACTTGGCTGTCTGACCAGAGAATGCACCTCTTGTTAC
TCCCTGTTATTTTTCTGCCCTGGGTTCTTCCACAGCACAAACACACCTCAACACACCTCTGC
CACCCCAGGTTTTTCATCTGAAAAGCAGTTCATGTCTGAAACAGAGAACCAAACCGCAAACG
TGAAATTCTATTGAAAACAGTGTCTTGAGCTCTAAAGTAGCAACTGCTGGTGATTTTTTTTT
TCTTTTTACTGTTGAACTTAGAACTATGCCTAATTTTTGGAGAAATGTCATAAATTACTGTT
TTGCCAAGAATATAGTTATTATTGCTGTTTGGTTTGTTTATAATGTTATCGGCTCTATTCTC
TAAACTGGCATCTGCTCTAGATTCATAAATACAAAAATGAATACTGAATTTTGAGTCTATCC
TAGTCTTCACAACTTTGACGTAATTAAATCCAACTTTTCACAGTGAAGTGCCTTTTTCCTAG
AAGTGGTTTGTAGACTCCTTTATAATATTTCAGTGGAATAGATGTCTCAAAAATCCTTATGC
ATGAAATGAATGTCTGAGATACGTCTGTGACTTATCTACCATTGAAGGAAAGCTATATCTAT
TTGAGAGCAGATGCCATTTTGTACATGTATGAAATTGGTTTTCCAGAGGCCTGTTTTGGGGC
TTTCCCAGGAGAAAGATGAAACTGAAAGCATATGAATAATTTCACTTAATAATTTTTACCTA
ATCTCCACTTTTTTCATAGGTTACTACCTATACAATGTATGTAATTTGTTTCCCCTAGCTTA
CTGATAAACCTAATATTCAATGAACTTCCATTTGTATTCAAATTTGTGTCATACCAGAAAGC
TCTACATTTGCAGATGTTCAAATATTGTAAAACTTTGGTGCATTGTTATTTAATAGCTGTGA
TCAGTGATTTTCAAACCTCAAATATAGTATATTAACAAATT   (SEQ ID NO:6)

FIG. 9B

INSULIN-LIKE GROWTH FACTOR BINDING PROTEIN 7 FOR TREATMENT OF CANCER

This application is a continuation of U.S. application Ser. No. 13/269,091, filed on Oct. 7, 2011, which is a continuation of U.S. application Ser. No. 12/209,028, filed on Sep. 11, 2008, which claims the benefit of U.S. Provisional Patent Application Ser. No. 60/993,211, filed on Sep. 11, 2007 and U.S. Provisional Patent Application Ser. No. 61/092,230, filed on Aug. 27, 2008. The entire contents of the prior applications are incorporated by reference herein.

GOVERNMENT FUNDING

This invention was made with government support under National Institutes of Health grant CA115817. The government has certain rights in the invention.

TECHNICAL FIELD

This invention relates to treatment of cancers with agents that include a polypeptide.

BACKGROUND

Activating V-Raf murine sarcoma viral oncogene homolog B1 (BRAF) mutations are prevalent in numerous types of cancers, including 50-70% of melanomas, 15% of colorectal and ovarian cancers, and 36-69% of papillary thyroid carcinomas (reviewed in Davies et al., 2002, Nature, 417:949-954; and Namba et al., 2003, J. Clin. Endocr. Metab., 88:4393-97). Activating BRAF mutations have also been identified in up to 82% of benign melanocytic tumors (nevi) (Pollock et al., 2003, Nature Genet., 33:19-20). The most common activating BRAF mutation is a glutamic acid to valine substitution at position 600 (V600E; formerly identified as V599E). This mutation produces a highly active kinase that stimulates constitutive extracellular signal-regulated protein kinase (ERK) signaling. Expression of BRAFV600E has been shown to induce senescence in cultured human fibroblasts (Zhu et al., 1998, Genes Dev., 12:2997-3007) and human melanocytes (Michaloglou et al., 2005, Nature, 436:720-724) and in vivo in preneoplastic nevi (Michaloglou et al., 2005, Nature, 436: 720-724).

SUMMARY

This disclosure is based, in part, on the surprising discovery that insulin-like growth factor binding protein 7 (IGFBP7) induces senescence and/or apoptosis in cells with increased Ras-BRAF-MEK-Erk signaling, e.g., cells that express activated forms of BRAF or a RAS viral oncogene homolog (RAS) (e.g., neuroblastoma RAS viral oncogene homolog (NRAS), V-KI-RAS2 Kirsten rat sarcoma viral oncogene homolog (KRAS), or V-HA-RAS Harvey rat sarcoma viral oncogene homolog (HRAS)). Described herein are methods of diagnosing and treating tumors (e.g., cancers), inducing cellular apoptosis, inducing cellular senescence, and inhibiting cellular proliferation using IGFBP7 agents.

In one aspect, this application features methods of treating a tumor in a subject by identifying a subject having, at risk for, or suspected of having a tumor; and administering to the subject an effective amount of an IGFBP7 agent, thereby treating the tumor. In some embodiments, the tumor is a cancer (e.g., a melanoma, carcinoma, breast cancer, ovarian cancer, pancreatic cancer, colorectal carcinoma, or papillary thyroid carcinoma). In some embodiments, the tumor has increased Ras-BRAF-MEK-Erk signaling. In some embodiments, the tumor is dependent for growth and/or survival upon the Ras-BRAF-MEK-Erk signaling pathway. In some embodiments, the tumor expresses an activated or oncogenic BRAF or RAS (e.g., NRAS, KRAS, or HRAS). In some embodiments, the activated or oncogenic BRAF has a valine to glutamine mutation at residue 600 (BRAFV600E).

In some embodiments, the methods further include evaluating a sample from the subject to determine the presence of increased Ras-BRAF-MEK-Erk signaling, dependence for growth and/or survival upon the Ras-BRAF-MEK-Erk signaling pathway, and/or an activated or oncogenic BRAF or RAS, and selecting the subject for treatment on the basis of the presence of the increased Ras-BRAF-MEK-Erk signaling, dependence for growth and/or survival upon the Ras-BRAF-MEK-Erk signaling pathway, and/or activated or oncogenic BRAF or RAS. In some embodiments, the sample includes a cell, nucleic acid, or polypeptide from the tumor. In some embodiments, the activated or oncogenic BRAF has a valine to glutamine mutation at residue 600 (BRAFV600E).

In another aspect, this application features methods of inducing senescence in a cell (e.g., a tumor cell) that has increased Ras-BRAF-MEK-Erk signaling, is dependent for growth and/or survival upon the Ras-BRAF-MEK-Erk signaling pathway, and/or expresses an activated or oncogenic BRAF or RAS (e.g., NRAS, KRAS, or HRAS) that include administering to the cell an effective amount of an IGFBP7 agent. In some embodiments, the cell is a tumor cell.

In a further aspect, this application features methods of inducing apoptosis in a cell (e.g., a tumor cell) that has increased Ras-BRAF-MEK-Erk signaling, is dependent for growth and/or survival upon the Ras-BRAF-MEK-Erk signaling pathway, and/or expresses an activated or oncogenic BRAF or RAS (e.g., NRAS, KRAS, or HRAS) that include administering to the cell an effective amount of an IGFBP7 agent.

In another aspect, this application features methods of inhibiting proliferation of a cell (e.g., a tumor cell) that has increased Ras-BRAF-MEK-Erk signaling, is dependent for growth and/or survival upon the Ras-BRAF-MEK-Erk signaling pathway, and/or expresses activated or oncogenic BRAF or RAS (e.g., NRAS, KRAS, or HRAS), in which the methods include administering to the cell an effective amount of an IGFBP7 agent.

In a further aspect, this application features methods of inhibiting growth (e.g., metastatic growth) in a subject of a tumor that contains a cell that has increased Ras-BRAF-MEK-Erk signaling, is dependent for growth and/or survival upon the Ras-BRAF-MEK-Erk signaling pathway, and/or expresses an activated or oncogenic BRAF or RAS (e.g., NRAS, KRAS, or HRAS) that include administering to the subject an effective amount of an IGFBP7 agent.

In another aspect, this application features the use of an IGFBP7 agent in the preparation of a medicament for the treatment of a tumor or cancer (e.g., a melanoma, carcinoma, breast cancer, ovarian cancer, pancreatic cancer, colorectal carcinoma, or papillary thyroid carcinoma) in a subject. In some embodiments, the tumor has increased Ras-BRAF-MEK-Erk signaling, is dependent for growth and/or survival upon the Ras-BRAF-MEK-Erk signaling pathway, and/or expresses an activated BRAF or RAS (e.g., NRAS, KRAS, or HRAS). In some embodiments, the tumor or cancer is metastatic.

In a further aspect, this application features an isolated IGFBP7 agent for treating a tumor or cancer (e.g., a melanoma, carcinoma, breast cancer, ovarian cancer, pancreatic cancer, colorectal carcinoma, or papillary thyroid carcinoma)

in a subject. In some embodiments, the tumor has increased Ras-BRAF-MEK-Erk signaling, is dependent for growth and/or survival upon the Ras-BRAF-MEK-Erk signaling pathway, and/or expresses an activated BRAF or RAS (e.g., NRAS, KRAS, or HRAS). In some embodiments, the tumor or cancer is metastatic.

In some embodiments, the IGFBP7 agent is a composition that includes a polypeptide at least 80% identical (e.g., at least 85%, 90%, 95%, 98%, or 99% identical) to SEQ ID NO:1 or SEQ ID NO:7. The polypeptide can be conjugated to a heterologous moiety (e.g., a heterologous polypeptide sequence). In some embodiments, the IGFBP7 agent includes a functional fragment or domain of SEQ ID NO:1 or SEQ ID NO:7. The IGFBP7 agent can be administered, e.g., topically, systemically, or locally (e.g., by a drug-releasing implant).

In some embodiments, the IGFBP7 agent is administered by introducing into the subject a composition that induces the expression of IGFBP7 or an active fragment or analog thereof, e.g., a nucleic acid encoding a polypeptide at least 80% identical (e.g., at least 85%, 90%, 95%, 98%, or 99% identical) to SEQ ID NO:1 or SEQ ID NO:7. The nucleic acid can be in a vector, e.g., a viral vector (e.g., an adenovirus vector, an adeno-associated virus vector, a retrovirus vector, or a lentivirus vector). In some embodiments, the IGFBP7 agent is administered by introducing into the subject a cell that a nucleic acid encoding a polypeptide at least 80% identical (e.g., at least 85%, 90%, 95%, 98%, or 99% identical) to SEQ ID NO:1 or SEQ ID NO:7 that secretes the polypeptide.

In another aspect, this application features methods of diagnosing a lesion (e.g., a melanocytic skin lesion) that include: obtaining a sample of a lesion (e.g., a melanocytic skin lesion) (e.g., a tissue sample, cell sample, protein sample, or nucleic acid sample) and determining the expression of IGFBP7 in the sample, wherein the lesion is diagnosed as benign (e.g., a melanocytic nevus) if the sample detectably expresses IGFBP7 and wherein the lesion is diagnosed as cancerous (e.g., a melanoma) if the sample does not express IGFBP7. In some embodiments, the methods include determining whether the sample has increased Ras-BRAF-MEK-Erk signaling, is dependent for growth and/or survival upon the Ras-BRAF-MEK-Erk signaling pathway, and/or contains an activated BRAF or RAS (e.g., BRAFV600E) and diagnosing the lesion as benign (e.g., a melanocytic nevus) if the sample expresses IGFBP7 and has increased Ras-BRAF-MEK-Erk signaling, is dependent for growth and/or survival upon the Ras-BRAF-MEK-Erk signaling pathway, and/or contains an activated BRAF or RAS. The lesion is diagnosed as cancerous (e.g., a melanoma) if the sample does not express IGFBP7 and has increased Ras-BRAF-MEK-Erk signaling, is dependent for growth and/or survival upon the Ras-BRAF-MEK-Erk signaling pathway, and/or contains an activated BRAF or RAS. In some embodiments, the methods include determining whether the sample has increased Ras-BRAF-MEK-Erk signaling, is dependent for growth and/or survival upon the Ras-BRAF-MEK-Erk signaling pathway, and/or contains an activated BRAF or RAS (e.g., BRAFV600E) and diagnosing the lesion as benign (e.g., a melanocytic nevus) if the sample expresses IGFBP7 and has increased Ras-BRAF-MEK-Erk signaling, is dependent for growth and/or survival upon the Ras-BRAF-MEK-Erk signaling pathway, and/or contains an activated BRAF or RAS and diagnosing the lesion as cancerous (e.g., a melanoma) if the sample expresses IGFBP7 but does not have increased Ras-BRAF-MEK-Erk signaling, is not dependent for growth and/or survival upon the Ras-BRAF-MEK-Erk signaling pathway, and/or does not contain an activated BRAF or RAS.

"Polypeptide" and "protein" are used interchangeably and mean any peptide-linked chain of amino acids, regardless of length or post-translational modification.

As used herein, a subject "at risk of developing cancer" is a subject that has a predisposition to develop cancer, i.e., a genetic or familial predisposition to develop cancer or has been exposed to conditions that can result in cancer. From the above it will be clear that subjects "at risk of developing cancer" are not all subjects.

A subject "suspected of having cancer" is one having one or more symptoms of cancer. Symptoms of cancer are well-known to those of skill in the art and include, without limitation, weight loss, weakness, excessive fatigue, difficulty eating, loss of appetite, unusual mole features, newly pigmented skin area, skin growths, skin ulcers, skin lumps, chronic cough, worsening breathlessness, breathing difficulty, enlarged lymph nodes, coughing up blood, blood in the urine, blood in stool, nausea, vomiting, liver metastases, lung metastases, bone metastases, breast or nipple changes, nipple discharge, abdominal fullness, bloating, fluid in peritoneal cavity, constipation, abdominal distension, perforation of colon, acute peritonitis (infection, fever, pain), vaginal bleeding, pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, pancreas metastases, difficulty swallowing, and the like. For example, a patient who has been diagnosed by a physician as having cancer is still suspected of having cancer.

The term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A (bottom) is a bar graph depicting proliferation of naïve melanocytes following addition of the different CMs described above. Proliferation was measured 14 days after CM addition and normalized to the growth of untreated melanocytes. Error bars represent standard error.

FIG. 3E is a bar graph depicting STAT1 recruitment to the SMARCB1 promoter in SK-MEL-28 cells as measured by ChIP analysis.

FIG. 3F is a pair of bar graphs depicting SMARCB1 (left) or STAT1 (right) mRNA levels in SK-MEL-28 cells following treatment with an NS or STAT1 siRNA, as measured by qRT-PCR.

FIG. 3G is a pair of bar graphs depicting SMARCB1 (left) or BRG1 (right) recruitment to the BNIP3L promoter in SK-MEL-28 cells as measured by ChIP analysis.

FIG. 3H is a line graph depicting apoptosis of SK-MEL-28 cells. SK-MEL-28 cells were incubated with rIGFBP7 for 0, 2, 6, 12, or 24 hours, following which the cells were washed and cultured in medium lacking rIGFBP7. Apoptosis was then quantitated after 24 hours.

FIG. 4A is a set of immunoblots monitoring levels of phospho-ERK and total ERK in SK-MEL-28 cells treated for 24 hours with increasing concentrations of rIGFBP7 (0.2, 1.0, 2.0, 5.0 or 10 μg/ml).

FIG. 4B is a bar graph depicting sensitivity of SK-MEL-28 cells to rIGFBP7. Cells were transfected with an empty expression vector or a constitutively active ERK2 mutant. Cell growth was analyzed 24 hours after treatment with rIGFBP7 and normalized to the growth of the corresponding cell line in the absence of rIGFBP7 addition. Error bars represent standard error.

FIG. 4C is a set of immunoblots monitoring expression of BNIP3L, act-CASP3, phospho-ERK and total ERK in SK-MEL-28 cells stably transfected with an empty expression vector or a constitutively activated ERK2 mutant. SK-MEL-28 cells were either untreated or treated with 10 μg/ml of rIGFBP7, as indicated, for 24 hours prior to harvesting cells.

FIG. 4D is a set of immunoblots monitoring expression of BNIP3L, SMARCB1, act-CASP3, phospho-ERK and total ERK in SK-MEL-28 cells 24 hours following treatment with rIGFBP, a MEK inhibitor (MEK-i) or a RAF inhibitor (RAF-i).

FIG. 5A is a line graph depicting tumor volume of xenografted mice treated locally with rIGFBP7. SK-MEL-28 or SK-MEL-31 cells were injected subcutaneously into the flanks of nude mice, and three, six, and nine days later (arrows), the mice were injected at the tumor site with rIGBP7 or, as a control, PBS. Error bars represent standard error.

FIG. 5B is a line graph depicting tumor volume of xenografted mice treated systemically with rIGFBP7. SK-MEL-28 or SK-MEL-31 cells were injected into the flanks of nude mice. When tumors reached a size of 100 mm$^3$, 100 µg rIGFBP7 was systemically administered by tail vein injection at days 6, 9, and 12 (arrows).

FIG. 5C is a bar graph depicting dose-dependent suppression of tumor growth by rIGFBP7. SK-MEL-28 cells were injected into the flanks of nude mice as described in (FIG. 5B), following which 2, 20, 50, 100, or 250 µg rIGFBP7 was systemically administered by tail vein injection. Tumor volume was measured at day 21 following injection.

FIG. 7A is a polypeptide sequence of human IGFBP7 (SEQ ID NO:1; GenBank Accession No. NP_001544).

FIG. 7B is a nucleotide sequence of human IGFBP7 mRNA (SEQ ID NO:2; GenBank Accession No. NM_001553).

FIG. 8A is a polypeptide sequence of human BRAF (SEQ ID NO:3; GenBank Accession No. NP_004324).

FIG. 8B is a nucleotide sequence of human BRAF mRNA (SEQ ID NO:4; GenBank Accession No. NM_004333)

FIG. 9A is a polypeptide sequence of human NRAS (SEQ ID NO:5; GenBank Accession No. NP_002515).

FIG. 9B is a nucleotide sequence of human NRAS mRNA (SEQ ID NO:6; GenBank Accession No. NM_002524).

FIG. 12B, PBS-control treated; FIG. 12C, IGFBP7 treated.

DETAILED DESCRIPTION

Figure 1A:
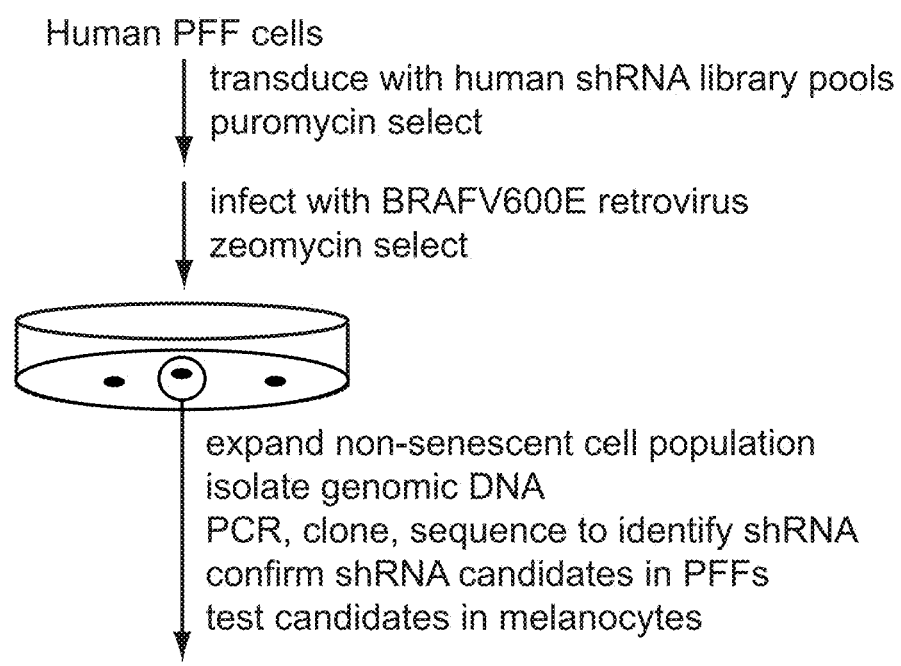
FIG. 1A is a schematic summary of the genome-wide shRNA screen for genes required for the BRAFV600E-mediated block to cellular proliferation.

This disclosure includes methods of treating tumors (e.g., cancers), inducing cellular apoptosis, inducing cellular senescence, and inhibiting cellular proliferation with IGFBP7 agents.

IGFBP7 Agents

IGFBP7 agents that can be used with the methods described herein are agents that include an IGFBP7 polypeptide sequence and, alternatively, one or more polypeptide or non-polypeptide moieties, such that the agent has at least 25% (e.g., at least: 30%; 40%; 50%; 60%; 70%; 75%; 80%; 85%; 90%; 95%; 97%; 98%; 99%; 99.5%, or 100% or even greater) of the ability of rIGFBP7 (see Example 1) to inhibit the proliferation of human BJ primary foreskin fibroblasts in vitro. Exemplary agents include fragments and analogs of IGFBP7 (see below). The IGFBP7 polypeptide sequence can include a mature, soluble IGFBP7 polypeptide (e.g., residues 24 to 282, 25 to 282, 26 to 282, 27 to 282, 28 to 282, or 29 to 282 of SEQ ID NO:1), one or more domains of IGFBP7, or fragments or variants thereof. Exemplary fragments of IGFBP7 include the sequence from residues 84 to 103 of SEQ ID NO:1 (GMECVKSRKRRKGKAGAAAG; SEQ ID NO:7).

In certain embodiments, IGFBP7 polypeptides include sequences substantially identical to all or a portion of a naturally occurring IGFBP7 polypeptide. Polypeptides "substantially identical" to the IGFBP7 polypeptide sequence described herein have an amino acid sequence that is at least 65% (e.g., at least 75%, 80%, 85%, 90%, 95%, 98%, or 99%, e.g., 100%), identical to the amino acid sequences of the IGFBP7 polypeptide represented by SEQ ID NO:1 or SEQ ID NO:7. Furthermore, an IGFBP7 polypeptide with up to 50, e.g., 1, 3, 5, 10, 15, 20, 25, 30, or 40, amino acid insertions, deletions, or substitutions, e.g., conservative amino acid substitutions will be useful in the compositions and methods described herein. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The percent identity between two amino acid sequences can be determined using the BLAST 2.0 program, which is available to the public at ncbi.nlm.nih.gov/BLAST. Sequence comparison is performed using the default parameters (BLOSUM 62 matrix, gap existence cost of 11, per residue gap cost of 1, and a lambda ratio of 0.85). The mathematical algorithm used in BLAST programs is described in Altschul et al., 1997, Nucleic Acids Research, 25:3389-3402.

IGFBP7 polypeptides useful in the methods described herein can be, but are not limited to, recombinant polypeptides and naturally occurring polypeptides. An IGFBP7 polypeptide can be obtained from any human or mammalian species, and include alternatively spliced forms and other isoforms that have the disclosed activities. Non-human IGFBP7 polypeptides with similarity to human IGFBP7 polypeptides have been identified in chimpanzees (e.g., GenBank Accession No. XP_517274), rhesus monkeys (e.g., GenBank Accession Nos. XP_001083041, XP_001082658), cattle (e.g., GenBank Accession No. XP_873466), dogs (e.g., GenBank Accession Nos. XP_850270, XP_861128), mice (e.g., GenBank Accession No. Q61581), and rats (e.g., GenBank Accession No. NP_001013066).

Also useful in the new methods are fusion proteins in which a portion of an IGFBP7 polypeptide is fused to an unrelated polypeptide (e.g., a marker polypeptide or purification tag) to create a fusion protein. For example, the polypeptide can be fused to a peptide tag to facilitate purification (e.g., a hexa-histidine tag or a FLAG tag to facilitate purification of bacterially expressed polypeptides or to a hemagglutinin tag or a FLAG tag to facilitate purification of polypeptides expressed in eukaryotic cells). Also useful are, for example, polypeptides that include a first portion and a second portion; the first portion includes, e.g., an IGFBP7 polypeptide, and the second portion includes, e.g., a detectable marker or a serum protein, e.g., an immunoglobulin constant region, or human serum albumin.

The amino-terminal region of IGFBP7 (up to residue 81 of SEQ ID NO:1) contains a region having homology with other insulin-like growth factor binding proteins (IGFBPs). This region includes conserved cysteine residues at residues 32, 35, 40, 48, 57, 59, 60, 63, 71, and 81 and a conserved "GCGC-CxxC" domain at residues 56 to 63 (see Kim et al., 1997, Proc. Natl. Acad. Sci. 94:12981-86). Other conserved domains of IGFBP7 include a Kazal-type serine protease inhibitors and follistatin-like domain at about residues 118 to 156 (Conserved Domain Database Accession No. cd00104) and an immunoglobulin domain, cell adhesion molecule subfamily, at about residues 160-162 to 248 (Conserved Domain Database Accession No. cd00931). Conserved residues and domains can be used when producing fragments, analogs, and variants of IGFBP7 polypeptides.

An IGFBP7 agent can have one or more chemical modifications (e.g., posttranslational modifications) at one or more sites on the polypeptide, e.g., at the amino or carboxy terminus. Methods of chemical modification are well-known to those of skill in the art, and can be used to alter one or more properties, e.g., activity, stability, retention, or pharmacokinetics of the IGFBP7 agent. Exemplary modifications include glycosylation and PEGylation. IGFBP7 contains a putative N-glycosylation site at residues 171 to 173 of SEQ ID NO:1. Pegylation of IGFBP4 is described in US 2006/0100144. Similar modifications and methods can be used with IGFBP7 agents.

An IGFBP7 agent can also be a peptidomimemtic version of a IGFBP7 polypeptide (e.g., SEQ ID NO:1 or SEQ ID NO:7), functional fragment, or variant thereof. These polypeptides can be modified according to the methods known in the art for producing peptidomimetics. See, e.g., Kazmierski, W. M., ed., *Peptidomimetics Protocols*, Human Press (Totowa N.J. 1998); Goodman et al., eds., *Houben-Weyl Methods of Organic Chemistry: Synthesis of Peptides and Peptidomimetics*, Thiele Verlag (New York 2003); and Mayo et al., *J. Biol. Chem.*, 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include β-amino acids, β-substituted β-amino acids ("β$^3$-amino acids"), phosphorous analogs of amino acids, such as amino phosphonic acids and amino phosphinic acids, and amino acids having non-peptide linkages. Artificial amino acids can be used to create peptidomimetics, such as peptoid oligomers (e.g., peptoid amide or ester analogues), β-peptides, cyclic peptides, oligourea or oligocarbamate peptides; or heterocyclic ring molecules.

Also useful in the methods disclosed herein are nucleic acid molecules that encode IGFBP7 agents described herein, e.g., naturally occurring IGFBP7 polypeptides or forms of IGFBP7 polypeptides in which naturally occurring amino acid sequences are altered or deleted (e.g., fragments or analogs of IGFBP7). Certain nucleic acids can encode polypeptides that are soluble under normal physiological conditions. IGFBP7 agents can be expressed (e.g., exogenously expressed) within a cell by any means known in the art. To generate cells that express IGFBP7 agents, the cells can be transfected, transformed, or transduced using any of a variety of techniques known in the art. Any number of transfection, transformation, and transduction protocols known to those in the art may be used, for example those outlined in Current Protocols in Molecular Biology, John Wiley & Sons, New York. N.Y., or in numerous kits available commercially (e.g., Invitrogen Life Technologies, Carlsbad, Calif.). Such techniques may result in stable or transient transformants. One suitable transfection technique is electroporation, which can be performed on a variety of cell types, including mammalian cells, yeast cells and bacteria, using commercially available equipment. Optimal conditions for electroporation (including voltage, resistance and pulse length) are experimentally determined for the particular host cell type, and general guidelines for optimizing electroporation can be obtained from manufacturers.

Exemplary methods of administering IGFBP7 agents include introducing into a subject a nucleic acid that encodes an IGFBP7 agent described herein. In some embodiments, the nucleic acid that encodes the IGFBP7 agent is contained within a vector, e.g., as a virus that includes a nucleic acid that expresses the IGFBP7 agent. Exemplary viral vectors include adenoviruses (reviewed in Altaras et al., 2005, Adv. Biochem. Eng. Biotechnol., 99:193-260), adeno-associated viruses (reviewed in Park et al., 2008, Front. Biosci., 13:2653-59; see also Williams, 2007, Mol. Ther., 15:2053-54), parvoviruses, lentiviruses, retroviruses (reviewed in Tai et al., 2008, Front. Biosci., 13:3083-95), and the herpes simplex virus. Method of delivery of nucleic acids are reviewed in Patil et al., 2005, AAPS J., 7:E61-77, which is incorporated herein by reference in its entirety.

In some embodiments, a nucleic acid that expresses an IGFBP7 polypeptide is administered directly to cancer cells or to cells in the vicinity of the cancer cells. In some embodiments, a nucleic acid that expresses an IGFBP7 polypeptide is administered to a cell ex vivo, which is then administered to the subject in the vicinity of the tumor.

An IGFBP7 agent can be produced by any means known in the art, e.g., by chemical synthesis, recombinant methods, or isolation from cells that naturally produce IGFBP7. Methods of purification and isolation of molecules that include polypeptides are also well known to those of skill in the art. An exemplary method of purifying IGFBP7 from cultured cells is described in Yamauchi et al., 1994, Biochem J., 303: 591-598.

Production of Fragments and Analogs of IGFBP7

Generation of Fragments

Fragments of a protein can be produced in several ways, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of the mutagenized DNA produces polypeptide fragments. Digestion with "end-nibbling" endonucleases can thus generate DNAs that encode an array of fragments. DNAs that encode fragments of a protein can also be generated by random shearing, restriction digestion or a combination of the above-discussed methods.

Fragments can also be chemically synthesized using techniques known in the art such as conventional Merrifield solid phase f-Moc or t-Boc chemistry. For example, peptides of the present invention can be arbitrarily divided into fragments of desired length with no overlap of the fragments, or divided into overlapping fragments of a desired length.

Generation of Analogs: Production of Altered DNA and Peptide Sequences by Random Methods Amino acid sequence variants of a protein can be prepared by random mutagenesis of DNA which encodes a protein or a particular domain or region of a protein. Useful methods include PCR mutagenesis and saturation mutagenesis. A library of random amino acid sequence variants can also be generated by the synthesis of a set of degenerate oligonucleotide sequences. (Methods for screening proteins in a library of variants are elsewhere herein.)

PCR Mutagenesis

In PCR mutagenesis, reduced Taq polymerase fidelity is used to introduce random mutations into a cloned fragment of DNA (Leung et al., 1989, Technique 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, Science 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins (see, for example, Scott et al. (1990) Science 249:386-390; Roberts et al. (1992) PNAS 89:2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

Generation of Analogs: Production of Altered DNA and Peptide Sequences by Directed Mutagenesis Non-random or directed, mutagenesis techniques can be used to provide specific sequences or mutations in specific regions. These techniques can be used to create variants that include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (Science 244:1081-1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis can be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* (1978) USA, 75: 5765).

Cassette Mutagenesis

Another method for preparing variants, cassette mutagenesis, is based on the technique described by Wells et al. (*Gene* (1985) 34:315). The starting material is a plasmid (or other vector) that includes the protein subunit DNA to be mutated. The codon(s) in the protein subunit DNA to be mutated are identified. There must be a unique restriction endonuclease site on each side of the identified mutation site(s). If no such restriction sites exist, they can be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids that appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening generated mutant gene products. Techniques for screening large gene libraries often include cloning the gene library into replicable expression vectors, transforming appropriate cells with the resulting library of vectors, and expressing the genes under conditions in which detection of a desired activity, e.g., inhibition of human BJ proliferation, is measured. Each of the techniques described below is amenable to high through-put analysis for screening large numbers of sequences created, e.g., by random mutagenesis techniques.

Activating Mutations

The methods and compositions described herein are particularly useful in the treatment of cancers that include cells that have increased Ras-BRAF-MEK-Erk signaling, are dependent for growth and/or survival upon the Ras-BRAF-MEK-Erk signaling pathway, and/or have activating mutations in the BRAF signal transduction pathway (e.g., activating BRAF or RAS (e.g., NRAS, HRAS, or KRAS)) (see, e.g., Dhomen and Marais, 2007, Curr. Opin. Genet. Dev., 17:31-39). BRAF activates the MAP kinase extracellular signal regulated kinase (MEK), which in turn phosphorylates and activates extracellular signal-regulated kinases 1 and 2 (ERK1 and ERK2). Activating BRAF mutations have been found in a majority of melanoma samples tested, as well as in samples from several other types of cancers. Activating RAS mutations have been found in several cancers, including melanoma, multiple myeloma, colorectal cancer, follicular carcinoma, follicular adenoma, leukemia, breast cancer, ovarian cancer, gastric cancer, lung cancer, bladder cancer, pancreatic cancer, lung adenocarcinoma, gall bladder cancer, bile duct cancer, thyroid cancer, and various carcinomas.

An increase in Ras-BRAF-MEK-Erk signaling in a cell can be measured, e.g., by detecting the presence of phosphorylated forms of these proteins in the cell or a cell lysate. Antibodies specific for phosphorylated BRAF, MEK and Erk are commercially available, e.g., from Cell Signaling Technology, Inc. (Danvers, Mass.) and Santa Cruz Biotechnology, Inc. (Santa Cruz, Calif.).

A cell that is dependent for growth and/or survival upon the Ras-BRAF-MEK-Erk signaling pathway will display reduced growth and/or survival when the expression or activity of a component of the Ras-BRAF-MEK-Erk pathway is artificially inhibited, e.g., by pharmacologic (e.g., the farnesyltransferase inhibitor R115777, the MEK1/2 inhibitor PD184352, the MEK inhibitor U0216 (Cell Signaling), the MEK inhibitor PD98054 (Calbiochem), the RAF inhibitor GW5074 (Sigma), BAY 43-9006, CI-1040, hypothemycin, or PD0325901) (Solit et al., 2006, Nature, 439:358-362; Alessi et al., 1995, J. Biol. Chem., 270:27489-94) or genetic means (e.g., transfection with dominant-negative Ras, MEK1 shRNA, or an inhibitory nucleotide against a component of the pathway).

Activated BRAF proteins have one or more of the following properties: elevated kinase activity, increased signaling to ERK in vivo or in vitro, transformation of NIH 3T3 cells, and decreased proliferation of human foreskin fibroblasts (e.g., BJ fibroblasts or primary foreskin fibroblasts). Exemplary activating BRAF point mutations include substitution of Val600 with Glu (V600E; caused by, e.g., a T→A transversion at nucleotide 1799 of the BRAF coding sequence), substitution of Arg462 with Ile (R462I; caused by, e.g., a G→T transversion at nucleotide 1385 of the BRAF coding sequence), substitution of Ile463 with Ser (I463S; caused by, e.g., a T→G transversion at nucleotide 1388 of the BRAF coding sequence), substitution of Gly464 with Glu (G464E;

caused by, e.g., a G→A transition at nucleotide 1391 of the BRAF coding sequence), substitution of Lys601 with Glu (K601E; caused by, e.g., an A→G transition at nucleotide 1801), substitution of Gly465 with Val (G465V), substitution of Leu596 with Arg (L596R) or Val (L596V), substitution of Gly468 with Arg (G468R) or Ala (G468A), and substitution of Asp593 with Gly (D593G). Activating BRAF mutations caused by chromosomal rearrangements have also been identified. For example, a fusion of the AKAP9 and BRAF proteins has been reported, caused by an inversion of chromosome 7q, resulting in an in-frame fusion between exons 1-8 of the AKAP9 gene and exons 9-18 of BRAF (Clampi et al., 2005, J. Clin. Invest., 115:94-101).

Activated RAS proteins have one or more of the following properties: increased signaling to RAF (e.g., BRAF) in vivo or in vitro, transformation of NIH 3T3 cells, and decreased proliferation of human foreskin fibroblasts (e.g., BJ fibroblasts of primary foreskin fibroblasts). Exemplary activating NRAS point mutations include substitution of Gly13 with Arg (G13R, caused by a G→C mutation at codon 13) and substitution of Gln61 with Arg (Q61R, caused by a CAA→CGA mutation at codon 61). See also Bos et al., 1985, Nature, 315:726-730; Davis et al., 1984, Cytogenet. Cell Genet., 37:448-449; Taparowsky et al., 1983, Cell, 34:581-586; Yuasa et al., 1984, Proc. Nat. Acad. Sci. USA, 81:3670-74). Exemplary activating HRAS point mutations include substitution of Gly12 with Val (G12V, caused by a GGC→GTC mutation at codon 12) and substitution of Gln61 with Lys (Q61K, caused by a CAG→AAG mutation at codon 61). Exemplary activating KRAS point mutations include substitution of Gly12 with Cys (G12C, caused by a G→T transversion at nucleotide 34), substitution of Gly 12 with Arg (G12R, caused by a G→C transversion at codon 12), substitution of Gly13 with Asp (G13D, caused by a G→A transition at codon 13), substitution of Ala59 with Thr (A59T, caused by a G→A transition at codon 59), substitution of Gly12 with Asp (G12D), substitution of Gly12 with Val (G12V), substitution of Gly12 with Ser (G12S, caused by a G→A transition at codon 12), insertion of Gly11 (G11-INS, caused by a 3-bp insertion in exon 1), and substitution of Gly13 with Arg (G13R, caused by a G→C transversion at codon 13).

Constitutively activated ERK mutants include ERK2Q103A and ERK2L73P,S151D (Emrick et al., 2006, Proc. Natl. Acad. Sci. USA, 103:18101-06; Emrick et al., 2001, J. Biol. Chem., 276:46469-79). An exemplary activated MEK1 mutant is MEK1EE (Tournier et al., 1999, Mol. Cell Biol., 19:1569-81).

Activating BRAF, RAS, ERK, or MEK mutations can be detected by assaying for the presence of mutant nucleic acids in a sample from the subject. An exemplary, commercially available assay to detect BRAF mutations is the Mutector® mutation detection kit (Trimgen, Sparks, Md.; Cat. Nos. GP04, MH1001-01, MH1001-02, MH1001-03, MH1001-04) (Xing et al., 2004, Clin. Endocrinol. Metab., 89:2867-72; Ichii-Nakato et al., 2006, J. Invest. Dermatol., 126:2111-18). An exemplary, commercially available assay to detect KRAS mutations is available from DxS Ltd. (Manchester, UK).

Other exemplary methods of detecting mutant nucleic acids include direct sequencing; restriction fragment analysis (Cohen et al., 2003, Invest. Ophthalmol. Vis. Sci., 44:2876-78); single-strand conformation polymorphism gel electrophoresis (Lee et al., 2003, Br. J. Cancer., 89:1958-60); site-directed mutagenesis/restriction analysis (Alsina et al., 2003, Clin. Cancer Res., 9:6419-25; Goydos et al., 2005, J. Am. Coll. Surg., 200:362-370); sequence-specific PCR (Deng et al., 2004, Clin. Cancer Res., 10:191-195); real-time polymerase chain reaction and melting curve analysis (Ikenoue et al., 2004, Cancer Genet. Cytogenet., 149:68-71); gap ligase chain reaction (Goldenberg et al., 2004, Mod. Pathol., 17:1386-91); mutant allele specific PCR amplification (MASA) (Lilleberg et al., 2004, Ann. NY Acad. Sci., 1022:250-256; Sapio et al., 2006, Eur. J. Endocrinol., 154:341-348); allele-specific PCR (Burger et al., 2006, Eur. Urol., 50:1102-09); real-time allele-specific PCR (Jarry et al., 2004, Mol. Cell. Probes., 18:349-352; Yancovitz et al., 2007, J. Mol. Diagn., 9:178-183); PCR-restriction fragment length polymorphism (RFLP) analysis (Hayashida et al., 2004, Thyroid, 14:910-915; Chung et al., 2006, Clin. Endocrinol. (Oxf.), 65:660-666); mismatch ligation assay (Busby and Morris, 2005, J. Clin. Pathol., 58:372-375); ligase detection reaction (Turner et al., 2005, J. Cutan. Pathol., 32:334-339); high-resolution amplicon melting analysis (Willmore-Payne et al., 2005, Hum. Pathol., 36:486-493); denaturant capillary electrophoresis (Hinselwood et al., 2005, Electrophoresis, 26:2553-61); loop-hybrid mobility shift assay (Matsukuma et al., 2006, J. Mol. Diagn., 8:504-512); single-base extension analysis (Kann et al., 2006, Clin. Chem., 52:2299-2302); oligonucleotide microarray (Kim et al., 2007, J. Mol. Diagn., 9:55-63); in situ hybridization; in situ amplification; and other known means of detecting nucleotide polymorphisms, e.g., single nucleotide polymorphisms. See also US 2006/0246476, US 2006/0252041, US 2007/0020657, and US 2007/0087350. In some embodiments, the presence or absence of several mutant nucleic acids is assayed (e.g., sequentially or simultaneously).

Activating BRAF, RAS, ERK, or MEK mutations can also be detected by assaying for the presence of mutant proteins. Exemplary methods for detecting mutant proteins include immunological methods using mutation-specific antibodies (Fensterle et al., 2004, BMC Cancer, 4:62; Kawakami et al., 2005, Cancer Metastasis Rev., 24:357-66); arrays containing mutation-specific antibodies; and mass spectrometry (e.g., MS/MS or MALDI-TOF mass spectrometry) (Powell et al., 2005, J. Pathol., 205:558-64). In some embodiments, the presence or absence of several mutant proteins is assayed (e.g., sequentially or simultaneously).

Activating BRAF, RAS, ERK, or MEK mutations can also be detected by assaying a sample for BRAF or RAS activity (see, e.g., US 2006/0211073). Alternatively, the presence of an activating BRAF, RAS, ERK, or MEK mutation can be inferred by detecting a characteristic pattern of gene expression generated by the mutant protein.

A sample from a subject can be of any type without limitation, including a biopsy, aspirate, blood, plasma, lymph, urine, saliva, or other bodily fluid. The sample will often include cells of the subject, e.g., cells from a tumor, lesion, or suspected cancerous tissue of the subject. However, many of the detection methods described herein are sensitive enough to detect traces of mutant nucleic acids or proteins in a cell-free sample, even in the presence of the corresponding wild-type nucleic acids or proteins. A sample containing cells can be fixed or otherwise processed prior to assaying.

Cancer Diagnostics

The diagnosis of certain cancers (e.g., cancers with activated BRAF or RAS) can be accomplished by testing a sample (e.g., one or more cells) from a suspected tumor for expression of IGFBP7. A sample that has increased Ras-BRAF-MEK-Erk signaling, is dependent for growth and/or survival upon the Ras-BRAF-MEK-Erk signaling pathway, and/or contains an activated BRAF or RAS and does not substantially or detectably express IGFBP7 (e.g., as compared to a sample from a non-cancerous cell or tissue from the subject or a reference value (e.g., obtained from normal cell or tissue samples)) is diagnosed as cancerous. Likewise, a sample that does not have increased Ras-BRAF-MEK-Erk signaling, is not dependent for growth and/or survival upon the Ras-BRAF-MEK-Erk signaling pathway, and/or does not contain an activated BRAF or RAS and does not substantially or detectably express IGFBP7 (e.g., as compared to a sample from a non-cancerous cell or tissue from the subject or a reference value (e.g., obtained from normal cell or tissue samples)) can be diagnosed as cancerous.

The diagnostic methods described herein can be used for lesions or suspected tumors of any organ or tissue. When the organ or tissue is skin, the sample can contain melanocytic cells. Melanocytic cells that have increased Ras-BRAF-MEK-Erk signaling, are dependent for growth and/or survival upon the Ras-BRAF-MEK-Erk signaling pathway, and/or contain an activated BRAF or RAS and substantially express IGFBP7 are diagnosed as melanocytic nevi (moles); melanocytic cells that have increased Ras-BRAF-MEK-Erk signaling, are dependent for growth and/or survival upon the Ras-BRAF-MEK-Erk signaling pathway, and/or express activated BRAF or RAS, but do not substantially express IGFBP7 are diagnosed as melanoma. Melanocytic cells that do not have increased Ras-BRAF-MEK-Erk signaling, are not dependent for growth and/or survival upon the Ras-BRAF-MEK-Erk signaling pathway, and/or do not contain an activated BRAF or RAS but do substantially or detectably express IGFBP7 are also diagnosed as melanoma. The assays can be used with tissue sections (e.g., frozen tissue sections), and are therefore useful for histological analysis and clinical diagnosis. The methods do not require a particular method of tissue fixation, as the assay works with unfixed cells or tissue or with several kinds of fixatives, e.g., methanol/acetone fixation, or formaldehyde fixation. The assay can work with paraffin sections, e.g., renatured paraffin sections. Other useful tissue fixation methods are known to one of ordinary skill in the art.

Methods for detecting expression of IGFBP7 in a sample include detecting mRNA or cDNA and detecting protein, e.g., using an antibody or other binding protein, or using an activity assay. It is also possible to detect IGFBP7 mRNA or cDNA using any of a variety of molecular techniques, including RT-PCR and microarray analysis.

Examples of methods of gene expression analysis known in the art include DNA arrays or microarrays (Brazma and Vilo, FEBS Lett., 2000, 480, 17-24; Celis et al., FEBS Lett., 2000, 480, 2-16), SAGE (serial analysis of gene expression) (Madden et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe et al., Proc. Natl. Acad. Sci. USA, 2000, 97, 1976-81), protein arrays and proteomics (Celis et al., FEBS Lett., 2000, 480, 2-16; Jungblut et al., Electrophoresis, 1999, 20, 2100-10), expressed sequence tag (EST) sequencing (Celis et al., FEBS Lett., 2000, 480, 2-16; Larsson et al., J. Biotechnol., 2000, 80, 143-57), subtractive RNA fingerprinting (SuRF) (Fuchs et al., Anal. Biochem., 2000, 286, 91-98; Larson et al., Cytometry, 2000, 41, 203-208), subtractive cloning, differential display (DD) (Jurecic and Belmont, Curr. Opin. Microbiol., 2000, 3, 316-21), comparative genomic hybridization (Carulli et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (reviewed in To, Comb. Chem. High Throughput Screen, 2000, 3, 235-41).

Cancers

The new methods can be used to diagnose and treat several types of cancer, e.g., melanomas, thyroid cancers (e.g., papillary thyroid carcinoma, anaplastic thyroid carcinoma, follicular carcinoma, follicular adenoma), colorectal cancers, lung cancers (e.g., adenocarcinoma, nonsmall cell lung cancer), lymphomas (e.g., non-Hodgkin lymphoma), multiple myeloma, leukemias, breast cancers, ovarian cancers, gastric cancers, bladder cancers, pancreatic cancers, gall bladder cancers, bile duct cancers, and other carcinomas. Methods of diagnosing cancers are well known to those of skill in the art. In some embodiments, the new methods can be useful for any type of tumor, cancer, or neoplasm that has increased Ras-BRAF-MEK-Erk signaling, is dependent for growth and/or survival upon the Ras-BRAF-MEK-Erk signaling pathway, and/or contains an activated or oncogenic BRAF or RAS.

Pharmaceutical Formulations

The IGFBP7 agents described herein (all of which can be referred to herein as "active compounds"), can be incorporated into pharmaceutical compositions. Such compositions typically include the active compound and a pharmaceutically acceptable carrier or excipient. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

There are a number of methods by which the new compositions for use in the new methods can be delivered to subjects, in general, and to specific cells or tissue in those subjects, in particular. For example, an IGFBP7 agent described herein can be injected into a subject or a tissue of the subject. In another example, a vector (e.g., a plasmid or virus) encoding an IGFBP7 agent can be introduced into a cell or tissue of the subject. The vector would then enter the cell or cells in that tissue and express the IGFBP7 agent. Delivery specificity of such plasmids can be enhanced by associating them with organ- or tissue-specific affinity, so that they preferentially enter specified cell types. However, because IGFBP7 can act extracellularly, it is not necessary to deliver the vector directly to tumor cells. The vector can be delivered to the tissue surrounding the tumor. Methods of expressing proteins for tumor therapy are described, e.g., in Cross and Burmester, 2006, Clin. Med. Res., 4:218-227; Lejuene et al., 2007, Expert Rev. Anticancer Ther. 7:701-713; and Bloquel et al., 2004, J. Gene Med., 6:S11-S23.

Compounds and their physiologically acceptable salts and solvates can be formulated for oral, topical, buccal, parenteral or rectal administration or administration by inhalation or insufflation (either through the mouth or the nose).

The compounds will generally be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, for example, sterile pyrogen-free water, before use. Where the compositions are intended for use in a specific treatment area, the compositions can be administered by one or more local injections into the tumor site to diminish as much as possible any side effects relating to the compound's activities outside of the treatment area.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt. A depot preparation can include embedded or encapsulated cells or tissue that secrete an IGFBP7 agent, which can be administered, e.g., by implantation or by intramuscular injection.

The compositions can, if desired, be presented in a pack or dispenser device that can contain one or more unit dosage forms containing the active ingredient. The pack can, for example, include metal or plastic foil, such as a blister pack. The pack or dispenser device can be accompanied by instructions for administration.

The therapeutic compositions of the invention can also contain a carrier or excipient, many of which are known to skilled artisans. Methods for making such formulations are well known and can be found in, for example, Remington: The Science and Practice of Pharmacy, University of the Sciences in Philadelphia (USIP), 2005.

The compositions can also be formulated for intracellular delivery of the active compounds, using methods known in the art. For example, the compositions can include liposomes or other carriers that deliver the active compound across the plasma membrane. Vesicles that are covered with membrane-permeant peptides, such as Tat or Antennapedia, can also be used. A number of other methods for enhancing intracellular delivery are familiar to those of skill in the art.

It is recognized that the pharmaceutical compositions and methods described herein can be used independently or in combination with one another. That is, subjects can be administered one or more of the pharmaceutical compositions, e.g., pharmaceutical compositions that include an IGFBP7 agent, subjected to one or more of the therapeutic methods described herein, or both, in temporally overlapping or non-overlapping regimens. When therapies overlap temporally, the therapies can generally occur in any order and can be simultaneous (e.g., administered simultaneously together in a composite composition or simultaneously but as separate compositions) or interspersed. By way of example, a subject afflicted with a disorder described herein can be simultaneously or sequentially administered both a cytotoxic agent which selectively kills aberrant cells and an antibody (e.g., an antibody of the invention) which can, in one embodiment, be conjugated or linked with a therapeutic agent, a cytotoxic agent, an imaging agent, or the like.

Effective Doses

Toxicity and therapeutic efficacy of an IGFBP7 agent can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Inhibitors that exhibit large therapeutic indices are preferred. While inhibitors that exhibit toxic side effects can be used, care can be taken to design a delivery system that targets such compounds to the site of affected tissue to minimize potential damage to non-target cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the new methods, the therapeutically effective dose can be estimated initially from cell culture assays. A dose can also be calculated in animal models to achieve a circulating plasma concentration range that includes the IC50 (that is, the concentration of the test compound which achieves a half-maximal inhibition of symptoms) as determined in cell culture. Such information can be used to more accurately determine useful doses in humans.

EXAMPLES

Materials and Methods

Cell Lines and Culture

Primary foreskin fibroblasts (BJ) and human melanoma cell lines were obtained from ATCC and grown in Dulbecco's modified Eagle's medium supplemented with 10% fetal calf serum at 37° C. under 5% $CO_2$. Human primary melanocytes were obtained from Cascade Biologics and grown as per the supplier's recommendation.

Retroviruses and Plasmids

Retroviruses expressing empty vector or BRAFV600E were generated from plasmids pBABE-zeo (Addgene) and pBABE-zeo/BRAFV600E (Michaloglou et al., 2005, Nature, 436:720-724). Plasmids expressing constitutively activated ERK2 mutants ERK2Q103A and ERK2L73P,S151D (Emrick et al., 2006, Proc. Natl. Acad. Sci. USA, 103:18101-06; Emrick et al., 2001, J. Biol. Chem., 276:46469-79) and MEK1 mutant MEK1EE (Tournier et al., 1999, Mol. Cell Biol., 19:1569-81) were also obtained.

shRNA Screen

The human shRNA$^{mir}$ library (release 1.20; Open Biosystems) was obtained through the University of Massachusetts Medical School shRNA library core facility. Ten retroviral pools, each comprising ~6000 shRNA clones, were generated with titers of ~$2.6 \times 10^5$ pfu/ml. These retroviral stocks were produced following co-transfection into the PhoenixGP™ packaging cell line (Grignani, 1998, Cancer Res., 58:14-19). PFF fibroblasts ($1.2 \times 10^6$) were transduced at an MOI of 0.2 with the retroviral stocks in 100 mm plates, and 2 days later were selected for resistance to puromycin (1.5 μg/ml) for 7 days. Cells were then infected with a retrovirus carrying BRAFV600E under conditions in which all cells were infected (MOI 20). Cells that bypassed the BRAFV600E-induced cellular proliferation block formed colonies, which were pooled and expanded, and the shRNAs identified by sequence analysis. To identify the candidate shRNAs, the shRNA region of the transduced virus was PCR amplified (using primers PSM2-forward, 5'-GCTCGCTTCGGCAG-CACATATAC-3' (SEQ ID NO:8) and PSM2-reverse, 5'-GAGACGTGCTACTTCCATTTGTC-3' (SEQ ID NO:9)) and cloned into pGEM-T Easy (Promega). An average of 48 clones were sequenced per pool (using primer PSM2-seq, 5'-GAGGGCCTATTTCCCATGAT-3' (SEQ ID NO:10)). Individual PFF or melanocyte knockdown cell lines were generated by stable transduction of $6 \times 10^4$ cells with single shRNAs directed against the candidate gene, followed by infection with the BRAFV600E-expressing retrovirus. Individual shRNAs were either obtained from the Open Biosystems library or synthesized.

Quantitive Real-Time RT-PCR

Total RNA was isolated using TRIZOL™ (Invitrogen) 7 days after retroviral transduction and puromycin selection. Reverse transcription was performed using SuperScript™ II Reverse Transcriptase (Invitrogen) as per the manufacturer's instructions, followed by quantitative real-time PCR using Platinum SYBR™ Green qPCR SuperMix-UDG with Rox (Invitrogen).

Proliferation Assay

Figure 1B:
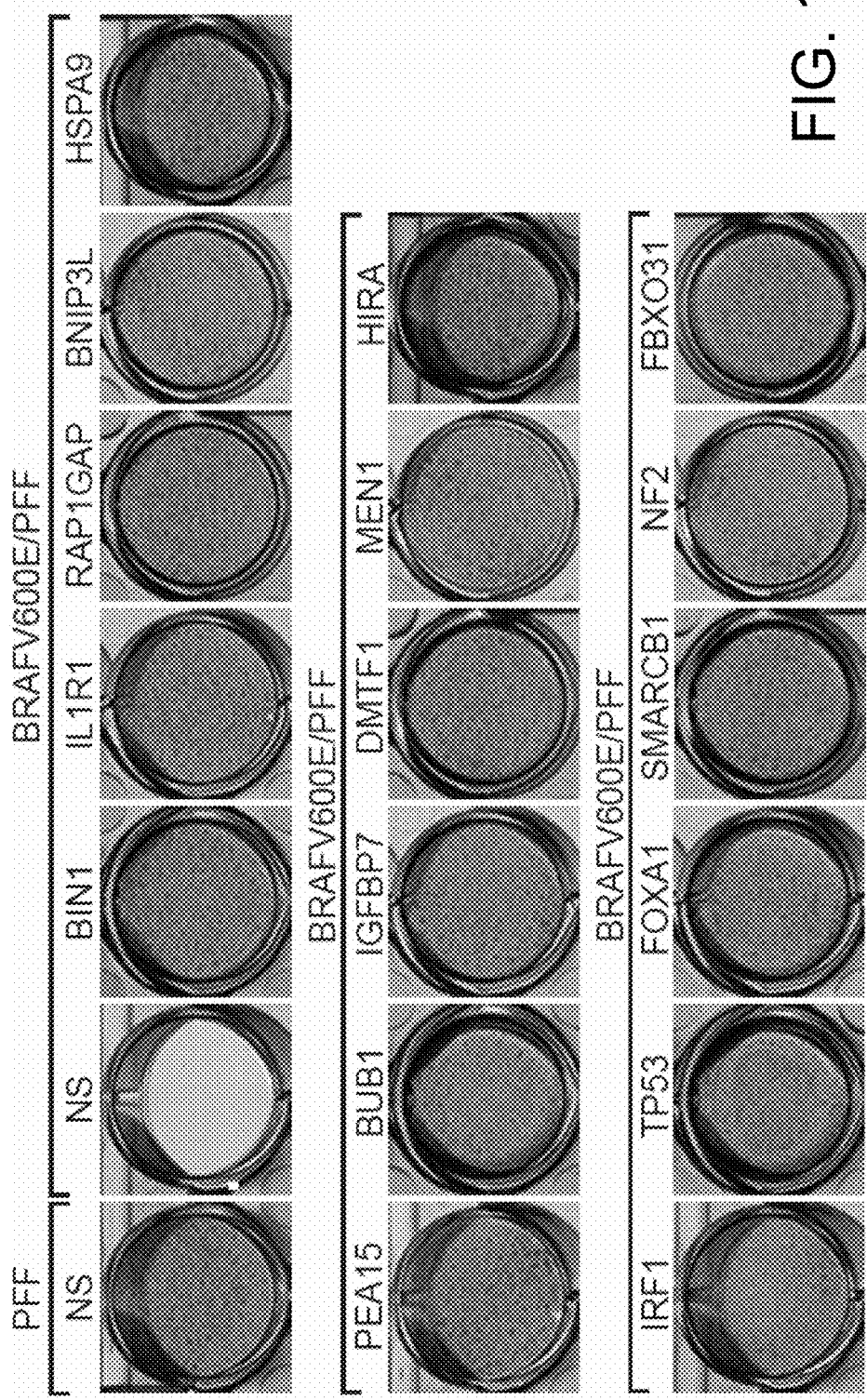
FIG. 1B is a set of representations of photographs depicting proliferation of the 17 BRAFV600E/BJ KD cell lines. 1×10$^4$ BJ fibroblasts stably expressing the indicated shRNA were cultured in 12-well plate format, infected with the BRAFV600E-expressing retrovirus, and after 14 days stained with crystal violet. NS, non-silencing control shRNA.

For the proliferation assay shown in FIG. 1B, $1\times10^4$ cells stably expressing an shRNA were cultured in 12-well plate format, infected with BRAFV600E-expressing retrovirus and after 14 days stained with crystal violet. For all other quantitative proliferation assays, cell viability was measured by trypan blue exclusion test at the time point indicated in the relevant figure legend. Values were expressed as percent cell growth, as described in the relevant figure legend. For the proliferation assays shown in FIG. 2A, CM was replenished every 3 days, and proliferation was measured after a total of 14 days of CM treatment. Unless otherwise stated, rIGFBP7 was added to the culture medium at a concentration of 10 μg/ml.

Apoptosis Assay

PFF fibroblasts or melanocytes or shRNA knockdown derivatives ($5\times10^5$ cells) were infected with BRAFV600E-expressing retrovirus, and 4 days later the total cell population was stained for Annexin V-PE (BD Biosciences). To monitor apoptosis in melanoma cells following rIGFBP7 treatment, $5\times10^5$ cells were treated with rIGFBP7 (10 μg/ml) for 24 hours and stained for Annexin V-PE.

DNA Replication Assay

PFF fibroblasts or melanocytes or shRNA knockdown derivatives ($5\times10^5$ cells) were infected with BRAFV600E-expressing retrovirus, and ~4 days later the total cell population was stained for BrdU incorporation. Briefly, 4 hours prior to the end of the 4-day infection with BRAFV600E-expressing retrovirus, cells were incubated with 20 μM BrdU (Sigma) to allow for BrdU incorporation, at which point cells were fixed in 70% ethanol, permeabilized using 0.2% Triton™ X-100, treated with 2N HCl, and probed using an a-BrdU antibody (Ab-3, Oncogene) which was then detected using an anti-mouse IgG Texas Red-conjugated antibody (Calbiochem).

Antibodies and Immunoblot Analysis

To prepare cell extracts, cells were lysed in Laemmli buffer; for phospho-proteins, cells were lysed in the presence of a phosphatase inhibitor cocktail (Sigma). To prepare conditioned media, cells were grown in Opti-MEM™ (Invitrogen) for 24 hours, and media was harvested and concentrated using Centricon™ plus 20 tubes (Millipore). Conditioned media was normalized to cell number prior to loading the gel. For the experiments shown in FIGS. 3D and 4C, rIGFBP7 was added to the culture medium at a concentration of 10 μg/ml. For the MEK/RAF inhibitor experiment of FIG. 4D, SK-MEL-28 cells were treated with 2 μg/ml or 10 μg/ml rIGFBP7, 20 μM or 40 μM of the MEK inhibitor PD98054 (Calbiochem), or 5 nM or 10 nM the RAF inhibitor GW5074 (Sigma) for 24 hours prior to harvesting cells. Proteins were resolved by SDS-PAGE and transferred to nitrocellulose. Blots were probed with the following antibodies: α-p16 (Abcam), α-acetylated H3K9 (Upstate), α-IGFBP7 (Santa Cruz), α-SMARCB1 (Abnova), α-BNIP3L (Proscience), α-BRAFV600E (Santa Cruz), α-cleaved caspase-3 p11 (Santa Cruz), α-β-actin (Sigma), α-phospho-ERK (Cell Signaling) or α-ERK (Cell Signaling).

Recombinant IGFBP7 Expression and Purification

The human IGFBP7 expression vector pFASTBAC-1/IGFBP7, expressing a C-terminal Flag-tagged fusion protein (Oh, et al., 1996, J. Biol. Chem., 271:30322-25), was used to generate recombinant baculovirus using the Bac-to-Bac™ Baculovirus Expression System (Invitrogen) as per the manufacturer's instructions. The recombinant baculovirus construct was then transfected into Sf9 cells (Invitrogen) for baculovirus production, and amplified to produce recombinant IGFBP7 protein. Conditioned media from IGFBP7-expressing Sf9 cells was collected and incubated with α-Flag M2 beads (Sigma), and the bound protein was eluted using an α-Flag peptide.

Senescence-Associated β-Galactosidase Assay

Melanocytes infected with a retrovirus expressing either vector or BRAFV600E, or melanocytes treated with BRAFV600E/melanocyte CM or rIGFBP7 (10 μg/ml) for 14 days were washed twice with PBS (5 minutes at room temperature), fixed with 3% formaldehyde (5 minutes at room temperature), and washed three more times with PBS. Cells were then incubated at 37° C. (0% $CO_2$) overnight in SA-β-Gal stain solution (1 mg/mL X-Gal (5-bromo-4-chloro-3-indoyl b-D-galactoside), 40 mM citric acid/sodium phosphate (pH 6.0), 5 mM potassium ferrocyanide, 5 mM potassium ferricyanide, 150 mM NaCl and 2 mM $MgCl_2$). Cells were washed with PBS and visualized on a Zeiss Axiovert™ 40 CFL microscope. Images were captured using QCapture™ Pro version 5 software (QImaging Corporation).

ChIP Assays

Chromatin immunoprecipitation (ChIP) assays were performed using extracts prepared 24 hours following rIGFBP7 treatment. The following antibodies were used: α-BRG1 (de La Serna et al., 2000, Mol. Cell. Biol., 20:2839-51), α-phospho-STAT1 (Upstate), and α-SMARCB1 and α-STAT1 (Santa Cruz). For ChIP experiments on the SMARCB1 promoter, primers spanning a STAT1 binding site located ~2.4 kb upstream of the transcription start-site were used. For ChIP experiments on the BNIP3L promoter, a series of primer-pairs that covered ~2 kb of the BNIP3L promoter were used; following addition of rIGFBP7, SMARCB1 and BRG1 were recruited to the BNIP3L promoter near the transcription start-site. ChIP products were analyzed by quantitative real-time PCR using Platinum SYBR™ Green qPCR SuperMix-UDG with Rox (Invitrogen). Calculation of fold differences was done as previously described (Pfaffl, 2001, Nucleic Acids Res., 29:e45).

Tumor Formation Assays $5\times10^6$ SK-MEL-28 or SK-MEL-31 cells were suspended in 100 μl of serum-free DMEM and injected subcutaneously into the right flank of athymic Balb/c (nu/nu) mice (Taconic). Three, six, and nine days later, the mice were injected at the tumor site with either 20 μg of rIGBP7 in a total volume of 100 μl or, as a control, PBS. Tumor dimensions were measured every three days and tumor volume was calculated using the formula $\pi/6\times(length)\times(width)^2$. For the systemic administration experiments, $5\times10^6$ SK-MEL-28 or SK-MEL-31 cells were injected into the flanks of nude mice and when tumors reached a size of 100 mm3, 100 μg rIGFBP7 in a total volume of 100 μl was delivered by tail vein injection at days 6, 9, and 12. Tumor dimensions were measured every three days. Animal experiments were performed in accordance with the Institutional Animal Care and Use Committee (IACUC) guidelines.

Immunohistochemistry

The study was approved by the UMass Medical Center institutional review board. Archival materials from normal skin (n=5), nevi (n=20) and malignant melanoma (primary (n=7) and metastatic (n=13)) were retrieved from the pathology files of UMass Medical Center, Worcester, Mass. The histologic sections of all cases were re-reviewed and the diagnoses confirmed by a dermatopathologist. All patient data were de-identified.

Five-micron thick sections were cut for immunohistochemical studies, which were performed using standard techniques with heat-induced epitope retrieval buffer and primary antibodies against IGFBP7 (1:20 dilution; Santa Cruz). Appropriate positive and negative controls were included.

Positive staining was noted by ascertaining expression of IGFBP7 in the cytoplasm. Significant nuclear staining was not noted. All stained slides were reviewed by the dermatopathologist. Genomic DNA for genotyping was isolated from ten 10 μm-thick sections using ISS buffer (20×SSC pH 7.0, 3 M NaCl, 0.3 M sodium citrate, 1M NaCl, and 10% SDS) plus 40 μl/ml of 20 mg/ml proteinase K and 4 μl/ml of 0.1 M DTT. Briefly, tissue samples were scraped from the slides and incubated in ISS buffer with proteinase K and DTT overnight at 61° C. The following day, samples were extracted twice with phenol-chloroform, the second round using Phase Lock Gel (Eppendorf), and the samples were then precipitated using ethanol. Genomic DNA was quantitated and its integrity checked by gel electrophoresis, followed by PCR amplification and TA cloning (Promega). Multiple clones were sequenced for identifying the V600E mutation (T1796A) in exon 15 of the BRAF gene (primers: Forward primer: 5'-TCATAATGCTTGCTCTGATAGGA-3' (SEQ ID NO:11), Reverse primer: 5'-GGCCAAAATTTAATCAGTGGA-3' (SEQ ID NO:12)).

Bisulfite Sequencing

Bisulfite modification was carried out essentially as described (Frommer et al., 1992, Proc. Natl. Acad. Sci. USA, 89:1827-31), except that hydroquinone was used at a concentration of 125 mM during bisulfite treatment (carried out in the dark) and DNA was desalted on QIAQUICK™ columns (Qiagen) after the bisulfite reaction. Six clones were sequenced for each cell line or human tissue sample. For 5-aza-2'-deoxycytidine (5-aza) treatment, melanoma cell lines were treated with 10 μM 5-aza (Calbiochem) for 48 hours.

Example 1

A Genome-Wide shRNA Screen Identifies Factors Required for BRAFV600E-Mediated Senescence and Apoptosis To identify genes required for BRAFV600E to block proliferation of primary cells, a genome-wide small hairpin RNA (shRNA) screen was performed (shown schematically in FIG. 1A). The primary screen was performed in human primary foreskin fibroblasts (PFFs). A human shRNA library comprising ~62,400 shRNAs directed against ~28,000 genes was divided into 10 pools, which were packaged into retrovirus particles and used to stably transduce PFFs. The cells were then infected with a retrovirus expressing BRAFV600E under conditions in which all cells were infected. Cells that bypassed the BRAFV600E-mediated cellular proliferation block formed colonies, which were pooled and expanded, and the shRNAs were identified by sequence analysis. Positive candidates were confirmed by stable transduction of PFFs with single shRNAs directed against the candidate genes, infection with the BRAFV600E-expressing retrovirus, and quantitation of cellular proliferation. Confirmed candidate shRNAs were then tested in a secondary screen for their ability to bypass the proliferation block in BRAFV600E-expressing primary human melanocytes.

The screen identified 17 genes that, following shRNA-mediated knockdown, enabled BRAFV600E-expressing PFFs (BRAFV600E-PFFs) and melanocytes (BRAFV600E-melanocytes) to proliferate. These genes are listed in Table 1, and proliferation assays of the 17 BRAFV600E-PFF knockdown (KD) cell lines are shown in FIG. 1B. As expected from previous studies (Zhu et al., 1998, Genes Dev., 12:2997-3007), expression of BRAFV600E in PFFs for in PFFs containing a control non-silencing (NS) shRNA (BRAFV600E-PFF-NS) efficiently inhibited cellular proliferation (FIG. 1B). Significantly, however, this block was overcome in all 17 BRAFV600E-PFF KD cell lines. Quantitative real-time RT-PCR (qRT-PCR) confirmed in all cases that expression of the target gene was decreased in the corresponding PFF and melanocyte KD cell lines. For all 17 genes, a second, unrelated shRNA directed against the same target gene also enabled PFFs to proliferate following BRAFV600E expression.

TABLE 1

Genes required for BRAFV600E-induced block to cellular proliferation

| BIOLOGICAL PROCESS | ACCESSION NUMBER | GENE SYMBOL | NAME |
|---|---|---|---|
| Apoptosis | NM_004331 | BNIP3L | BCL2/adenovirus E1B 19 kDa interacting protein 3-like |
| Cell cycle regulation | NM_004336 | BUB1 | budding uninhibited by benzimidazoles 1 homolog (yeast) |
| Signal transduction | NM_004305 | BIN1 | bridging integrator 1 |
| | NM_004134 | HSPA9 | heat shock 70 kDa protein 9 (mortalin) |
| | NM_001553 | IGFBP7 | insulin-like growth factor binding protein 7 |
| | NM_000877 | IL1R1 | interleukin 1 receptor, type 1 |
| | NM_003768 | PEA15 | phosphoprotein enriched in astrocytes 15 |
| | NM_002885 | RAP1GAP | RAP1 GTPase activating protein |
| Transcription regulation | NM_021145 | DMTF1 | cyclin D binding myb-like transcription factor 1 |
| | NM_004496 | FOXA1 | Forkhead box A1 |
| | NM_002198 | IRF1 | interferon regulatory factor 1 |
| | NM_000244 | MEN1 | multiple endocrine neoplasia 1 |
| | NM_000546 | TP53 | tumor protein p53 (Li-Fraumeni syndrome) |
| Chromatin remodeling | NM_001007468 | SMARCB1 | SWI/SNF related, matrix associated, actin dependent regulator of chromatin, subfamily b, member 1 |
| | NM_003325 | HIRA | HIR histone cell cycle regulation defective homolog A (S. cerevisiae) |
| Genome stability | NM_000268 | NF2 | neurofibromin 2 (bilateral acoustic neuroma) |
| Unknown | NM_024735 | FBXO31 | F-box protein 31 |

Figure 1C:
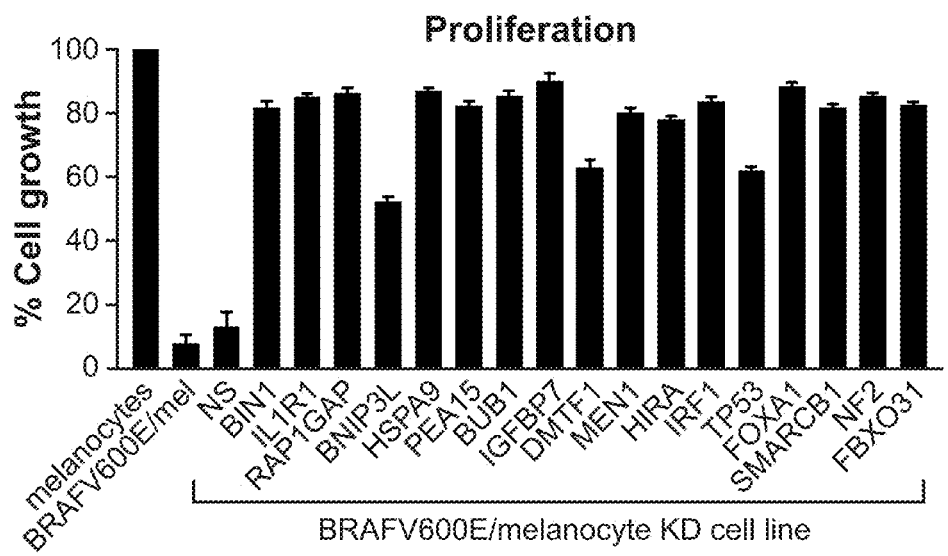
FIG. 1C is a bar graph depicting quantitative proliferation assays of the 17 BRAFV600E/melanocyte KD cell lines. BJ fibroblasts stably expressing the indicated shRNA were infected with the BRAFV600E-expressing retrovirus and after 14 days analyzed by trypan blue exclusion test. Growth of BRAFV600E/melanocytes is expressed relative to the growth of normal melanocytes. For the BRAFV600E/melanocyte KD cell lines, values were normalized to the growth of the corresponding melanocyte KD cell line in the absence of BRAFV600E expression. Error bars represent standard error.

As expected from previous studies (Michaloglou et al., 2005, Nature, 436:720-724), expression of BRAFV600E in primary melanocytes efficiently blocked cellular proliferation (FIG. 1C). By contrast, BRAFV600E failed to block cellular proliferation in all 17 melanocyte KD cell lines. Thus, the 17 genes we identified are required for BRAFV600E to block proliferation of both PFFs and primary melanocytes.

Figure 1D:
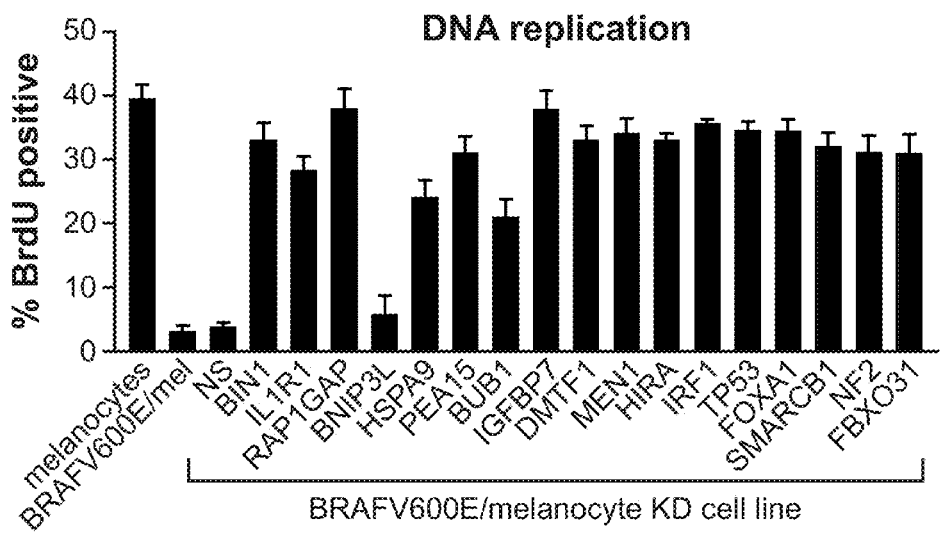
FIG. 1D is a bar graph depicting DNA replication assays of the 17 BRAFV600E/melanocyte KD cell lines. DNA replication was monitored by BrdU incorporation 4 days after BRAFV600E expression.
Figure 1E:
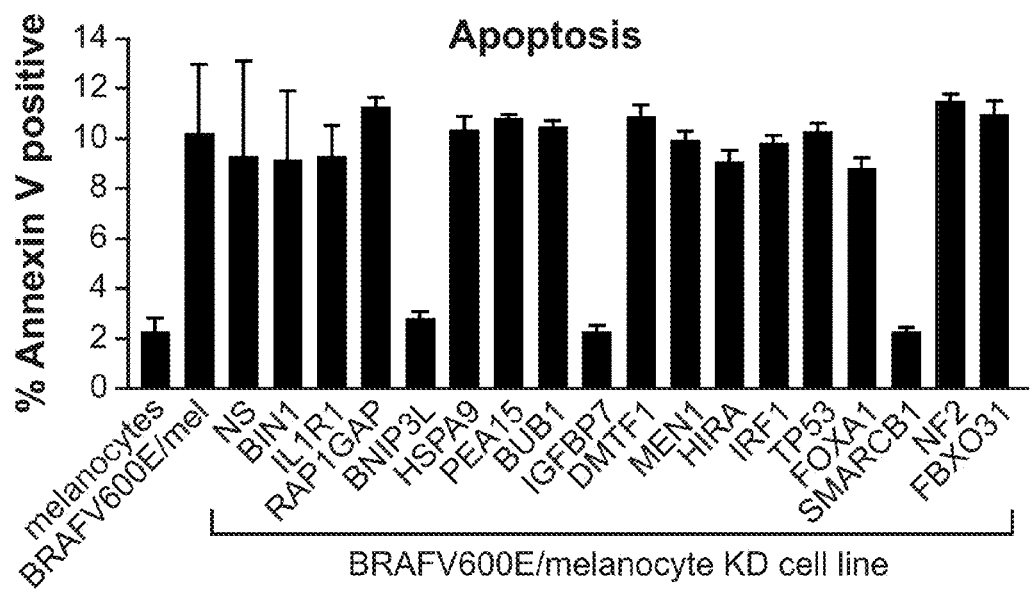
FIG. 1E is a bar graph depicting apoptosis of the 17 BRAFV600E/melanocyte KD cell lines. Apoptosis was monitored by Annexin V-PE staining 4 days after BRAFV600E expression.

Following expression of BRAFV600E in melanocytes, the majority of cells became senescent (FIG. 1D), consistent with previous studies (Michaloglou et al., 2005, Nature, 436:720-724), although ~10% of cells underwent apoptosis (FIG. 1E). To determine the role of the 17 genes in these two pathways, apoptosis and senescence assays were performed in each melanocyte KD cell line following BRAFV600E expression. The results of FIG. 1E show that only three of the 17 genes were required for apoptosis: BNIP3L, which encodes a pro-apoptotic BCL2 family protein; SMARCB1, which encodes a component of the SWI/SNF chromatin remodeling complex; and insulin growth factor binding protein 7 (IGFBP7), which encodes a secreted protein with weak homology to IGF binding proteins. By contrast, all but one of the 17 genes, BNIP3L, were required for BRAFV600E to induce growth arrest (FIG. 1D) and characteristic markers of senescence (see below). Identical results were obtained in PFFs.

Figure 1F:
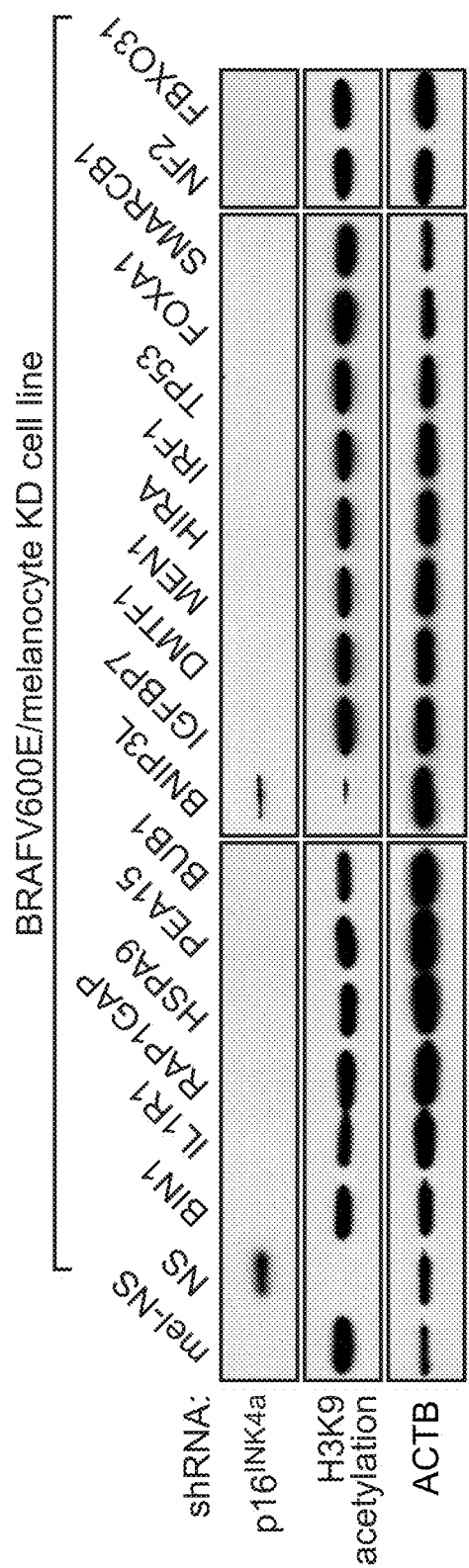
FIG. 1F is a set of immunoblots depicting immunoblot analysis monitoring induction of p16$^{INK4a}$ and acetylation of histone 3 lysine 9 (H3K9) in each of the 17 BRAFV600E/melanocyte KD cell lines. β-ACTIN (ACTB) was monitored as a loading control.

The cell cycle inhibitor p16$^{INK4a}$ has been proposed to play an important role in replicative and oncogene-induced senescence (reviewed in Ben-Porath and Weinberg, 2005, Int. J. Biochem. Cell Biol., 37:961-976). For example, p16$^{INK4a}$ is induced in melanocytes following expression of activated BRAF, is expressed in melanocytic nevi, and is frequently deleted in melanomas (Michaloglou et al., 2005, Nature, 436:720-724; Piccinin et al., 1997, Int. J. Cancer, 74:26-30). It was therefore determined whether the genes identified in our screen were required for p16$^{INK4a}$ induction. FIG. 1F shows that p16$^{INK4a}$ levels increased substantially following BRAFV600E expression in control melanocytes expressing a non-silencing shRNA. Significantly, p16$^{INK4a}$ expression was not induced by BRAFV600E in 16 of the 17 melanocyte KD cell lines. The sole exception was the cell line knocked down for BNIP3L, which, as described above, is specifically involved in apoptosis. Loss of histone H3 lysine 9 (H3K9) acetylation, another well characterized senescence marker (Narita et al., 2006, Cell, 126:503-514), also occurred following BRAFV600E expression in control melanocytes, but not in any of the melanocyte KD cell lines except for the BNIP3L KD cell line (FIG. 1F).

Example 2

A Secreted Protein, IGFBP7, Induces Senescence and Apoptosis Through an Autocrine/Paracrine Pathway The 17 genes identified in the screen encoded known tumor suppressors (TP53, MEN 1, NF2, and SMARCB1), pro-apoptotic proteins (BNIP3L), cell cycle regulators (BUB1), and modulators of the RAS-RAF-MEK-ERK signaling pathway (PEA15, RAP1GAP, and HSPA9). Unexpectedly, one of the genes required for the induction of both senescence and apoptosis was IGFBP7, which encodes a secreted protein (Wilson et al., 1997, J. Clin. Endocrinol. Metab., 82:1301-1303). This result raised the possibility that the BRAFV600E-mediated block to cellular proliferation might occur through an autocrine/paracrine pathway in which IGFBP7 functions extracellularly.

Figure 2A:
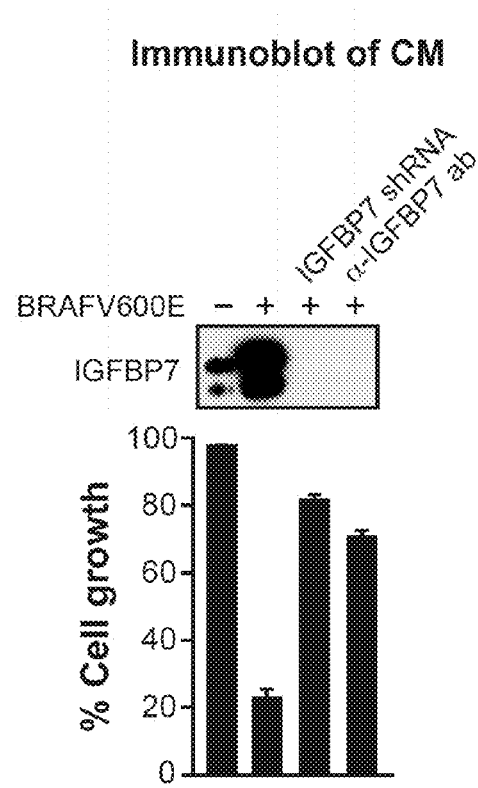
FIG. 2A (top) is an analysis of IGFBP7 levels in CM from normal melanocytes, BRAFV600E/melanocytes, BRAFV600E/melanocytes stably expressing an IGFBP7 shRNA or in BRAFV600E/melanocyte CM treated with an α-IGFBP7 antibody to immunodeplete IGFBP7.
Figure 2B:
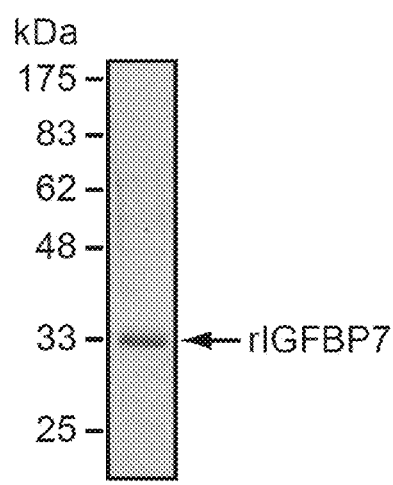
FIG. 2B is a Coomassie-stained gel of purified, recombinant IGFBP7 (rIGFBP7). The positions of molecular weight markers are shown on the left, in kDa.
Figure 2C:
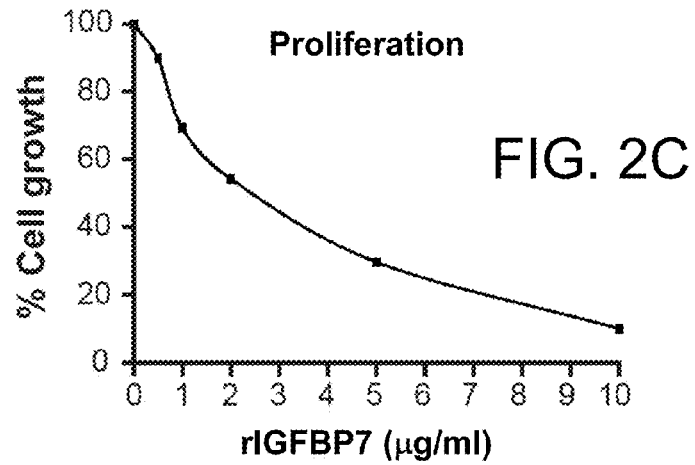
FIG. 2C is a line graph depicting a proliferation assay monitoring the effect of rIGFBP7 on the growth of melanocytes 14 days after treatment.
Figure 2D:
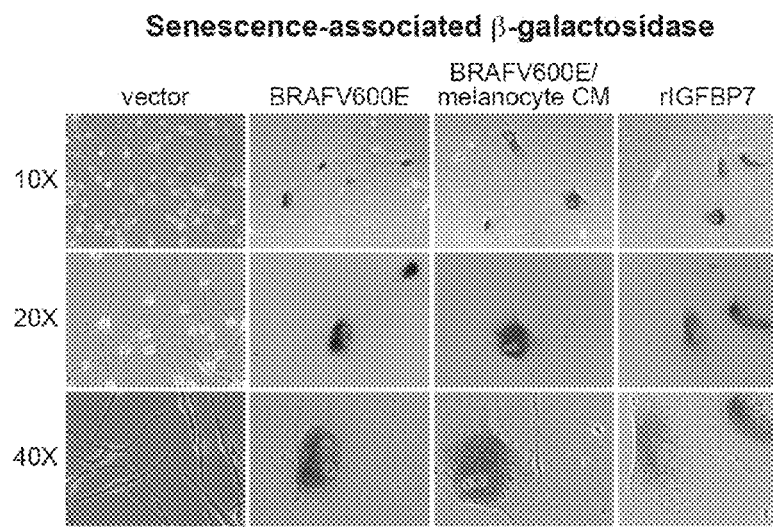
FIG. 2D is a set of twelve micrographs depicting β-galactosidase staining of melanocytes infected with a retrovirus expressing either empty vector (first column) or BRAFV600E (second column), or melanocytes treated with CM from BRAFV600E/melanocytes (third column) or rIGFBP7 (fourth column). Images are shown at a magnification of 10×, 20× and 40×.

To confirm that IGFBP7 is in fact secreted and ask whether IGFBP7 functions extracellularly, the ability of conditioned medium (CM) from BRAFV600E-melanocytes to induce senescence was analyzed. The immunoblot of FIG. 2A (top panel) shows that following expression of BRAFV600E in melanocytes, the level of IGFBP7 in CM increased substantially. Addition of CM from BRAFV600E-melanocytes to naïve melanocytes blocked cellular proliferation, primarily resulting from the induction of senescence (FIG. 2A, bottom panel and see FIG. 2D below).

Two experiments verified that IGFBP7 activation was downstream of BRAF-MEK-ERK signaling. First, BRAFV600E-mediated induction of IGFBP7 was blocked by addition of a MEK inhibitor. Second, expression of a constitutively activated ERK mutant (ERK2Q103A or ERK2L73P, S151D) was sufficient to activate IGFBP7 transcription.

The IGFBP7 promoter contains a consensus binding site for the dimeric AP-1 (JUN/FOS) transcription factor. JUN (also known as c-Jun) is activated through RAF-MEK-ERK signaling (Leppa et al., 1998, EMBO J., 17:4404-13), raising the possibility that AP-1 is involved in BRAFV600E-mediated induction of IGFBP7. Chromatin immunoprecipitation (ChIP) analysis verified that JUN bound to the IGFBP7 promoter in response to BRAFV600E expression, and siRNA-mediated knockdown of JUN abrogated induction of IGFBP7 transcription in BRAFV600E/melanocytes.

Next, it was verified that IGFBP7 was the secreted protein responsible for the BRAFV600E-mediated cellular proliferation block. In one experiment, BRAFV600E-melanocytes were treated with an shRNA targeting IGFBP7. FIG. 2A shows that IGFBP7 was absent from the CM of BRAFV600E-melanocytes expressing an IGFBP7 shRNA (top panel), and that this CM did not inhibit cellular proliferation of naïve melanocytes (bottom panel). In a second experiment, immunodepletion with an α-IGFBP7 antibody efficiently removed IGFBP7 from CM of BRAFV600E-melanocytes (top panel). Immunodepleted CM also failed to inhibit cellular proliferation of naïve melanocytes (bottom panel).

To confirm that IGFBP7 could block cellular proliferation, purified recombinant IGFBP7 (rIGFBP7) was purified from baculovirus-infected insect cells. FIG. 2B shows that following expression and purification, a polypeptide of ~33 kDa was detected (the expected size of rIGFBP7). Addition of rIGFBP7 blocked proliferation of primary melanocytes in a dose-dependent manner (FIG. 2C). The growth-arrested cells had an enlarged, flat morphology and stained positively for senescence-associated β-galactosidase (FIG. 2D). Collectively, the results of FIGS. 2A-2D indicate that following expression of BRAFV600E, melanocytes synthesize and secrete increased amounts of IGFBP7, which then acts through an autocrine/paracrine pathway to induce senescence.

Figure 2E:
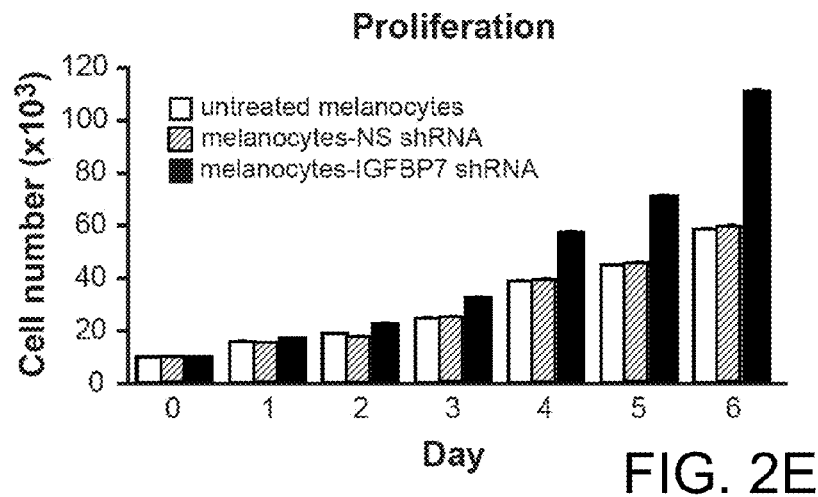
FIG. 2E is a set bar graphs depicting growth rates of untreated melanocytes, or melanocytes stably expressing a non-silencing (NS) or IGFBP7 shRNA. Cell number was monitored every day for six days.

The finding that primary melanocytes express low levels of IGFBP7 (FIG. 2A and see below) raised the possibility that under normal conditions IGFBP7 might regulate melanocyte proliferation. To test this idea, the proliferation rates of untreated melanocytes, control melanocytes expressing a non-silencing shRNA, and melanocytes expressing an IGFBP7 shRNA were compared. The results of FIG. 2E show that melanocyte proliferation increased following IGFBP7 knockdown. Thus, normal melanocytes express low levels of IGFBP7, which restrains proliferation. When present at high levels, such as following expression of BRAFV600E, IGFBP7 induces senescence.

Example 3

Figure 3A:
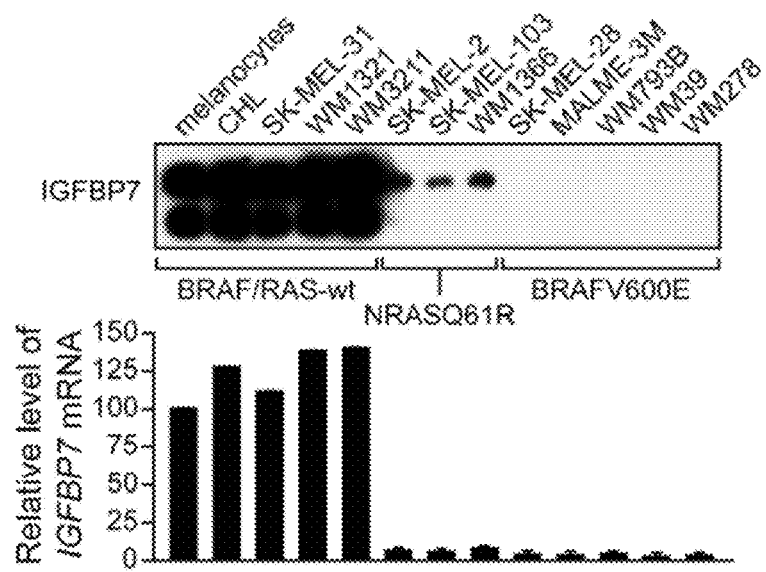
FIG. 3A is an immunoblot analysis (top) monitoring expression of IGFBP7 in the CM from human melanoma cell lines and an associated bar graph (bottom) showing quantitative real-time RT-PCR analysis of IGFBP7 expression of human melanoma cell lines containing either an activating BRAFV600E mutation (SK-MEL-28, MALME-3M, WM793B, WM39, and WM278), an activating RASQ61R mutation (SK-MEL-2, SK-MEL-103, and WM1366), or were wild type for both BRAF and RAS (CHL, SK-MEL-31, WM1321, and WM3211). Error bars represent standard error.
Figure 3B:
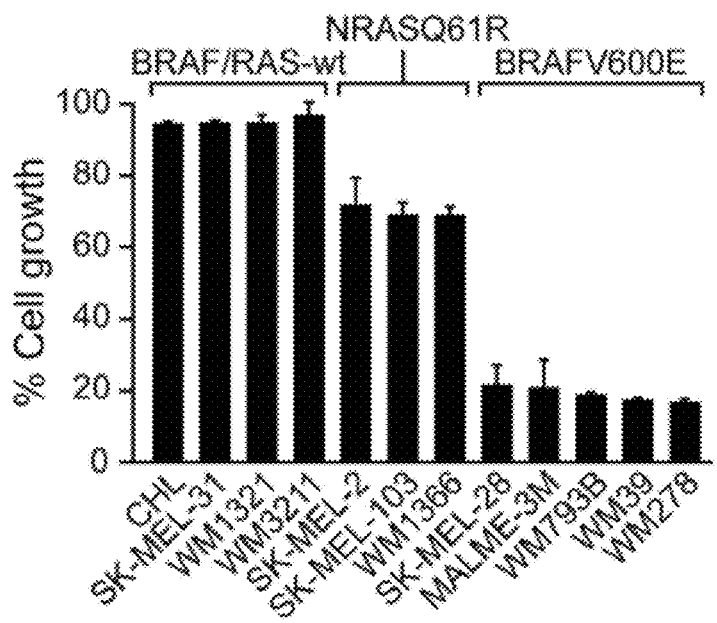
FIG. 3B is a bar graph depicting proliferation of human melanoma cell lines 24 hours after treatment with rIGFBP7. Proliferation was normalized to the growth of the corresponding cell line in the absence of rIGFBP7 addition. Error bars represent standard error.

Selective Sensitivity of Melanoma Cell Lines Containing an Activating BRAF Mutation to IGFBP7-Mediated Apoptosis Next, the ability of IGFBP7 to block cellular proliferation in a panel of human melanoma cell lines was analyzed. The cells contained either an activating BRAF mutation (BRAFV600E; SK-MEL-28, MALME-3M, WM793B, WM39 and WM278), an activating RAS mutation (RASQ61R; SK-MEL-2, SK-MEL-103, and WM1366), or were wild type for both BRAF and RAS (CHL, SK-MEL-31, WM1321 and WM3211). For each cell line, the presence of IGFBP7 in the CM was determined by immunoblot analysis (FIG. 3A), and sensitivity to IGFBP7-induced growth inhibition was measured in a proliferation assay (FIG. 3B). The results reveal a striking inverse correlation between IGFBP7 expression and sensitivity to IGFBP7-mediated growth inhibition that correlates with the status of BRAF or RAS. Most importantly, melanoma cell lines harboring an activating BRAF mutation failed to express IGFBP7 and were highly sensitive to IGFBP7-mediated growth inhibition. By contrast, cells with wild type BRAF and RAS expressed IGFBP7 and were relatively insensitive to IGFBP7-mediated growth inhibition. Finally, melanoma cell lines containing an activating RAS mutation expressed low levels of IGFBP7 and were partially sensitive to IGFBP7-mediated growth inhibition.

Figure 3C:
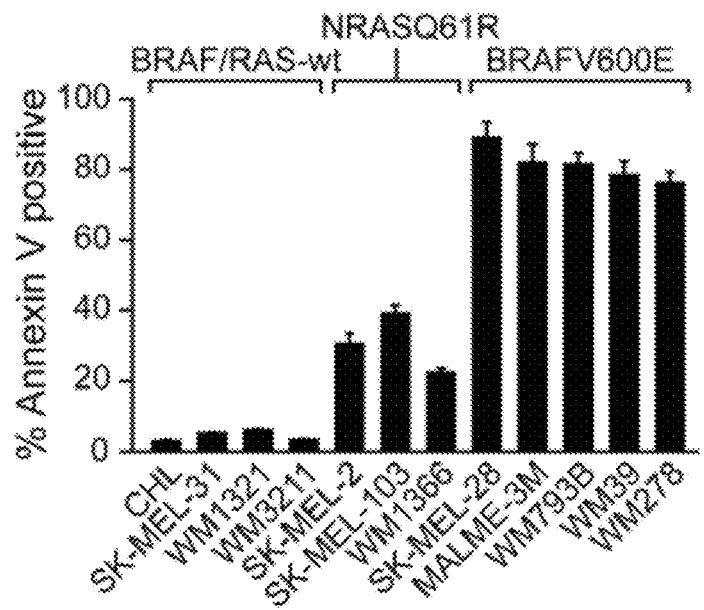
FIG. 3C is a bar graph depicting apoptosis of human melanoma cell lines 24 hours after treatment with rIGFBP7.

The IGFBP7-mediated cellular proliferation block was further analyzed with regard to apoptosis and senescence. Significantly, in melanoma cell lines harboring an activating BRAF mutation, rIGFBP7 strongly induced apoptosis and surviving senescent cells were undetectable (FIG. 3C). Thus, IGFBP7 primarily induced senescence in primary melanocytes and apoptosis in BRAFV600E-positive melanoma cells.

To understand the basis of this differential response, expression of the 17 identified genes was analyzed in primary melanocytes and BRAFV600E-positive SK-MEL-28 melanoma cells. Quantitative RT-PCR showed that in primary melanocytes, expression of BRAFV600E resulted in the transcriptional upregulation of seven genes which are involved in apoptosis (BNIP3L, IGFBP7 and SMARCB1) and senescence (PEAL 5, IGFBP7, MEN1, FBXO31, SMARCB1, and HSPA9). BRAFV600E-mediated induction of all seven genes did not occur with knockdown of IGFBP7. Following addition of rIGFBP7 to melanocytes, six of the seven genes were induced, IGFBP7 being the exception. Significantly, following addition of rIGFBP7 to SK-MEL-28 cells, neither IGFBP7 nor PEA15 were upregulated. PEA15, a known regulator of BRAF-MEK-ERK signaling (Formstecher et al., 2001, Dev. Cell, 1:239-250), is required for senescence (see FIG. 1F). Thus, the lack of PEA15 induction in IGFBP7-treated SK-MEL-28 cells can explain their failure to undergo senescence. BNIP3L is only modestly upregulated in primary melanocytes following expression of BRAFV600E or addition of rIGFBP7, consistent with the relatively low level of apoptosis in IGFBP7-treated melanocytes (see FIG. 1E).

Example 4

IGFBP7 Induces Apoptosis Through Upregulation of BNIP3L

Figure 3D:
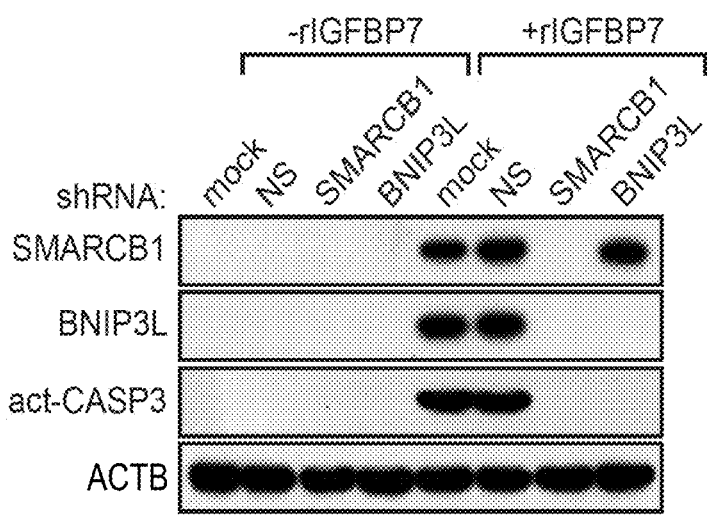
FIG. 3D is a set of immunoblots of expression of SMARCB1, BNIP3L and activated caspase 3 (act-CASP3) in SK-MEL-28 cells in the presence or absence of rIGFBP7 and stably expressing either a non-silencing (NS), SMARCB1 or BNIP3L shRNA. β-actin (ACTB) was monitored as a loading control.

As described above, BRAFV600E-mediated apoptosis was dependent upon IGFBP7, SMARCB1, and BNIP3L, raising the possibility that these three proteins were components of a common pathway required for apoptosis. A series of experiments was performed to confirm this idea and establish the order of the pathway. FIG. 3D shows that following addition of rIGFBP7 to SK-MEL-28 cells, expression of SMARCB1 and BNIP3L was significantly increased, and apoptosis occurred as evidenced by caspase 3 activation. Expression of a SMARCB1 shRNA blocked induction of BNIP3L and apoptosis. By contrast, expression of a BNIP3L shRNA still resulted in induction of SMARCB1 following rIGFBP7 addition, although apoptosis did not occur. Collectively, these results reveal a pathway in which IGFBP7 increases expression of SMARCB1, which in turn leads to increased expression of BNIP3L, culminating in apoptosis (FIG. 3D, bottom panel).

In BRAFV600E/melanocytes, induction of SMARCB1 and BNIP3L was blocked following IGFBP7 knockdown. Moreover, addition of CM from BRAFV600E-expressing melanocytes to naïve melanocytes substantially upregulated SMARCB1 and BNIP3L, which did not occur with various control CMs that lacked IGFBP7. Thus, in BRAFV600E/melanocytes induction of SMARCB1 and BNIP3L is also dependent upon and downstream of IGFBP7.

The mechanistic basis for IGFBP7-mediated induction of BNIP3L and SMARCB1 was next determined. STAT1 is involved in certain SMARCB1-inducible transcription responses, and the SMARCB1 promoter contains a STAT1 binding site located ~2.4 kb upstream of the transcription start-site (Hartman et al., 2005, Genes Dev., 19:2953-68). The potential role of STAT1 in IGFBP7-mediated induction of SMARCB1 transcription was investigated. ChIP experiments revealed that following addition of rIGFBP7 to SK-MEL-28 cells, STAT1 was recruited to the SMARCB1 promoter (FIG. 3E), and shRNA-mediated knockdown experiments confirmed that STAT1 was required for IGFBP7-mediated upregulation of SMARCB1 (FIG. 3F).

As described above, SMARCB1 is required for upregulation of BNIP3L by IGFBP7 (FIG. 3D). ChIP experiments revealed that following addition of rIGFBP7, SMARCB1 as well as BRG1, an essential subunit of the SWI/SNF complex (Bultman et al., 2000, Mol. Cell, 6:1287-95), were recruited to the BNIP3L promoter near the transcription start-site (FIG. 3G). Following knockdown of SMARCB1, BRG1 (and, as expected, SMARCB1) failed to associate with the BNIP3L promoter. Collectively, these results indicate that IGFBP7 stimulates BNIP3L transcription, at least in part, by increasing intracellular levels of SMARCB1, leading to formation of a SMARCB1-containing SWI/SNF chromatin-remodeling complex, which is recruited to the BNIP3L promoter and facilitates BNIP3L transcriptional activation.

Finally, it was determined whether apoptosis was dependent upon the continual presence of rIGFBP7 or was irreversible following transient exposure to rIGFBP7. SK-MEL-28 cells were incubated with rIGFBP7 for various lengths of time, following which the cells were washed and cultured in medium lacking rIGFBP7, and apoptosis was quantitated after 24 hours. The results, shown in FIG. 3H, indicate that following 6 hours of incubation with rIGFBP7, the cells were irreversibly committed to apoptosis, which occurred even following removal of rIGFBP7.

Example 5

IGFBP7 Blocks BRAF-MEK-ERK Signaling to Activate the Apoptotic Pathway

As mentioned above, in BRAFV600E-positive melanoma cells BRAF-MEK-ERK signaling is hyper-activated, rendering the cells highly dependent on this pathway. Thus, treatment of BRAFV600E-positive melanoma cells with a BRAF shRNA (Hoeflich et al., 2006, Cancer Res., 999-1006) or an inhibitor of BRAF (Sharma et al., 2005, Cancer Res., 65:2412-2421) or MEK (Solit et al., 2006, Nature, 439:358-362) blocks cellular proliferation. It was determined whether IGFBP7 blocks cellular proliferation, at least in part, by inhibiting BRAF-MEK-ERK signaling.

To test this idea, rIGFBP7 was added to BRAFV600E-positive SK-MEL-28 melanoma cells, and the levels of total and activated ERK (phospho-ERK) were analyzed. The immunoblot experiment of FIG. 4A shows that addition of rIGFBP7 resulted in a dose-dependent loss of phospho-ERK, indicating that BRAF-MEK-ERK signaling was inhibited.

Similarly, expression of BRAFV600E in melanocytes markedly decreased phospho-ERK levels, which did not occur in BRAFV600E/melanocytes expressing an IGFBP7 shRNA. Moreover, addition of CM from BRAFV600E/melanocytes to naïve melanocytes substantially decreased the levels of phospho-ERK, which did not occur with various control CMs that lacked IGFBP7. rIGFBP7 also blocked growth factor-induced ERK activation. Collectively, these results indicate that IGFBP7 inhibits BRAF-MEK-ERK signaling.

Addition of rIGFBP7 to SK-MEL-28 cells resulted in decreased levels of activated MEK1/2, corresponding with the reduced phospho-ERK levels and apoptosis. Moreover, ectopic expression of a constitutively activated MEK1 mutant (MEK1EE) prevented IGFBP7 from blocking ERK activation. These results demonstrate that IGFBP7 blocks phosphorylation of MEK by BRAF. Finally, addition of IGFBP7 to SK-MEL-28 cells resulted in upregulation of RAF inhibitory protein (RKIP), which has been shown to interact with several RAF proteins, including BRAF, and inhibit RAF-mediated phosphorylation of MEK (see, for example, Park et al., 2005, Oncogene, 24:3535-40). Following knockdown of RKIP in SK-MEL-28 cells, rIGFBP7 failed to block activation of MEK or ERK. Collectively, these results indicate that IGFBP7 inhibits BRAF-MEK-ERK signaling by inducing RKIP, which prevents BRAF from phosphorylating MEK.

To establish the relationship between inhibition of BRAF-MEK-ERK signaling and the IGFBP7-mediated block to cellular proliferation, sensitivity to rIGFBP7 was analyzed in a constitutively activated ERK2 mutant (ERK2Q103A or ERK2L73P,S151D). FIG. 4B shows that expression of either ERK2 an ERK2 (left) or MEK1 (right) mutant in SK-MEL-28 cells substantially overcame the IGFBP7-mediated cellular proliferation block. Expression of a constitutively activated ERK2 mutant also blocked BRAFV600E- and IGFBP7-induced senescence in melanocytes. In addition, ectopic expression of either constitutively activated ERK2 mutant increased phospho-ERK2 levels and prevented the IGFBP7-mediated upregulation of BNIP3L and induction of apoptosis (FIG. 4C).

The above results led to two conclusions. First, IGFBP7 blocked cellular proliferation, at least in part, through inhibition of BRAF-MEK-ERK signaling. Second, inhibition of BRAF-MEK-ERK signaling was required for activation of the IGFBP7-mediated apoptotic pathway. FIG. 4D shows that addition of a chemical inhibitor of MEK or RAF blocked BRAF-MEK-ERK signaling. However, unlike rIGFBP7, MEK and RAF inhibitors did not increase BINP3L levels or efficiently induce apoptosis, indicating that inhibition of BRAF-MEK-ERK signaling is not sufficient to induce IGFBP7-mediated apoptosis. Thus, IGFBP7 has a second, independent activity required for induction of the apoptotic pathway.

Example 6

IGFBP7 Suppresses Growth of BRAFV600E-Positive Tumors in Xenografted Mice

The ability of IGFBP7 to inhibit proliferation of BRAFV600E-positive human melanoma cell lines (see FIG. 3B) raised the possibility that IGFBP7 could suppress growth of tumors containing an activating BRAF mutation. As a first test of this possibility, human melanoma cells that contained (SK-MEL-28) or lacked (SK-MEL-31) an activating BRAF mutation were injected subcutaneously into the flanks of nude mice. Three, six, and nine days later, the mice were injected at the tumor site with either rIGFBP7 or, as a control, PBS. The results of FIG. 5A show that rIGFBP7 substantially suppressed growth of BRAFV600E-positive tumors but had no effect on tumors containing wild type BRAF.

It was also determined whether tumor growth could also be suppressed by systemic administration of rIGFBP7. SK-MEL-28 or SK-MEL-31 cells were injected into the flanks of nude mice, and when tumors reached a size of 100 mm$^3$, 100 µg rIGFBP7 was delivered by tail vein injection at days 6, 9, and 12. The results of FIG. 5B show that systemic administration of rIGFBP7 completely suppressed growth of BRAFV600E-positive tumors, whereas tumors containing wild type BRAF were unaffected. In mice treated with rIGFBP7, BRAFV600E-positive tumors were deoxyuridine triphosphate nick-end labeling (TUNEL)-positive, indicating that suppression of tumor growth resulted from apoptosis. Suppression of tumor growth by systemically administered rIGFBP7 was dose-dependent, and concentrations higher than that required for inhibition of tumor growth could be delivered without apparent adverse effects (FIG. 5C).

Example 7

Loss of IGFBP7 Expression is Critical for BRAFV600E-Positive Melanoma

As shown above, BRAFV600E-positive melanoma cell lines fail to express IGFBP7 and are highly sensitive to IGFBP7-mediated apoptosis. These results raised the possibility that IGFBP7 functions as a tumor suppressor and loss of IGFBP7 might be required for development of BRAFV600E-positive melanoma. To investigate this possibility, we performed immunohistochemical analysis of IGFBP7 expression on a series of human skin, nevi, and melanoma samples.

Figure 6A:
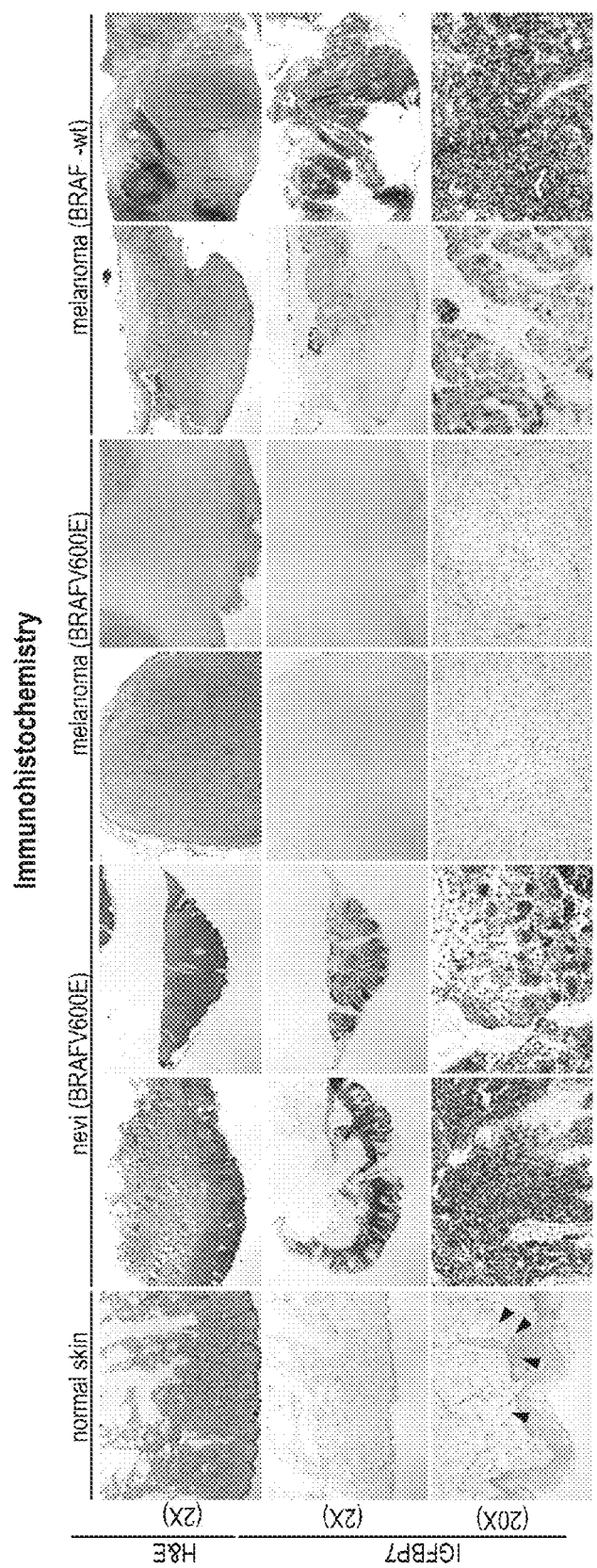
FIG. 6A is a set of immunohistochemical slides depicting IGFBP7 expression in normal human skin (normal skin—column 1), nevi (BRAFV600E-positive—columns 2 and 3), and melanoma (BRAFV600E—columns 4 and 5; and BRAF-wt—columns 6 and 7) samples. Samples were stained with hematoxylin and eosin (H&E) (row 1). Images depicting IGFBP7 expression are shown at 2× (row 2) and/or 20× (row 3) magnification. Arrowheads indicate IGFBP7-positive melanocytes in normal skin.
Figure 6B:
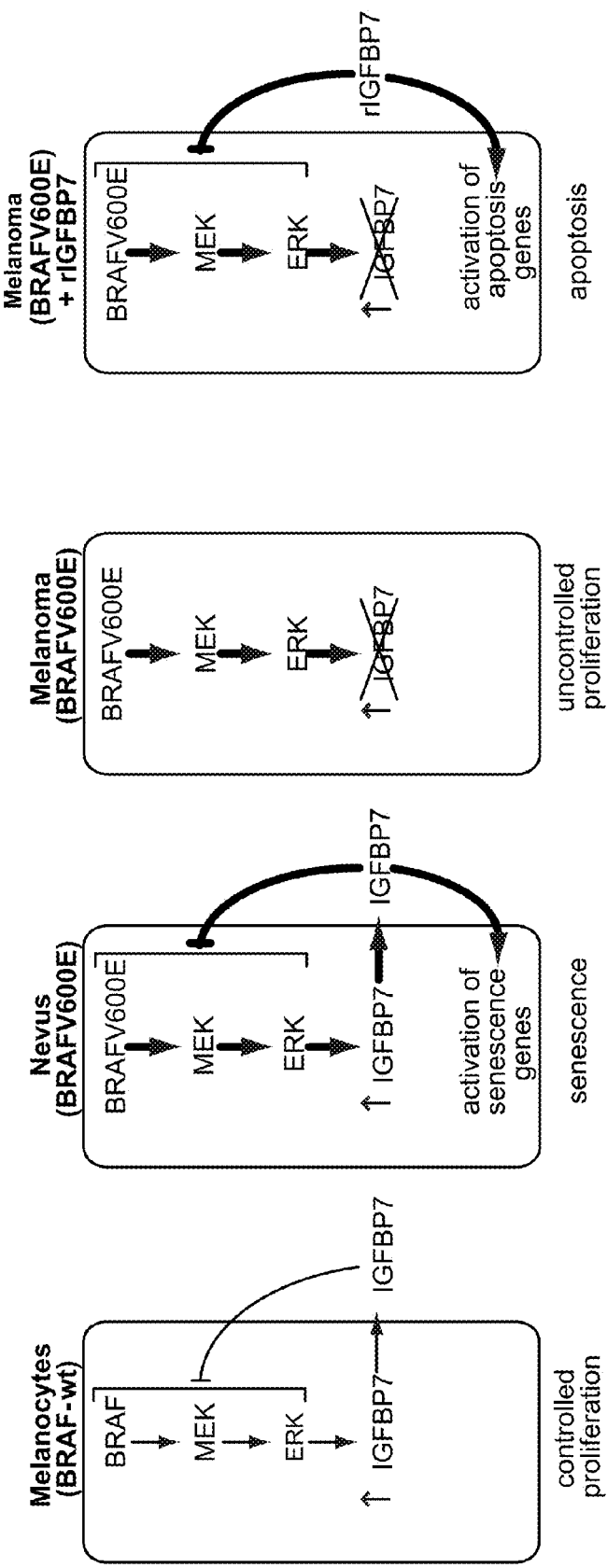
FIG. 6B is a schematic summary of how activated BRAF promotes senescence. In BRAF-wt melanocytes, normal signaling through the BRAF-MEK-ERK pathway leads to induction of IGFBP7, which in turn inhibits the BRAF-MEK-ERK pathway through an autocrine/paracrine pathway; the result is controlled proliferation. In BRAFV600E-positive nevi, constitutive activation of the BRAF-MEK-ERK pathway leads to induction of IGFBP7, which inhibits the pathway and activates senescence genes. In BRAFV600E-positive melanoma, IGFBP7 expression is lost, and the cells undergo uncontrolled proliferation. Addition of exogenous IGFBP7 inhibits the BRAF-MEK-ERK pathway and activates apoptosis genes.

The results of FIG. 6 and Table 2 show that normal skin melanocytes expressed low but detectable levels of IGFBP7, consistent with the results in cultured primary melanocytes (see FIG. 2A). BRAFV600E-positive nevi expressed high levels of IGFBP7, consistent with the finding that expression of BRAFV600E in melanocytes increased IGFBP7 levels (FIG. 2A). Significantly, BRAFV600E-positive melanomas did not express detectable levels of IGFBP7. By contrast, IGFBP7 was clearly expressed in melanomas lacking activated BRAF.

TABLE 2

BRAFV600E and IGFBP7 status in human skin, nevi, and melanoma samples

| Pathology | No. of samples | BRAFV600E status | IGFBP7 status |
|---|---|---|---|
| Normal skin | 5 | – | + |
| Benign nevus | 20 | + | + |
| Melanoma | 13 | + | – |
| Melanoma | 7 | – | + |

Figure 10A:
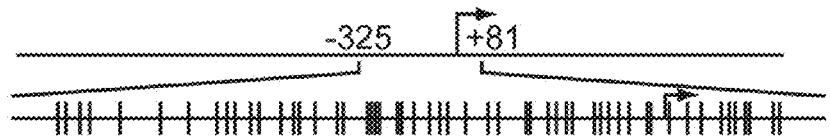
FIG. 10A is a schematic of the IGFBP7 promoter; positions of the CpG dinucleotides are shown to scale by vertical lines.
Figure 10B:
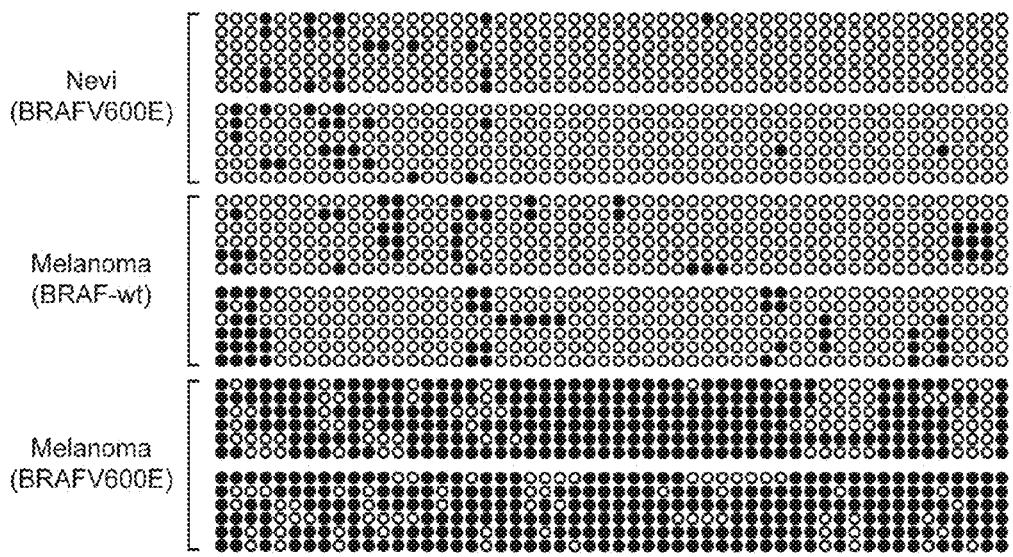
FIG. 10B is a bisulfite sequence analysis of the IGFBP7 promoter in melanocytic nevi (BRAFV600E), melanoma (BRAF wt), and melanoma (BRAFV600E). Each circle represents a CpG dinucleotide: open (white) circles denote unmethylated CpG sites and filled (black) circles indicate methylated CpG sites. Each row represents a single clone.
Figure 10C:
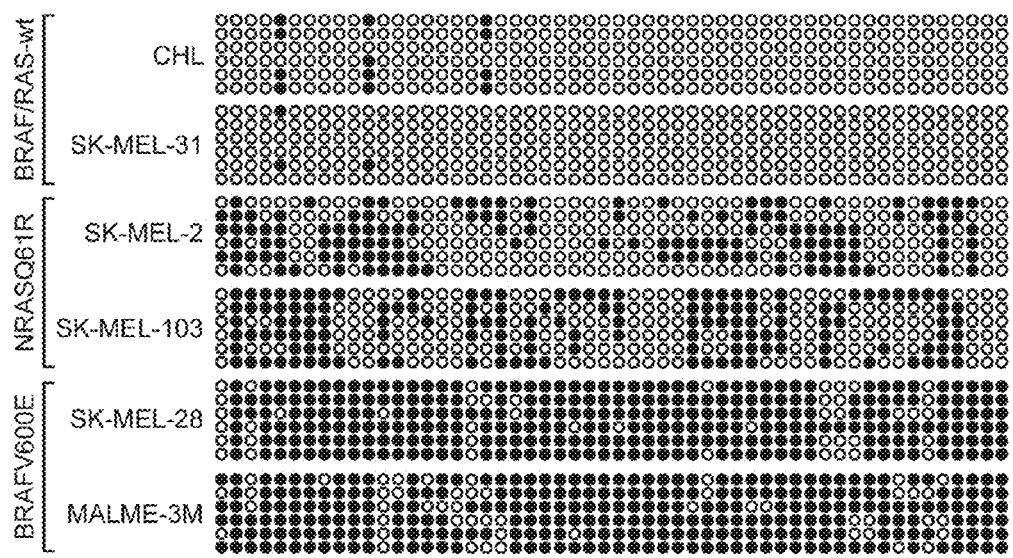
FIG. 10C is a bisulfite sequence analysis of the IGFBP7 promoter in a panel of the indicated melanoma cell lines. Each circle represents a CpG dinucleotide: open (white) circles denote unmethylated CpG sites and filled (black) circles indicate methylated CpG sites. Each row represents a single clone.
Figure 10D:
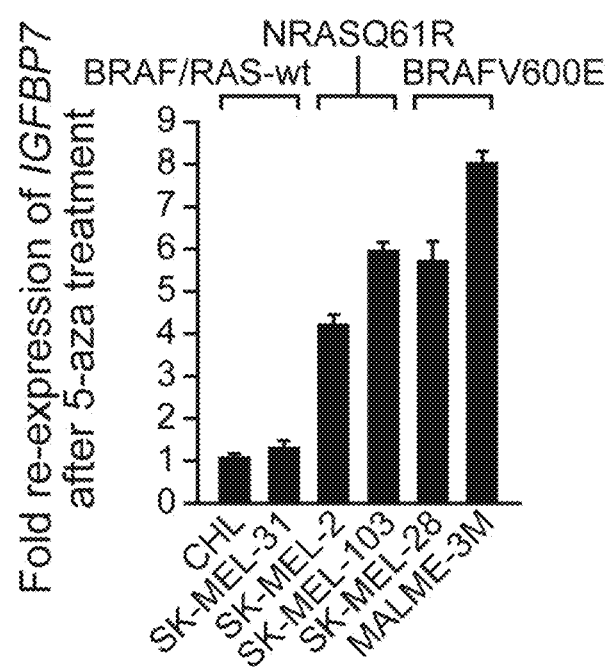
FIG. 10D is a bar graph depicting IGFBP7 mRNA levels in melanoma cell lines following treatment with the DNA methyltransferase inhibitor 5-aza-2'-deoxycytidine (5-aza), as measured by qRT-PCR. Error bars represent standard error.

To determine whether loss of IGFBP7 expression was the result of epigenetic silencing, bisulfite sequence analysis was performed. FIG. 10A shows that the IGFBP7 promoter was densely hypermethylated in BRAFV600E-positive melanomas but not in BRAFV600E-positive nevi or melanomas lacking activated BRAF. Similar analyses in a panel of melanoma cell lines showed that the IGFBP7 promoter was densely hypermethylated in BRAFV600E-positive melanoma cell lines and modestly hypermethylated in NRASQ61R-positive melanoma cell lines (FIG. 10B). Treatment of these cell lines with the DNA methyltransferase inhibitor 5-aza-2'-deoxycytidine restored IGFBP7 expression in BRAFV600E- and NRASQ61R-positive cell lines but had no effect in BRAF/RAS-wild type cell lines (FIG. 10C).

Collectively, these results suggest that during the development of a BRAFV600E-positive melanoma, IGFBP7 expression is lost (e.g., from epigenetic silencing involving promoter hypermethylation), enabling escape from the BRAFV600E-mediated senescence that is characteristic of nevi.

Example 8

A Functional Peptide Derivative of IGFBP7

The inhibitory activity of a peptide derivative of IGFBP7 was assessed. Based on previous observations (Sato et al., 1999, J Cell Biochem. 1999 Nov. 1; 75(2):187-95) a 20 amino acid peptide $G_{84}MECVKSRKRRKGKAGAAAG_{103}$ (SEQ ID NO:7) was produced. This peptide was tested for its ability to induce cord-like structures in vascular endothelial cells when assayed as described previously (Akaogi et al., Cell Growth Differ. 1996 December; 7(12):1671-7). The 20-amino acid peptide had similar activity to full-length IGFBP7 to induce cord-like structures in vascular endothelial cells.

Example 9

Combined Treatment with IGFBP7 and IDO Inhibitors

Melanoma patients positive for lymphocyte infiltration have better prognosis, decreased recurrence and almost no metastasis. Advances that can improve the immune surveillance in melanoma will have significant impact on improving the quality of life for the melanoma patients. The mitogen-activated protein kinase (MAPK) pathway is frequently activated in human melanoma, leading to malignant phenotype such as autonomous cellular proliferation. The screen described above identified a gene named BIN1 that affects the enzyme indoleamine 2,3-dioxygenase (IDO). IDO catabolizes the first step in tryptophan metabolism, thus depleting the tryptophan pool on which T-cells depend for their activity. The IDO level and lymphocyte infiltration in melanoma samples with BRAFV600E and WT BRAF are analyzed. The use of IDO inhibitors in combination with BRAF-MEK-ERK pathway inhibitors (e.g., IGFBP7 agents described herein) can provide additional effects for treatment of melanoma.

Example 10

Human Cancer Cell Lines are Sensitive to IGFBP7-Mediated Apoptosis

Figure 11A:
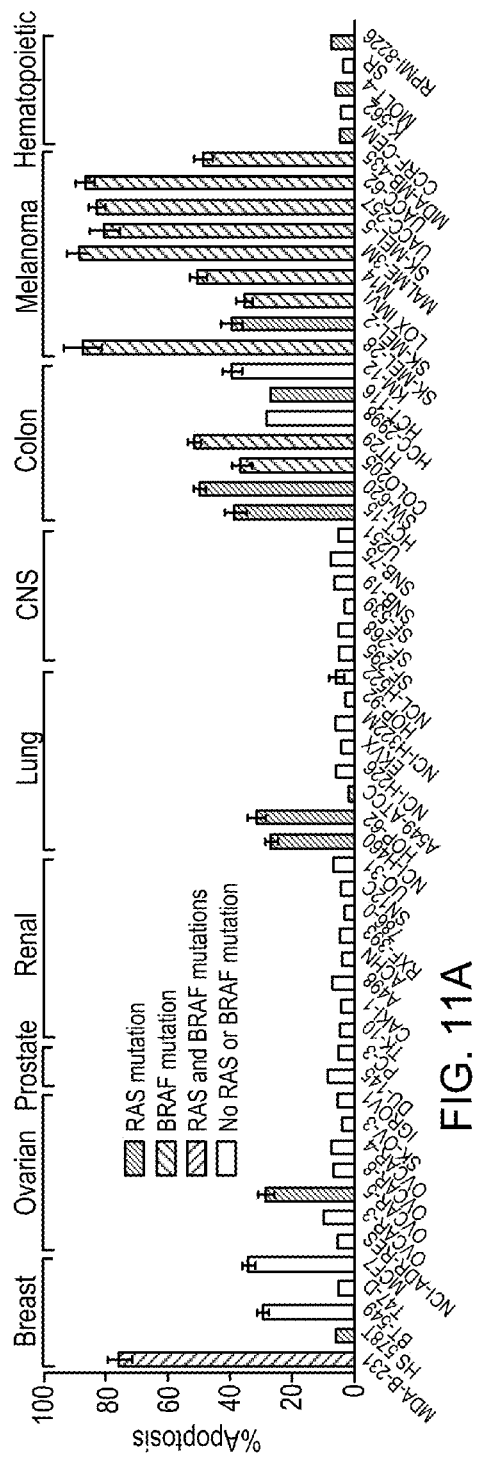
FIG. 11A is a bar graph depicting sensitivity of the indicated human cancer cell lines to IGFBP7-mediated apoptosis. RAS/BRAF mutation status is indicated by the bars, as shown on the legend.

The ability of IGFBP7 to induce apoptosis was assessed in the NCI 60 panel of human cancer cell lines, which were obtained from the National Cancer Institute (NCI). The panel includes cell lines corresponding to breast (MDA-MB-231, HS 578T, BT-549, T47-D, MCF7), ovarian (NCI-ADR-RES, OVCAR-3, OVCAR-5, OVCAR-8, OVCAR-4, SK-OV-3, IGROV1), prostate (DU-145, PC-3), renal (TK-10, CAKI-1, A496, ACHN, RXF-393, 786-O, SN12C, UO-31), non-small cell lung (NCI-H460, HOP-62, A549-ATCC, NCI-H226, EKVX, NCI-H322M, HOP-92, NCI-H522), central nervous system (CNS) (SF-295, SF-268, SF-539, SNB-19, SNB-75, U251), colon (HCT-15, SW-620, COLO205, HT29, HCC-2998, HCT-116, SM-12), melanoma (SK-MEL-28, SK-M2L-2, LOX IMV1, M14, MALM-3M, SK-MEL-5, UACC-257, UACC-62, MDA-MB-435), and hematopoietic (CCRF-CEM, K-562, MOLT-4, SR, RPMI-8226) cancers. These cell lines have been extensively characterized and their mutational status for a number of human cancer genes, including BRAF and RAS (e.g., NRAS, KRAS, or HRAS), is known (see the World Wide Web at discover.nci.nih.gov/cellminer/mutationGeneLoad.do).

rIGFBP7 was expressed and purified as described above. To monitor apoptosis following rIGFBP7 treatment, $5 \times 10^5$ cells were treated with rIGFBP7 (10 μg/ml) for 24 hours and stained for Annexin V-PE. The results are shown in FIG. 11A. rIGFBP7 induced apoptosis in 11/11 (100%) of the cell lines that contained a BRAF mutation and 8/13 (61.5%) of the cell lines that contained a RAS mutation. One cell line contained both a BRAF and a RAS mutation, and this cell line was susceptible to rIGFBP7-mediated apoptosis. Of cell lines that did not contain a BRAF or RAS mutation, only 4/34 (11.8%) were susceptible to apoptosis mediated by rIGFBP7.

Figure 11B:
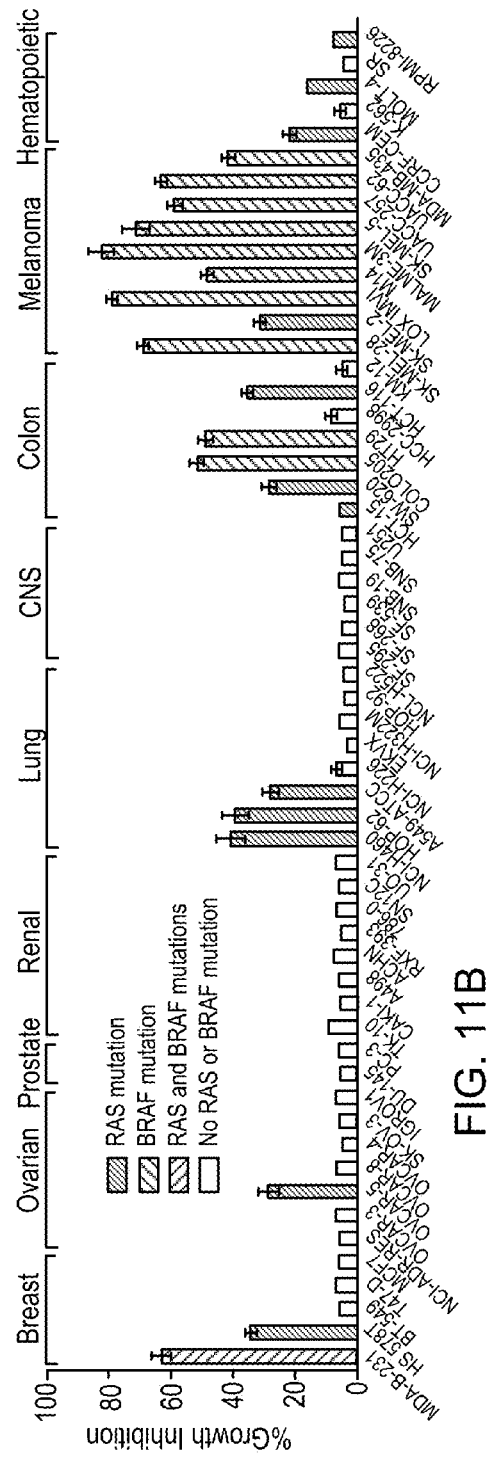
FIG. 11B is a bar graph depicting sensitivity of the indicated human cancer cell lines to growth inhibition by the MEK inhibitor U0216. RAS/BRAF mutation status is indicated by the bars, as shown on the legend.

The growth dependence of the above cell lines on the Ras-BRAF-MEK-Erk signaling pathway was also determined. $1.5 \times 10^5$ cells of each cell line were treated with 20 μM of the MEK inhibitor U0216 (Cell Signaling) for 24 hours, and growth of the cell lines was determined. The results are shown in FIG. 11B. U0216 inhibited growth in 11/11 (100%) of the cell lines that contained a BRAF mutation and 11/13 (84.6) of the cell lines that contained a RAS mutation. The one cell line that contained both a BRAF and a RAS mutation was susceptible to growth inhibition by U0216. None of the cell lines (0/34) that did not contain a BRAF or RAS mutation were susceptible to growth inhibition by U0216.

Example 11

IGFBP7 Suppresses Xenograft Metastasis and Enhances Survival

As a first test of whether IGFBP7 can be used to treat metastatic melanoma, a well-established mouse model of metastatic disease was used in which human melanoma cells form pulmonary metastases following tail vein injection (see, for example, Collisson et al., 2003, Cancer Res., 63:5669-73; Hoeflich et al., 2006, Cancer Res., 66:999-1006; Zimmerman et al., 1987, Cancer Res., 47:2305-10). For these experiments, A375(Fluc-IRES-GFP) cells were used, which are a highly metastatic, BRAF-positive human melanoma cell line stably expressing an Fluc-IRES-GFP reporter construct (where Fluc is the firefly luciferase gene, IRES is an internal ribosomal entry site and GFP is green fluorescent protein) (Collisson et al., 2003, Cancer Res., 63:5669-5673). The presence of Fluc-IRES-GFP enables tumor growth to be quantified over time in live animals by serial bioluminescent optical imaging.

Figure 12A:
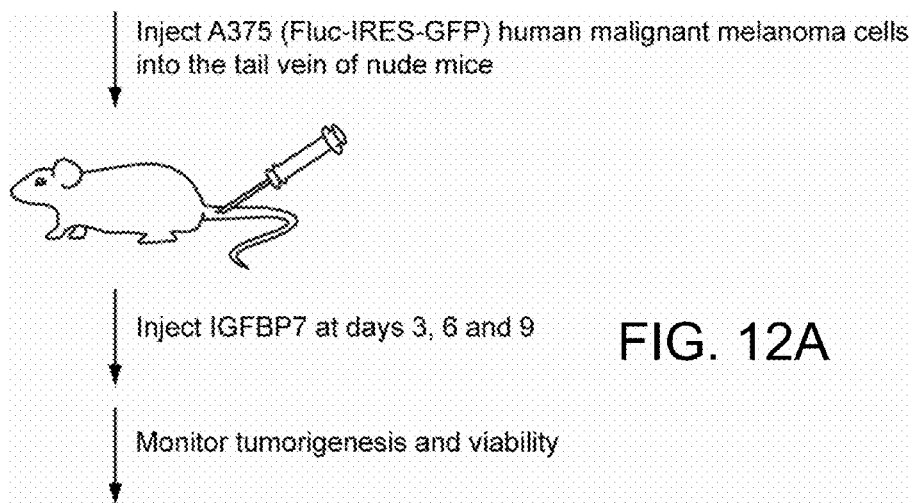
FIG. 12A is a schematic diagram of an experimental protocol to determine the effect of IGFBP7 on metastatic lung tumors in xenografted mice.
Figures 12B, 12C:
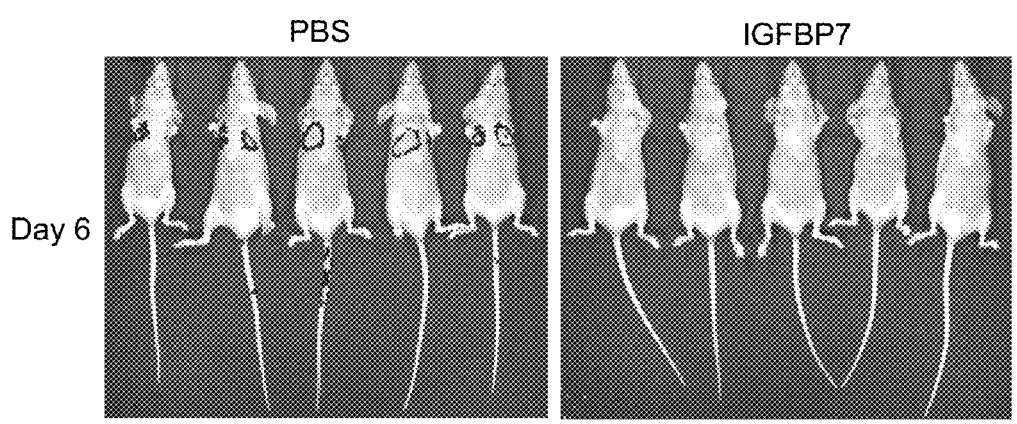
FIGS. 12B and 12C are a pair of representations of photographs of mice showing concentrations of GFP-expressing cells in vivo at day six following injection with A375 (Fluc-IRES-GFP) cells.
Figure 12D:
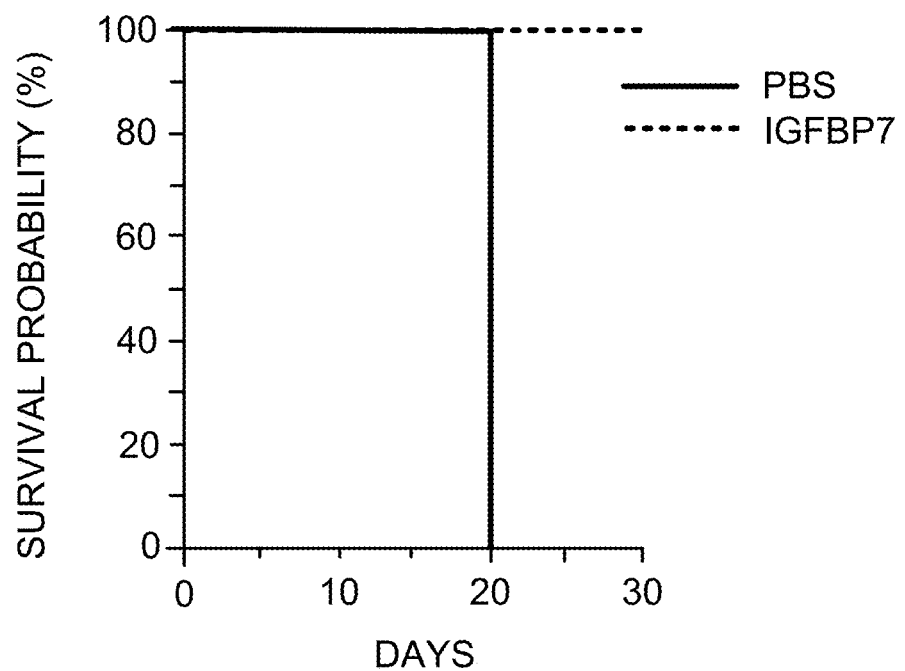
FIG. 12D is a chart depicting Kaplan-Meier analysis of survival of mice over the course of the experiment.

Two treatment regimens were tested. In one set of experiments, administration of IGFBP7 was initiated 3 days after injection of A375-Fluc cells, at which time metastatic disease would be significant (FIG. 12A). In these experiments, $7 \times 10^5$ A375(Fluc-IRES-GFP) cells were injected into the tail vein of 10 athymic Balb/c (nu/nu) mice (Taconic). At days 3, 6 and 9, mice were injected via the tail vein with either 100 μg purified, recombinant IGFBP7 (n=5 mice) or, as a control, phosphate buffered saline (PBS) (n=5 mice). On day 6, mice were analyzed for quantitation of metastatic tumor burden by using a Xenogen brand bioluminescent imaging system. As expected, mice injected with PBS displayed metastatic lung tumors (FIG. 12B), whereas mice injected with rIGFBP7 showed no evidence of lung metastasis (FIG. 12C). Mice were monitored daily for viability over 30 days, and the ability of systemically administered IGFBP7 to suppress metastatic disease was assessed by survival assays (Kaplan-Meier analysis). FIG. 12D shows that all 5 control mice died at 20 days following injection of A375(Fluc-IRES-GFP) cells whereas mice injected with rIGFBP7 were still viable at day 30.

Figure 13A:
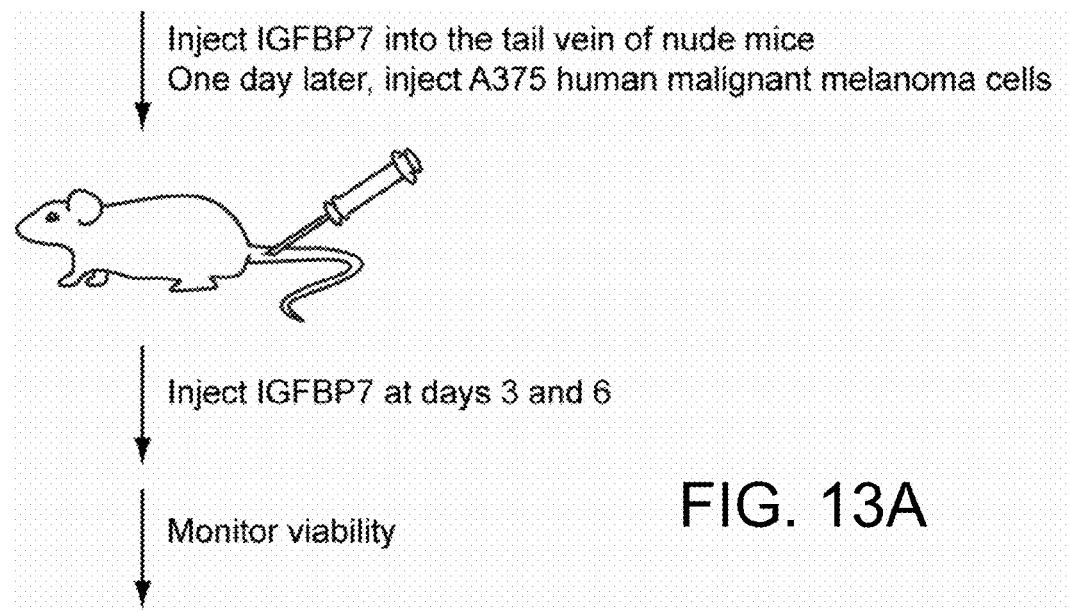
FIG. 13A is a schematic diagram of an experimental protocol to determine the effect of IGFBP7 on metastatic lung tumors in xenografted mice.
Figure 13B:
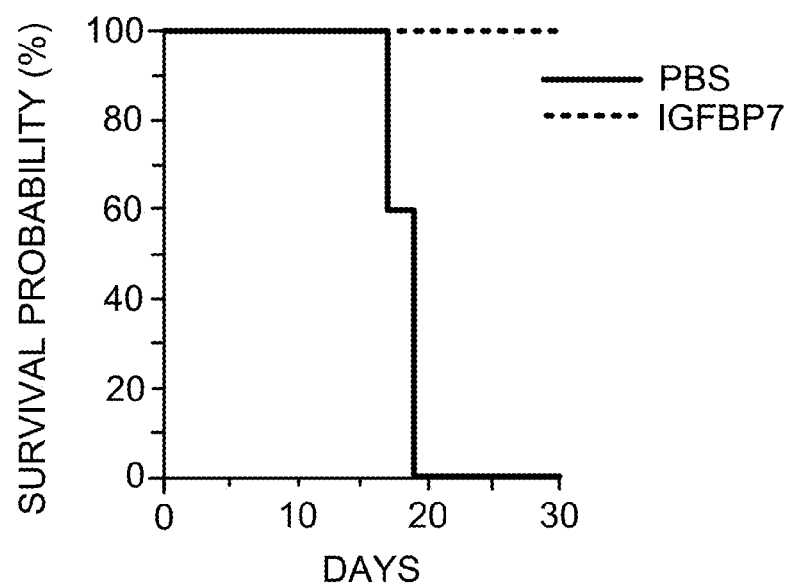
FIG. 13B is a chart depicting Kaplan-Meier analysis of survival of mice over the course of the experiment.

In a second set of experiments, administration of IGFBP7 was initiated both before and shortly after injection of A375 (Fluc-IRES-GFP) cells, to test the ability of IGFBP7 to function prophylactically to prevent metastasis and/or treat early metastatic disease (FIG. 13A). In these experiments, 100 μg purified, recombinant IGFBP7 (or, as a control, PBS) was injected into the tail vein of mice (n=5 mice for each group). One day later, mice were injected with 7×10$^5$ A375(Fluc-IRES-GFP) cells, followed by injection of 100 μg on days 3 and 6. Mice were monitored daily for viability over 30 days, and the ability of systemically administered IGFBP7 to suppress metastatic disease was assessed by survival assays (Kaplan-Meier analysis). The results of FIG. 13B show that mice treated with PBS died within 18 days following injection of A375(Fluc-IRES-GFP) cells, whereas mice injected with rIGFBP7 were still viable at day 30. These preliminary results strongly support the possibility of using rIGFBP7 to treat and prevent metastatic melanoma.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a tumor in a subject, the method comprising:
   identifying a subject having a tumor that has a cell having increased Ras-BRAF-MEK-Erk signaling, is dependent for growth and/or survival upon the Ras-BRAF-MEK-Erk signaling pathway, and/or expresses an activated or oncogenic BRAF or RAS; and
   administering to the subject an effective amount of an IGFBP7 polypeptide at least 80% identical to SEQ ID NO:1 or SEQ ID NO:7, thereby treating the tumor.

2. The method of claim 1, wherein the tumor is a cancer.

3. The method of claim 2, wherein the cancer is a melanoma.

4. The method of claim 2, wherein the cancer is a carcinoma, breast cancer, ovarian cancer, pancreatic cancer, colon cancer, colorectal carcinoma, or papillary thyroid carcinoma.

5. The method of claim 2, wherein the cancer expresses an activated or oncogenic BRAF or RAS.

6. The method of claim 2, wherein the activated or oncogenic BRAF is BRAFV600E.

7. The method of claim 1, wherein the oncogenic BRAF is BRAFV600E.

8. The method of claim 1, wherein the polypeptide is at least 85% identical to SEQ ID NO:1 or SEQ ID NO:7.

9. The method of claim 1, wherein the polypeptide is conjugated to a heterologous moiety.

10. The method of claim 9, wherein the heterologous moiety is a heterologous polypeptide sequence.

11. The method of claim 1, wherein the IGFBP7 agent consists of a polypeptide at least 80% identical to SEQ ID NO:1 or SEQ ID NO:7.

12. The method of claim 11, wherein the polypeptide is at least 85% identical to SEQ ID NO:1 or SEQ ID NO:7.

13. The method of claim 1, wherein the IGFBP7 polypeptide is administered by introducing to the subject a nucleic acid encoding a polypeptide at least 85% identical to SEQ ID NO:1 or SEQ ID NO:7.

14. The method of claim 13, wherein the nucleic acid is in a viral vector.

15. The method of claim 14, wherein the viral vector is an adenovirus, adeno-associated virus, retrovirus, or lentivirus vector.

16. The method of claim 1, wherein the IGFBP7 agent is administered topically, systemically, or locally.

17. The method of claim 16, wherein the IGFBP7 agent is administered locally by a drug-releasing implant.

18. A method of inhibiting proliferation of a cell that has increased Ras-BRAF-MEK-Erk signaling, is dependent for growth and/or survival upon the Ras-BRAF-MEK-Erk signaling pathway, and/or expresses an activated or oncogenic BRAF or RAS, the method comprising
   identifying a cell that has increased Ras-BRAF-MEK-Erk signaling, is dependent for growth and/or survival upon the Ras-BRAF-MEK-Erk signaling pathway, and/or expresses an activated or oncogenic BRAF or RAS; and
   administering to the cell an effective amount of an IGFBP7 polypeptide.

19. The method of claim 18, wherein the cell is a tumor cell.

20. A method of treating a melanoma in a subject, the method comprising:
   identifying a subject having, at risk for, or suspected of having a melanoma; and
   administering to the subject an effective amount of an IGFBP7 polypeptide at least 80% identical to SEQ ID NO:1 or SEQ ID NO:7, thereby treating the melanoma.

* * * * *

SEQUENCE LISTING

<160> NUMBER OF SEQ ID NOS: 12

<210> SEQ ID NO 1
<211> LENGTH: 282
<212> TYPE: PRT
<213> ORGANISM: Homo sapiens

<400> SEQUENCE: 1

```
Met Glu Arg Pro Ser Leu Arg Ala Leu Leu Leu Gly Ala Ala Gly Leu
1               5                   10                  15

Leu Leu Leu Leu Leu Pro Leu Ser Ser Ser Ser Ser Asp Thr Cys
            20                  25                  30

Gly Pro Cys Glu Pro Ala Ser Cys Pro Pro Leu Pro Pro Leu Gly Cys
        35                  40                  45

Leu Leu Gly Glu Thr Arg Asp Ala Cys Gly Cys Cys Pro Met Cys Ala
    50                  55                  60

Arg Gly Glu Gly Glu Pro Cys Gly Gly Gly Ala Gly Arg Gly Tyr
65                  70                  75                  80

Cys Ala Pro Gly Met Glu Cys Val Lys Ser Arg Lys Arg Arg Lys Gly
                85                  90                  95

Lys Ala Gly Ala Ala Gly Gly Pro Gly Val Ser Gly Val Cys Val
            100                 105                 110

Cys Lys Ser Arg Tyr Pro Val Cys Gly Ser Asp Gly Thr Thr Tyr Pro
        115                 120                 125

Ser Gly Cys Gln Leu Arg Ala Ala Ser Gln Arg Ala Glu Ser Arg Gly
    130                 135                 140

Glu Lys Ala Ile Thr Gln Val Ser Lys Gly Thr Cys Glu Gln Gly Pro
145                 150                 155                 160

Ser Ile Val Thr Pro Pro Lys Asp Ile Trp Asn Val Thr Gly Ala Gln
                165                 170                 175

Val Tyr Leu Ser Cys Glu Val Ile Gly Ile Pro Thr Pro Val Leu Ile
            180                 185                 190

Trp Asn Lys Val Lys Arg Gly His Tyr Gly Val Gln Arg Thr Glu Leu
        195                 200                 205

Leu Pro Gly Asp Arg Asp Asn Leu Ala Ile Gln Thr Arg Gly Gly Pro
    210                 215                 220

Glu Lys His Glu Val Thr Gly Trp Val Leu Val Ser Pro Leu Ser Lys
```

```
                225                 230                 235                 240

Glu Asp Ala Gly Glu Tyr Glu Cys His Ala Ser Asn Ser Gln Gly Gln
                    245                 250                 255

Ala Ser Ala Ser Ala Lys Ile Thr Val Val Asp Ala Leu His Glu Ile
                260                 265                 270

Pro Val Lys Lys Gly Glu Gly Ala Glu Leu
            275                 280

<210> SEQ ID NO 2
<211> LENGTH: 1124
<212> TYPE: DNA
<213> ORGANISM: Homo sapiens

<400> SEQUENCE: 2
gccgctgcca ccgcaccccg ccatggagcg gccgtcgctg cgcgccctgc tcctcggcgc     60
cgctgggctg ctgctcctgc tcctgcccct ctcctcttcc tcctcttcgg acacctgcgg    120
cccctgcgag ccggcctcct gcccgcccct gccccgctg gctgcctgc tgggcgagac    180 ccgcgacgcg tgcggctgct gccctatgtg cgcccgcggc gagggcgagc cgtgcggggg    240
tggcggcgcc ggcaggggt actgcgcgcc gggcatggag tgcgtgaaga ccgcaagag    300 gcggaagggt aaagccgggg cagcagccgg cggtccgggt gtaagcggcg tgtgcgtgtg    360
caagagccgc tacccggtgt gcggcagcga cggcaccacc tacccgagcg gctgccagct    420
gcgcgccgcc agccagaggg ccgagagccg cggggagaag gccatcaccc aggtcagcaa    480
gggcacctgc gagcaaggtc cttccatagt gacgcccccc aaggacatct ggaatgtcac    540
tggtgcccag gtgtacttga gctgtgaggt catcggaatc ccgacacctg tcctcatctg    600
gaacaaggta aaaggggtc actatggagt tcaaaggaca gaactcctgc ctggtgaccg    660
ggacaacctg gccattcaga cccggggtgg cccagaaaag catgaagtaa ctggctgggt    720
gctggtatct cctctaagta aggaagatgc tggagaatat gagtgccatg catccaattc    780
ccaaggacag gcttcagcat cagcaaaaat tacagtggtt gatgccttac atgaaatacc    840
agtgaaaaaa ggtgaaggtg ccgagctata aacctccaga atattattag tctgcatggt    900
taaaagtagt catggataac tacattacct gttcttgcct aataagtttc ttttaatcca    960
atccactaac actttagtta tattcactgg ttttacacag agaaatacaa aataaagatc   1020
acacatcaag actatctaca aaatttatt atatatttac agaagaaaag catgcatatc   1080
attaaacaaa taaatactt tttatcacaa aaaaaaaaaa aaaa                     1124

<210> SEQ ID NO 3
<211> LENGTH: 766
<212> TYPE: PRT
<213> ORGANISM: Homo sapiens

<400> SEQUENCE: 3

Met Ala Ala Leu Ser Gly Gly Gly Gly Gly Ala Glu Pro Gly Gln
 1               5                  10                  15

Ala Leu Phe Asn Gly Asp Met Glu Pro Glu Ala Gly Ala Gly Ala Gly
                20                  25                  30

Ala Ala Ala Ser Ser Ala Ala Asp Pro Ala Ile Pro Glu Glu Val Trp
            35                  40                  45

Asn Ile Lys Gln Met Ile Lys Leu Thr Gln Glu His Ile Glu Ala Leu
     50                  55                  60

Leu Asp Lys Phe Gly Gly Glu His Asn Pro Pro Ser Ile Tyr Leu Glu
65                  70                  75                  80
```

```
Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
            115                 120                 125

Ser Val Leu Pro Ser Ser Leu Ser Val Phe Gln Asn Pro Thr Asp Val
        130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
            195                 200                 205

Gly Trp Asp Thr Asp Ile Ser Trp Leu Thr Gly Glu Glu Leu His Val
        210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
            275                 280                 285

Leu Phe Val Ser Lys Phe Phe Glu His His Pro Ile Pro Gln Glu Glu
        290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
            355                 360                 365

Val His Ile Asn Thr Ile Glu Pro Val Asn Ile Asp Asp Leu Ile Arg
        370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
        450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495
```

```
Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 4
<211> LENGTH: 2477
<212> TYPE: DNA
<213> ORGANISM: Homo sapiens

<400> SEQUENCE: 4 cgcctcccctt cccctcccc gcccgacagc ggccgctcgg gccccggctc tcggttataa      60
gatggcggcg ctgagcggtg gcggtggtgg cggcgcggag ccgggccagg ctctgttcaa     120
cggggacatg gagcccgagg ccggcgccgg cgccggcgcc gcggcctctt cggctgcgga     180
ccctgccatt ccggaggagg tgtggaatat caaacaaatg attaagttga cacaggaaca     240
tatagaggcc ctattggaca aatttggtgg ggagcataat ccaccatcaa tatatctgga     300
ggcctatgaa gaatacacca gcaagctaga tgcactccaa caaagagaac aacagttatt     360
ggaatctctg gggaacggaa ctgatttttc tgtttctagc tctgcatcaa tggataccgt     420
tacatcttct tcctcttcta gcctttcagt gctaccttca tctctttcag ttttcaaaa     480 tcccacagat gtggcacgga gcaaccccaa gtcaccacaa aaacctatcg ttagagtctt     540
cctgcccaac aaacagagga cagtggtacc tgcaaggtgt ggagttacag tccgagacag     600
```

```
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact tgtacgaaaa    780
aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat ccccttccgc   1020
acccgcctcg gactctattg gcccccaaat tctcaccagt ccgtctcctt caaaatccat   1080
tccaattcca cagcccttcc gaccagcaga tgaagatcat cgaaatcaat ttgggcaacg   1140
agaccgatcc tcatcagctc caatgtgcca tataaacaca atagaacctg tcaatattga   1200
tgacttgatt agagaccaag gatttcgtgg tgatggagga tcaaccacag gtttgtctgc   1260
tacccccct gcctcattac ctggctcact aactaacgtg aaagccttac agaaatctcc   1320
aggacctcag cgagaaagga gtcatcttc atcctcagaa acaggaatc gaatgaaaac   1380
acttggtaga cgggactcga gtgatgattg ggagattcct gatgggcaga ttacagtggg   1440
acaaagaatt ggatctggat catttggaac agtctacaag ggaaagtggc atggtgatgt   1500
ggcagtgaaa atgttgaatg tgacagcacc tacacctcag cagttacaag ccttcaaaaa   1560
tgaagtagga gtactcagga aaacacgaca tgtgaatatc ctactcttca tgggctattc   1620
cacaaagcca caactggcta ttgttaccca gtggtgtgag ggctccagct tgtatcacca   1680
tctccatatc attgagacca aatttgagat gatcaaactt atagatattg cacgacagac   1740
tgcacagggc atggattact tacacgccaa gtcaatcatc cacagagacc tcaagagtaa   1800
taatatttt cttcatgaag acctcacagt aaaaataggt gattttggtc tagctacagt   1860
gaaatctcga tggagtgggt cccatcagtt tgaacagttg tctggatcca tttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct ttccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg caggggata   2340
tggtgcgttt cctgtccact gaaacaaatg agtgagagag ttcaggagag tagcaacaaa   2400
aggaaaataa atgaacatat gtttgcttat atgttaaatt gaataaaata ctctcttttt   2460
ttttaaggtg aaccaaa                                                 2477
```

<210> SEQ ID NO 5
<211> LENGTH: 189
<212> TYPE: PRT
<213> ORGANISM: Homo sapiens

<400> SEQUENCE: 5

```
Met Thr Glu Tyr Lys Leu Val Val Val Gly Ala Gly Gly Val Gly Lys
  1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
```

```
                35                  40                  45
Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Ser Lys Ser Phe Ala Asp Ile Asn Leu Tyr
                 85                  90                  95

Arg Glu Gln Ile Lys Arg Val Lys Asp Ser Asp Val Pro Met Val
                100                 105                 110

Leu Val Gly Asn Lys Cys Asp Leu Pro Thr Arg Thr Val Asp Thr Lys
                115                 120                 125

Gln Ala His Glu Leu Ala Lys Ser Tyr Gly Ile Pro Phe Ile Glu Thr
                130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
                180                 185
```

<210> SEQ ID NO 6
<211> LENGTH: 1963
<212> TYPE: DNA
<213> ORGANISM: Homo sapiens

<400> SEQUENCE: 6

```
gaaacgtccc gtgtgggagg ggcgggtctg ggtgcggctg ccgcatgact cgtggttcgg     60
aggcccacgt ggccggggcg gggactcagg cgcctggcag ccgactgatt acgtagcggg    120
cggggccgga agtgccgctc cttggtgggg gctgttcatg gcggttccgg ggtctccaac    180
atttttcccg gtctgtggtc ctaaatctgt ccaaagcaga ggcagtggag cttgaggttc    240
ttgctggtgt gaaatgactg agtacaaact ggtggtggtt ggagcaggtg gtgttgggaa    300
aagcgcactg acaatccagc taatccagaa ccactttgta gatgaatatg atcccaccat    360
agaggattct tacagaaaac aagtggttat agatggtgaa acctgtttgt tggacatact    420
ggatacagct ggacaagaag agtacagtgc catgagagac caatacatga ggacaggcga    480
aggcttcctc tgtgtatttg ccatcaataa tagcaagtca tttgcggata ttaacctcta    540
cagggagcag attaagcgag taaaagactc ggatgatgta cctatggtgc tagtgggaaa    600
caagtgtgat ttgccaacaa ggacagttga tacaaaacaa gcccacgaac tggccaagag    660
ttacgggatt ccattcattg aaacctcagc aagaccaga  cagggtgttg aagatgcttt    720
ttacacactg gtaagagaaa tacgccagta ccgaatgaaa aaactcaaca gcagtgatga    780
tgggactcag ggttgtatgg gattgccatg tgtggtgatg taacaagata cttttaaagt    840
tttgtcagaa aagagccact ttcaagctgc actgacaccc tggtcctgac ttcctggagg    900
agaagtattc ctgttgctgt cttcagtctc acagagaagc tcctgctact tccccagctc    960
tcagtagttt agtacaataa tctctatttg agaagttctc agaataacta cctcctcact   1020
tggctgtctg accagagaat gcacctcttg ttactccctg ttattttttct gccctgggtt   1080
cttccacagc acaaacacac ctcaacacac ctctgccacc ccaggttttt catctgaaaa   1140
gcagttcatg tctgaaacag agaaccaaac cgcaaacgtg aaattctatt gaaacagtg   1200
tcttgagctc taaagtagca actgctggtg attttttttt tcttttttact gttgaactta   1260
```

```
gaactatgcc taatttttgg agaaatgtca taaattactg ttttgccaag aatatagtta    1320
ttattgctgt ttggtttgtt tataatgtta tcggctctat tctctaaact ggcatctgct    1380
ctagattcat aaatacaaaa atgaatactg aattttgagt ctatcctagt cttcacaact    1440
ttgacgtaat taaatccaac ttttcacagt gaagtgcctt tttcctagaa gtggtttgta    1500
gactccttta taatatttca gtggaataga tgtctcaaaa atccttatgc atgaaatgaa    1560
tgtctgagat acgtctgtga cttatctacc attgaaggaa agctatatct atttgagagc    1620
agatgccatt ttgtacatgt atgaaattgg ttttccagag gcctgttttg gggctttccc    1680
aggagaaaga tgaaactgaa agcatatgaa taatttcact taataatttt tacctaatct    1740
ccactttttt cataggttac tacctataca atgtatgtaa tttgtttccc ctagcttact    1800
gataaaccta atattcaatg aacttccatt tgtattcaaa tttgtgtcat accagaaagc    1860
tctacatttg cagatgttca aatattgtaa aactttggtg cattgttatt taatagctgt    1920
gatcagtgat tttcaaacct caaatatagt atattaacaa att                      1963
```

<210> SEQ ID NO 7
<211> LENGTH: 20
<212> TYPE: PRT
<213> ORGANISM: Homo sapiens

<400> SEQUENCE: 7

Gly Met Glu Cys Val Lys Ser Arg Lys Arg Arg Lys Gly Lys Ala Gly
 1               5                  10                  15

Ala Ala Ala Gly
            20

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
gctcgcttcg gcagcacata tac                                              23

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gagacgtgct acttccattt gtc                                              23

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gagggcctat ttcccatgat                                                  20

<210> SEQ ID NO 11
<211> LENGTH: 23
<212> TYPE: DNA
<213> ORGANISM: Artificial Sequence

```
<220> FEATURE:
<223> OTHER INFORMATION: Primer

<400> SEQUENCE: 11
tcataatgct tgctctgata gga                                              23

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ggccaaaatt taatcagtgg a                                                21
```